US008440220B2

(12) United States Patent
Gale et al.

(10) Patent No.: US 8,440,220 B2
(45) Date of Patent: *May 14, 2013

(54) TRANSDERMAL ANALGESIC SYSTEMS WITH REDUCED ABUSE POTENTIAL

(75) Inventors: Robert M. Gale, Los Altos, CA (US);
Thomas M. Stein, San Jose, CA (US);
Jay Audett, Mountain View, CA (US);
Jane Stepic, San Carlos, CA (US);
Joseph B. Phipps, Sunnyvale, CA (US);
Michel J. N. Cormier, Mountain View, CA (US)

(73) Assignee: Durect Corporation, Cupertino, CA (US)

( * ) Notice: Subject to any disclaimer, the term of this patent is extended or adjusted under 35 U.S.C. 154(b) by 828 days.

This patent is subject to a terminal disclaimer.

(21) Appl. No.: 10/420,428

(22) Filed: Apr. 22, 2003

(65) Prior Publication Data
US 2004/0013716 A1 Jan. 22, 2004

Related U.S. Application Data

(60) Provisional application No. 60/375,110, filed on Apr. 23, 2002.

(51) Int. Cl.
*A61K 9/70* (2006.01)
(52) U.S. Cl.
USPC ......................................................... 424/449
(58) Field of Classification Search .................. 424/449, 424/448
See application file for complete search history.

(56) References Cited

U.S. PATENT DOCUMENTS

| 3,493,657 | A | | 2/1970 | Lewenstein et al. |
|---|---|---|---|---|
| 3,773,955 | A | | 11/1973 | Pachter et al. |
| 4,457,933 | A | | 7/1984 | Gordon et al. |
| 4,464,378 | A | | 8/1984 | Hussain |
| 4,466,953 | A | | 8/1984 | Keith et al. |
| 4,470,962 | A | | 9/1984 | Keith et al. |
| 4,588,580 | A | | 5/1986 | Gale et al. |
| 4,626,539 | A | | 12/1986 | Aungst et al. |
| 4,806,341 | A | | 2/1989 | Chien et al. |
| 4,935,428 | A | | 6/1990 | Lewis |
| 5,006,342 | A | * | 4/1991 | Cleary et al. .................. 424/445 |
| 5,149,538 | A | * | 9/1992 | Granger et al. ............... 424/449 |
| 5,186,939 | A | | 2/1993 | Cleary et al. |
| 5,236,714 | A | | 8/1993 | Lee et al. |

(Continued)

FOREIGN PATENT DOCUMENTS

| WO | WO 00/01377 | * | 7/1999 |
|---|---|---|---|
| WO | WO 0001377 | | 1/2000 |

(Continued)

OTHER PUBLICATIONS

Reeves, M.D. et al., "Fatal intravenous misuse of transdermal fentanyl", Medical Journal of Australia, vol. 177, No. 10, (2002); pp. 552-553.

(Continued)

*Primary Examiner* — Aradhana Sasan

(57) ABSTRACT

A transdermal analgesic system having reduced potential for abuse, wherein the system provides for the controlled release of the antagonist at a rate sufficient to provide an abuse limiting release rate ratio of the antagonist to the analgesic when the dosage form is subject to abuse is disclosed.

85 Claims, 21 Drawing Sheets

U.S. PATENT DOCUMENTS

| | | | |
|---|---|---|---|
| 5,310,559 A | 5/1994 | Shah et al. | |
| 5,474,783 A | 12/1995 | Miranda et al. | |
| 5,656,286 A | 8/1997 | Miranda et al. | |
| 5,762,952 A | 6/1998 | Barnhart et al. | |
| 5,785,991 A | 7/1998 | Burkoth et al. | |
| 5,843,468 A | 12/1998 | Burkoth et al. | |
| 5,882,676 A | 3/1999 | Lee et al. | |
| 5,958,446 A | 9/1999 | Miranda et al. | |
| 5,985,317 A | 11/1999 | Venkateshwaran et al. | |
| 5,993,849 A | 11/1999 | Assmus et al. | |
| 6,004,578 A | 12/1999 | Lee et al. | |
| 6,024,976 A | 2/2000 | Miranda et al. | |
| 6,063,399 A | 5/2000 | Assmus et al. | |
| 6,139,866 A | 10/2000 | Chono et al. | |
| 6,221,383 B1* | 4/2001 | Miranda et al. | 424/449 |
| 6,231,885 B1* | 5/2001 | Carrara | 424/448 |
| 6,569,449 B1* | 5/2003 | Stinchcomb et al. | 424/449 |
| 6,716,449 B2* | 4/2004 | Oshlack et al. | 424/449 |
| 6,835,194 B2* | 12/2004 | Johnson et al. | 604/890.1 |
| 2005/0095279 A1* | 5/2005 | Gale et al. | 424/449 |

FOREIGN PATENT DOCUMENTS

| | | |
|---|---|---|
| WO | WO 01/58451 A1 | 8/2001 |
| WO | WO 0226217 | 4/2002 |
| WO | WO 02/074286 A1 | 9/2002 |
| WO | WO 02087482 | 11/2002 |

OTHER PUBLICATIONS

Levine, J.D. et al., "Potentiation of Pentazocine Analgesia by Low-dose Naloxone", J. Clin. Invest. (1988); 82, pp. 1574-1577.

Crain, S.M. et al., "Antagonists of excitatory opioid receptor functions enhance morphine's analgesic potency and attenuate opioid tolerance/dependence liability", Pain (2000); 84, pp. 121-131.

Gale, R. et al., "Use of Osmotically Active Therapeutic Agents in Monolithic Systems", J. Membrane Sci. (1980); 7, pp. 319-331.

Patini, G.A. et al., "Transdermal Drug Delivery Devices: System Design and Composition", Encyclopedia of Pharmaceutical Technology (1999); 18, pp. 309-337, New York: Marcel Dekker Inc.

Gale, R. et al., "Transdermal Drug Delivery, Passive", Encyclopedia of Controlled Drug Delivery, (1999); 2, pp. 975-991; New York: J Wiley & Sons, Inc.

Physicians Desk Reference, 56$^{th}$ Edition (2002); pp. 1786-1789.

Satas, D., "Acrylic Adhesives", Handbook of Pressure-Sensitive Adhesive Technology, 2$^{nd}$ Edition, (1989); pp. 396-456, Van Nostrand Reinhold, New York.

Chow, S. et al., "Statistical Methods for Average Bioavailability", Design and Analysis of Bioavailability and Bioequivalence Studies, (1992); pp. 70-125; New York, NY.

Schuirmann, D.J., "A Comparison of the Two One-Sided Tests Procedure and the Power Approach for Assessing the Equivalence of Average Bioavailability", J. Pharmaco. Biopharm. (1987); 15, pp. 657-680.

\* cited by examiner

TRANSDERMAL ANALGESIC SYSTEMS WITH REDUCED ABUSE POTENTIAL

RELATED APPLICATION

This application claims the benefit of U.S. Provisional Application No. 60/375,110, filed on Apr. 23, 2002.

TECHNICAL FIELD

The present invention relates to a transdermal analgesic system having reduced potential for abuse. In particular, the invention relates to a system for transdermal administration of fentanyl and analogs thereof to a subject through intact skin over an extended period of time, wherein the system provides for the controlled release of the antagonist at a rate sufficient to provide an abuse limiting release rate ratio of the antagonist to the analgesic when the dosage form (i.e. the transdermal analgesic system) is subject to abuse.

BACKGROUND OF THE INVENTION

The transdermal administration of narcotic analgesics, i.e. opioids, for the treatment of both acute and chronic pain has been described in great detail. The following patents U.S. Pat. Nos. 4,466,953; 4,470,962; 4,588,580; 4,626,539; 5,006,342; 5,186,939; 5,310,559; 5,474,783; 5,656,286; 5,762,952; 5,948,433; 5,985,317; 5,958,446; 5,993,849; 6,024,976; 6,063,399 and 6,139,866 describe various ways of transdermally administering fentanyl and analogs thereof, such as alfentanil, carfentanil, lofentanil, remifentanil, sufentanil, trefentanil and the like, and are incorporated herein by reference. These patents disclose that fentanyl can be administered from a topically applied ointment, cream, or from a transdermal patch.

The potential for abuse of narcotic analgesics by intranasal, oral or parenteral routes is well known. Diversion and abuse of opioids may take several different forms. For example the medication may be used by a person for whom it is not intended, i.e., diversion, or in amounts and/or frequency greater than prescribed, either by the originally prescribed route (e.g., oral or transdermal) or by an alternate route (e.g. parenteral, intravenous, or intranasal). In order to prevent abuse of these substances, it has been proposed to provide dosage forms which combine the abusable substance with an amount of an antagonist for the abusable substance sufficient to eliminate the "high" associated with abuse of the substance without eliminating the other therapeutic benefits for which the drugs are intended to be administered. See, for example, U.S. Pat. Nos. 3,773,955; 3,493,657; 4,464,378; 4,457,933; 4,626,539; 4,806,341; 4,935,428; 5,149,538; and 5,236,714; and International Publication No. WO 01/58451 A1, all of which are incorporated herein by reference. See also, Talwin; Levine J. D., et al, "Potentiation of pentazocine analgesia by low-dose naloxone", J Clin Invest 1988; 82:1574-1577; Crain S M, Shen F-K, "Antagonist of excitatory opioid receptor function enhance morphine's analgesic potency and attenuate opioid tolerance/dependence liability", Pain 2000; 84:121-131, which are incorporated herein by reference.

U.S. Pat. No. 5,236,714 describes transdermal dosage forms for delivering narcotic and psychoactive substances, the dosage form having a reduced potential for abuse. The transdermal dosage forms comprise an analgesic reservoir comprising a narcotic and an antagonist, and a releasing means through which the narcotic is released to the body. U.S. Pat. No. 5,149,538 describes a misuse-resistive dosage form for transdermal administration of opioids. The dosage form comprises an opioid, an antagonist for the opioid that is releasable upon ingestion or solvent immersion, a barrier means separating the opioid from the antagonist and a delivery means for delivering the opioid.

Notwithstanding some success, the existing dosage forms have not been entirely satisfactory for reducing the potential for abuse, since the narcotic can be extracted from the dosage form for injection, inhalation or ingestion; or the narcotic and antagonist may interact resulting in adverse physical and/or chemical interaction, such as undesirable ion exchange or permeation of the antagonist into the narcotic reservoir resulting in systemic delivery of the antagonist. Upon prolonged exposure to skin, the antagonist elicits a sensitization response. Further, the existing dosage forms do not provide for the controlled release of the antagonist at a rate sufficient to provide an abuse limiting release rate ratio of the antagonist to the narcotic when the dosage form is subject to abuse, e.g., upon ingestion or substantial immersion of the system in a solvent. When such dosage forms are subjected to abuse, the antagonist may be isolated at a rate disproportionate to the release rate of the analgesic from the dosage form, such that the opioid effects of the analgesic are insufficiently blocked during abuse situations.

SUMMARY OF THE INVENTION

The present invention is directed to the aforementioned needs in the art, and provides a transdermal analgesic system having reduced potential for abuse, without diminishing the therapeutic or beneficial effects of the analgesic when the system is applied to the skin, wherein the system provides for a substantially minimized/negligible skin sensitization response from antagonist exposure. In particular, the transdermal analgesic system of the present invention provides for the controlled release of the antagonist at a rate sufficient to provide an abuse limiting release rate ratio of the antagonist to the analgesic when the dosage form is subjected to abuse. Additionally, the transdermal analgesic system of the present invention provides improved safety, e.g., in case of accidental ingestion of a used system by children or household pets.

In one aspect, the invention relates to a transdermal system for administering an analgesic through the skin, the system having a reduced potential for abuse, comprising:
  (a) an analgesic reservoir comprising an analgesic, the analgesic being selected from the group consisting of fentanyl and analogs thereof;
  (b) an antagonist reservoir comprising an antagonist for said analgesic;
  (c) a barrier layer, said barrier layer separating said antagonist reservoir from said analgesic reservoir, said barrier layer being substantially impermeable to said analgesic and to said antagonist, wherein the system (i) substantially prevents release of the antagonist from the system upon securing the system to a human patient for a period of up to about 7 days; and (ii) provides release of the antagonist at a rate sufficient to provide an abuse limiting release rate ratio of the antagonist to the analgesic when the dosage form is subject to abuse, e.g., upon ingestion or substantial immersion of the system in the solvent.

In another aspect, the transdermal analgesic system of the invention comprises an analgesic reservoir comprising an amount of analgesic sufficient to induce and maintain analgesia in a human patient for a period of at least three days, wherein the analgesic is fentanyl or an analog thereof and the analog is selected from the group consisting of alfentanil, lofentanil, remifentanil, sufentanil and trefentanil. In preferred embodiments, the analgesic is fentanyl or sufentanil, more preferably, base form of fentanyl or sufentanil.

In additional aspects, the transdermal analgesic system of the invention comprises an analgesic reservoir comprising a polymeric matrix comprising about 1 wt % to about 20 wt % of the analgesic, and optionally a permeation enhancer. Preferably, the analgesic reservoir comprises a single phase formulation free of undissolved components.

In another aspect, the transdermal analgesic system of the invention comprises an analgesic reservoir comprising an aqueous gel comprising up to about 20 wt % of the analgesic, up to about 50 wt % permeation enhancer, and about 0.5 to about 10 wt % gelling agent.

In additional aspects, the transdermal analgesic system of the invention further comprises an analgesic release rate controlling means disposed between the analgesic reservoir and the skin. In certain aspects, the analgesic release rate controlling means is less permeable to the analgesic than to the permeation enhancer.

In additional aspects, the transdermal analgesic system of the invention comprises an antagonist reservoir comprising an antagonist in a form that is not releasable through the barrier layer, the antagonist being releasable from system upon being ingested or substantially immersed in a solvent. Preferably, the antagonist reservoir comprises the antagonist dispersed within a polymer, wherein the antagonist is substantially insoluble in the antagonist reservoir polymer. In certain embodiments, the antagonist is dispersed in a matrix comprising a material that substantially prevents release of the antagonist; or the antagonist is complexed with an ionic resin. In additional embodiments, the antagonist reservoir comprises the antagonist in a multiparticulate form, wherein each particle is individually coated with a material that substantially prevents release of the antagonist. In additional embodiments, the antagonist reservoir comprises beads coated with the antagonist, wherein the beads may be formed from glass or an inert or non-dissolvable polymer, and further wherein the coated beads are optionally coated with or dispersed in material that substantially prevents release of the antagonist. The antagonist is selected from the group consisting of naltrexone, methyinaltrexone, naloxone, nalbuphine, nalorphine, nalorphine dinicotinate, nalmefene, nadide, levallorphan, cyclozocine and pharmaceutically acceptable salts thereof. In preferred embodiments, the antagonist is present as a salt, preferably as a hydrochloride salt of an antagonist base.

In additional aspects, the transdermal analgesic system of the invention comprises a barrier layer impermeable to the analgesic and the antagonist; wherein the barrier layer comprises a material that is insoluble in water, alcohol and organic solvents. The antagonist reservoir is disposed on the skin distal surface of the barrier layer and the analgesic reservoir is disposed on the skin proximal surface of the barrier layer.

In additional aspects, the transdermal analgesic system of the invention further comprises an antagonist release rate controlling means, wherein said antagonist release rate controlling means substantially prevents release of the antagonist from the system upon securing the system to a human patient for a period of up to about 7 days; and provides release of the antagonist at a rate sufficient to provide an abuse limiting release rate ratio of the antagonist to the analgesic when the dosage form is subject to abuse, e.g., upon ingestion or substantial immersion of the system in the solvent. The antagonist release rate controlling means is disposed on the skin distal surface of the antagonist reservoir.

In another aspect, the transdermal analgesic system of the invention, when the dosage form is subject to abuse, e.g., upon ingestion or immersion in a solvent for a period of time, substantially continuously provides a release rate ratio of the antagonist to the analgesic of about 0.075:1 to about 30:1, about 0.25:1 to about 20:1; about 0.5:1 to about 16:1; about 0.5:1 to about 14:1; about 0.75:1 to about 12:1; about 1:1 to about 10:1, about 1.5:1 to about 8:1; about 2:1 to about 6:1; and about 2:1 to about 4:1, wherein the period of time of immersion is up to about 1 minute to about 24 hours.

In another aspect, the invention relates to a transdermal system for administering an analgesic through the skin, the system having a reduced potential for abuse, comprising:
(a) an analgesic reservoir comprising an amount of analgesic sufficient to induce and maintain analgesia in a human patient for a period of at least three days, wherein the analgesic is fentanyl or an analog thereof and the analog is selected from the group consisting of alfentanil, lofentanil, remifentanil, sufentanil and trefentanil;
(b) an antagonist reservoir comprising an antagonist for said analgesic, wherein the antagonist in a form that is not releasable through the barrier layer, the antagonist being releasable from system upon being ingested or substantially immersed in a solvent, and further wherein the antagonist is selected from the group consisting of naltrexone, methylnaltrexone, naloxone, nalbuphine, nalorphine, nalorphine dinicotinate, nalmefene, nadide, levallorphan, cyclozocine and pharmaceutically acceptable salts thereof;
(c) a barrier layer, said barrier layer separating said antagonist reservoir from said analgesic reservoir, said barrier layer being substantially impermeable to said analgesic and to said antagonist; and
(d) an antagonist release rate controlling means disposed on the skin distal surface of the antagonist reservoir, wherein said antagonist release rate controlling means substantially prevents release of the antagonist from the system upon securing the system to a human patient for a period of up to about 7 days, and further wherein the antagonist release rate controlling means provides release of the antagonist at a rate sufficient to provide an abuse limiting release rate ratio of the antagonist to the analgesic when the dosage form is subject to abuse, e.g., upon ingestion or substantial immersion of the system in the solvent.

These and other embodiments of the present invention will readily occur to those of ordinary skill in the art in view of the disclosure herein.

DETAILED DESCRIPTION OF THE INVENTION

Figure 1:
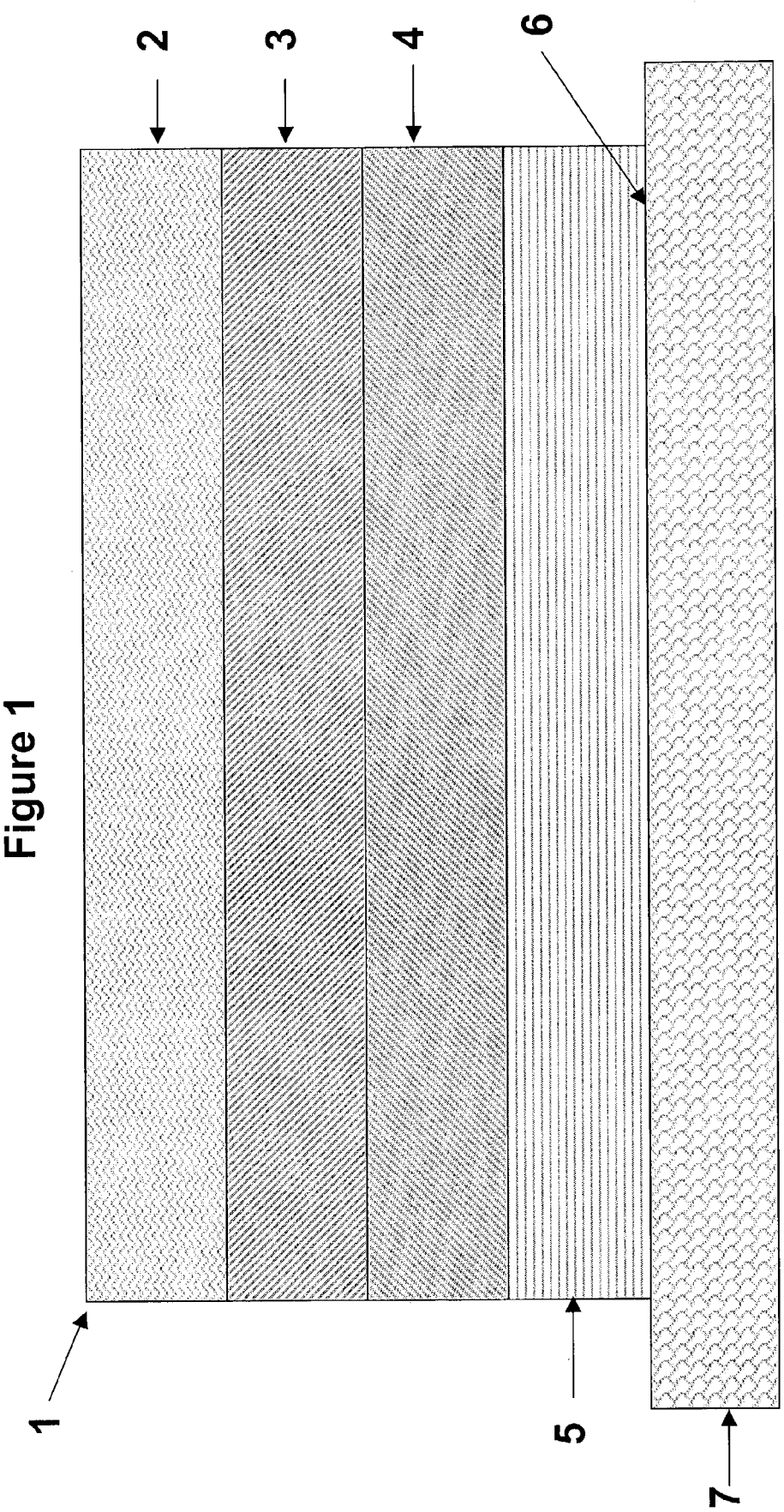
FIGS. 1 illustrates a cross-section through a schematic, perspective view of one embodiment of transdermal analgesic system according to this invention.

Overview:

The present invention is directed to a transdermal analgesic system having reduced potential for abuse, without diminishing the therapeutic or beneficial effects of the analgesic when the system is applied to the skin. In particular, the system of the present invention provides for the controlled release of the antagonist at a rate sufficient to provide an abuse limiting release rate ratio of the antagonist to the analgesic when the dosage form is subject to abuse, wherein the system provides for a substantially minimized/negligible skin sensitization response from antagonist exposure.

The practice of the present invention will employ, unless otherwise indicated, conventional methods used by those in pharmaceutical product development within those of skill of the art. Such techniques are explained fully in the literature. See, e.g., Gale, R., Chandrasekaran, S. K., Swanson, D. and Wright, J., "Use of Osmotically Active Therapeutic Agents in Monolithic Systems" J. Membrane Sci., 7 (1980), 319-331; Patini, G. A. and Chein, Y. W., Swarbrick, J. and Boylan, J. C., eds, Encyclopedia of Pharmaceutical Technology, New York: Marcel Dekker, Inc., 1999 and Gale, R., Hunt, J. and Prevo, M., Mathiowitz, E., ed, Encyclopedia of Controlled Drug Delivery Patches, Passive, New York: J Wiley & Sons, Inc, 1999. All patents, patent applications, and publications mentioned herein, whether supra or infra, are hereby incorporated by reference in their entirety.

Definitions:

In describing and claiming the present invention, the following terminology will be used in accordance with the definitions set out below.

The singular forms "a," "an" and "the" include plural referents unless the context clearly dictates otherwise. Thus, for example, reference to "a polymer" includes a single polymer as well as a mixture of two or more different polymers, reference to "a permeation enhancer" includes a single permeation enhancer as well as two or more different permeation enhancer in combination, and the like.

As used herein, the terms "analgesic" and "drug" are used interchangeably and refer to fentanyl and an analog of fentanyl. As used herein, the term "an analog of fentanyl" (hereafter referred to as "analog") refers to extremely potent and effective analgesics such alfentanil, carfentanil, lofentanil, remifentanil, sufentanil, trefentanil, and the like.

As used herein, the term "substantially prevents release of the antagonist from the system" implies a transdermal analgesic system wherein minimal amount of antagonist is released from the system upon casual contact or incidental exposure to water, such that there is minimal antagonist skin contact, thus substantially minimizing skin sensitization response from antagonist exposure.

As used herein, the term "incidental exposure to water" refers to short-term exposure to high humidity or brief exposure to liquid water, such as during showering, sweat, and the like.

As used herein, the term "subsaturated system" refers to system wherein the concentration of the analgesic is below its solubility limit. The analgesic reservoir comprises a single phase polymeric composition, free of undissolved components, wherein the analgesic and all other components are present at concentrations no greater than, and preferably less than, their saturation concentrations in the reservoir.

As used herein, the term "single phase polymeric composition" refers to a composition in which the analgesic and all other components are solubilized in a polymer and are present at concentrations no greater than, and preferably less than, their saturation concentrations in the reservoir such that there are no undissolved components present in the composition over a substantial portion of the administration period; wherein all the components in combination with the polymer form a single phase.

As used herein, the term "component" refers to an element within the analgesic reservoir, including, but not limited to, an analgesic as defined above, additives, permeation enhancers, stabilizers, dyes, diluents, plasticizer, tackifying agent, pigments, carriers, inert fillers, antioxidants, excipients, gelling agents, anti-irritants, vasoconstrictors and the like.

As used herein, an "analgesic release controlling means" refers to a means to modulate the release rate of the analgesic, such as rate control membranes generally known in the art.

As used herein, the term "antagonist release controlling means" refers to a means to control the antagonist release rate and substantially minimizing skin sensitization response from antagonist exposure. The antagonist release controlling means modulates the ingress of solvent in to the antagonist reservoir, thus modulating the release of the antagonist during abuse while permitting the release of the antagonist at a rate sufficient to inhibit abuse. The antagonist release controlling means include physical means such as a layer, a membrane, a film, a coating, a sheet, a deposit, including but not limited to, a rate control layer, a rate control membrane, a porous or a microporous membrane, an impermeable film wherein the release is controlled through the edge of the patch. The antagonist release controlling means also include chemical means and may be osmotically driven, concentration dependent, or may depend on the size and characteristics of the materials forming the antagonist release controlling means. In certain embodiments, the antagonist rate controlling means is incorporated within the antagonist reservoir where the rate of release is governed by the osmotic bursting mechanism cited in Gale, et al., (Gale, R., Chandrasekaran, S. K., Swanson, D. and Wright, J., "Use of Osmotically Active Therapeutic Agents in Monolithic Systems", J. Membrane Sci., 7 (1980), 319-331). The release rate of the antagonist is controlled by factors such as the amount of antagonist within the antagonist reservoir, the antagonist particle size, antagonist salt osmotic pressure, and physical characteristics of the polymer matrix of the antagonist reservoir.

The "DURAGESIC® fentanyl patch" is used interchangeably with "DUROGESIC™ fentanyl patch" and refers to a fentanyl patch as discussed above (see also Physicians Desk Reference, 56th Edition, 2002, pages 1786-1789).

As used herein, the term "abuse of a transdermal analgesic system" refers to the use of a transdermal analgesic system other than as indicated by the product labeling, including tampering or misusing the system, subjecting the system to diversion, ingestion or substantial immersion of the system in a solvent for intravenous administration, buccal administration, and the like.

As used herein, the term "$C_{max}$ (ng/ml)" refers to the peak blood, plasma or serum concentration of the analgesic, i.e., fentanyl or the analog thereof.

As used herein, the term "standardized $C_{max}$ (ng/ml-cm$^2$)" refers to the $C_{max}$ (ng/ml) per unit area (cm$^2$) of the active analgesic delivery area of the system, e.g., the area of the analgesic reservoir.

As used herein, the term "normalized $C_{max}$ (ng/ml-(mg/h))" refers to the $C_{max}$ (ng/ml) divided by the rate of the analgesic administered (mg/h).

As used herein, the term "steady state analgesic flux" refers to the analgesic flux (in vitro and in vivo) in the range of 1 to 20 μg/h-cm$^2$ over a substantial portion of the administration period.

As used herein, the term "bioavailability", refers to the rate and extent to which the active ingredient or active moiety is absorbed from a drug product and becomes available at the site of action. The rate and extent are established by the pharmacokinetic-parameters, such as, the area under the blood, plasma or serum drug concentration-time curve (AUC) and the peak, plasma or serum concentration ($C_{max}$) of the drug.

Two different products are considered to be "bioequivalent" if they produce substantially the same pharmacokinetic effects when studied under similar experimental conditions. Bioequivalence may be demonstrated through several in vivo and in vitro methods. These methods, in descending order of preference, include pharmacokinetic, pharmacodynamic, clinical and in vitro studies. In particular, bioequivalence is demonstrated using pharmacokinetic measures such as the area under the blood, plasma or serum drug concentration-time curve (AUC) and the peak blood, plasma or serum concentration ($C_{max}$) of the drug, using statistical criteria as described in greater detail hereinafter.

Two different products are considered to be "pharmacologically equivalent" if they produce substantially the same therapeutic effects when studied under similar experimental conditions, as demonstrated through several in vivo and in vitro methods as described in greater detail hereinafter. Therapeutic effects depend on various factors, such as, potency of the drug, the solubility and diffusivity of the drug in the skin, thickness of the skin, concentration of the drug within the skin application site, concentration of the drug in the drug reservoir, and the like, as described in greater detail hereinafter. In general, pharmacological equivalence is demonstrated using measures such as the peak blood, plasma or serum concentration of the drug normalized for the rate of drug administered (i.e. normalized $C_{max}$ as defined above) and the peak blood, plasma or serum concentration of the drug standardized per unit area of the active drug delivery area of the system (i.e. standardized $C_{max}$ as defined above).

When comparing two different products whose drug administration rate is proportional to the size of the transdermal analgesic system, bioequivalence or pharmacological equivalence may be established either by normalizing the peak blood, plasma or serum concentration of the drug ($C_{max}$) for the rate of drug administered (normalized $C_{max}$), or by standardizing the peak blood, plasma or serum concentration of the drug ($C_{max}$) per unit area of the active drug delivery area of the system (standardized $C_{max}$). However, when comparing two different products having different drug administration rate per unit area, it is necessary to normalize the peak blood, plasma or serum concentration of the drug ($C_{max}$) on the basis of the rate of drug administered to establish bioequivalence or pharmacological equivalence.

Modes of Carrying Out the Invention

The present invention provides an analgesic system for transdermal delivery of fentanyl and analogs thereof for analgetic purposes, to a subject through intact skin over an extended period of time, the system having reduced potential for abuse and a substantially minimized/negligible skin sensitization response from antagonist exposure. In particular, the transdermal analgesic system of the present invention provides for the controlled release of the antagonist at a rate sufficient to provide an abuse limiting release rate ratio of the antagonist to the analgesic when the dosage form is subject to abuse. In this regard, the transdermal analgesic system of the invention provides release of the antagonist at a rate sufficient to block the opioid effects of the analgesic during abuse situations.

Figure 2:
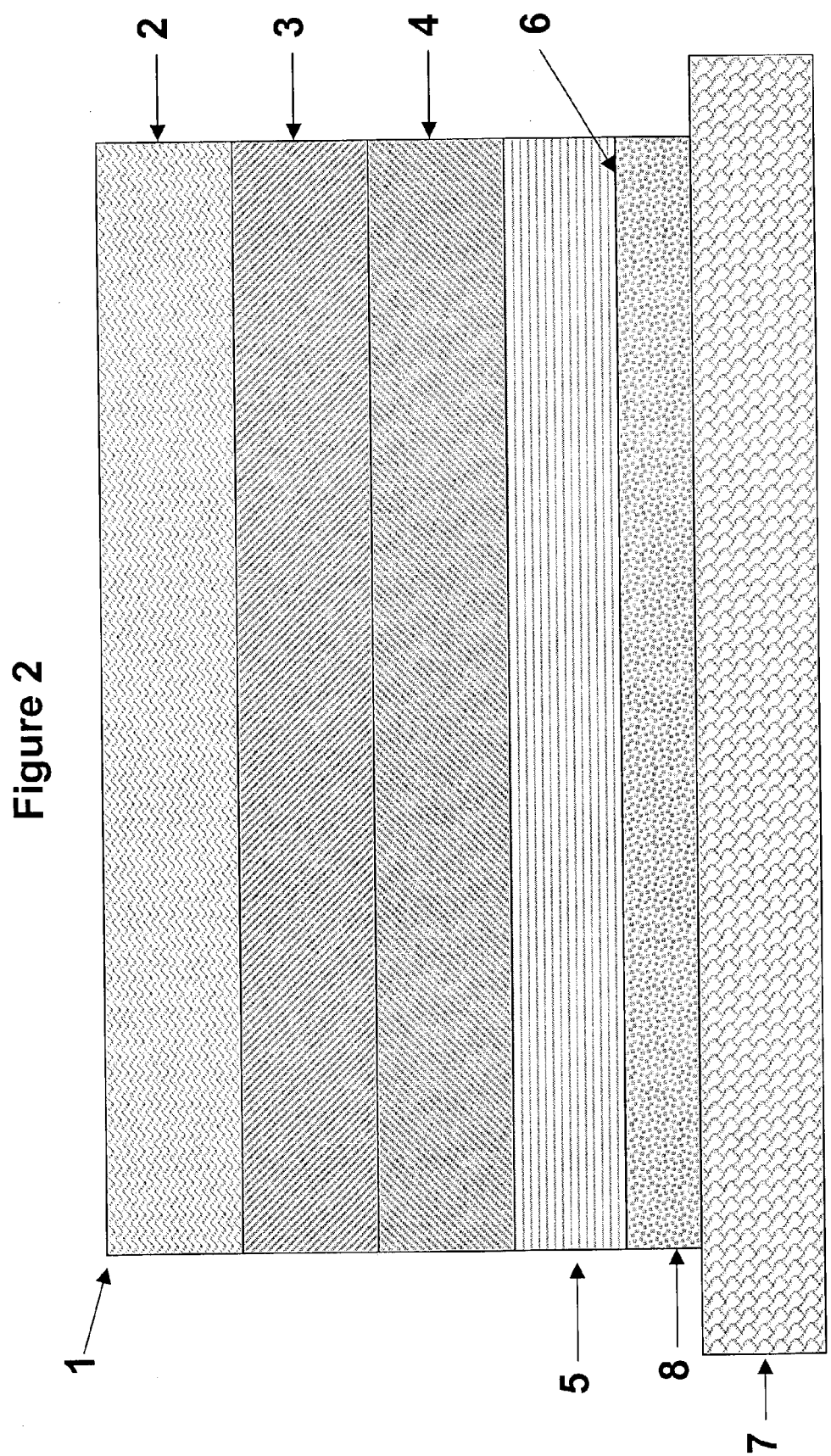
FIG. 2 illustrates a cross-section view through another embodiment of this invention.

Referring now to FIGS. 1-4 a preferred embodiment of the transdermal analgesic system according to this invention comprises a patch 1, an antagonist release controlling means 2, an antagonist reservoir 3 wherein the skin distal surface of the antagonist reservoir is disposed on the antagonist release controlling means 2, an impermeable barrier layer 4 wherein the antagonist reservoir 3 is disposed on the skin distal surface of the barrier layer 4, an analgesic reservoir 5 disposed on the skin proximal surface of the barrier layer 4, wherein at least the skin contacting surface 6 of the analgesic reservoir 5 is adhesive, and a peelable protective layer 7. In preferred embodiments, the analgesic reservoir 5 is formed from a pharmaceutically acceptable adhesive. Referring now to FIG. 2, the transdermal analgesic system of the invention further comprises an analgesic rate controlling means 8 disposed on the skin contacting surface of the analgesic reservoir 6, wherein at least the skin contacting surface of the analgesic rate controlling means 8 is adhesive.

Figure 3:
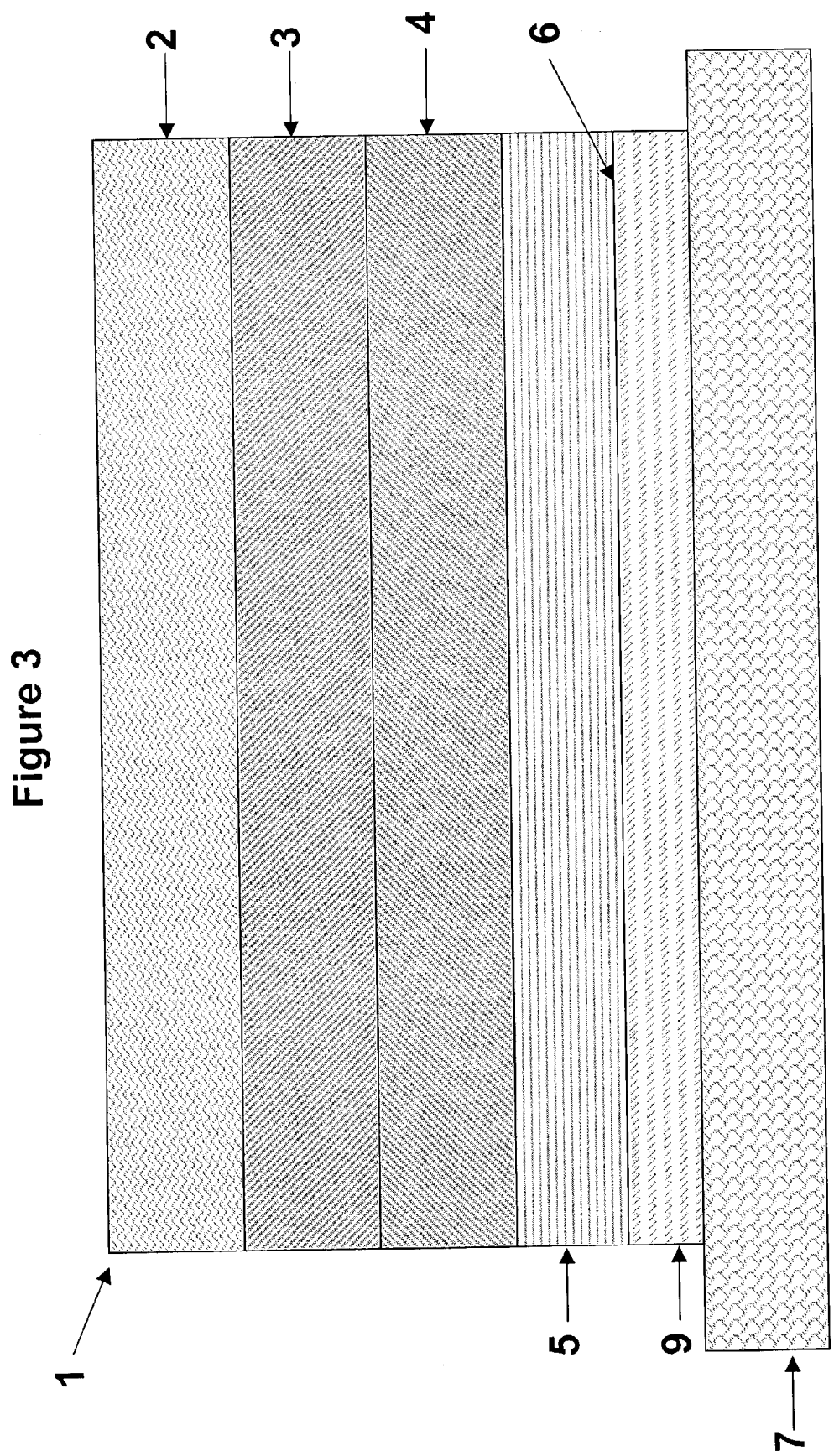
FIG. 3 illustrates a cross-section view through another embodiment of this invention.
Figure 4:
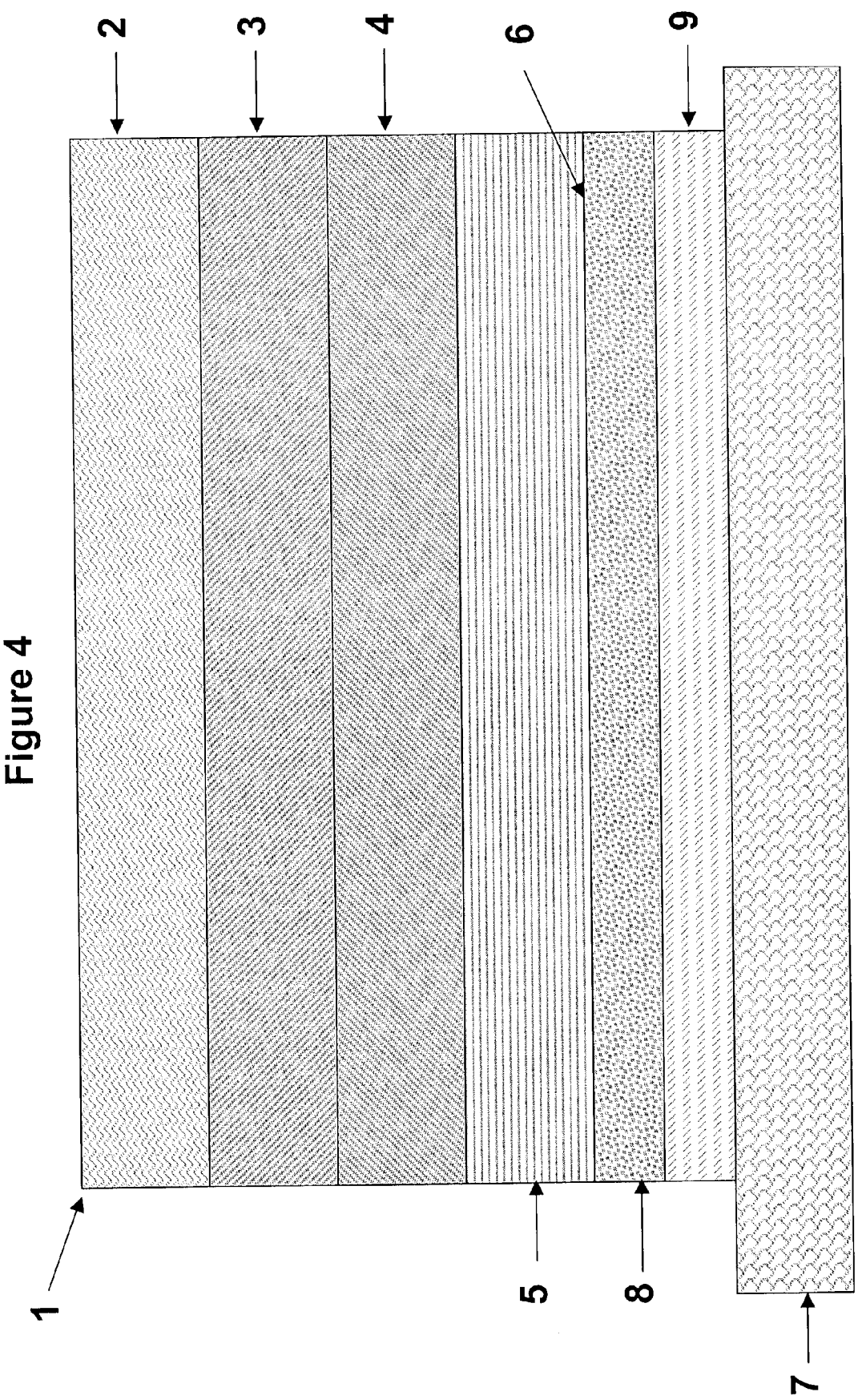
FIG. 4 illustrates a cross-section view through another embodiment of this invention.

Referring now to FIG. 3, the analgesic reservoir 5 is formed from a material that does not have adequate adhesive properties. In this embodiment of a transdermal analgesic system of the invention comprises a patch 1, wherein the skin-contacting surface of the analgesic reservoir 6 may be formulated with an adhesive coating 9. The analgesic reservoir 5 is a single phase polymeric composition in which the analgesic and all other components are present at concentrations no greater than, and probably less than, their saturation concentrations in the analgesic reservoir 5. This produces a composition in which no undissolved components are present. Referring now to FIG. 4, the transdermal analgesic system of the invention further comprises an analgesic rate controlling means 8 disposed on the skin contacting surface of the analgesic reservoir 6, wherein at least the skin contacting surface of the analgesic rate controlling means 8 is adhesive.

The antagonist release controlling means 2 substantially prevents release of the antagonist from the system upon securing the system to a human patient for a period of up to about 7 days; substantially minimizing skin sensitization response from antagonist exposure; and provides release of the antagonist at a rate sufficient to provide an abuse limiting release rate ratio of the antagonist to the analgesic when the dosage form is subject to abuse, e.g., upon ingestion or substantial immersion of the system in the solvent. The antagonist release controlling means 2 modulates the ingress of water/solvent in to the antagonist reservoir, thus modulating the release of the antagonist during abuse while permitting the release of an antagonist at a rate sufficient to limit abuse. The antagonist release controlling means include physical means such as a membrane, a film, a coating, a sheet, a deposit, including but not limited to, a rate control membrane, a porous or a microporous membrane, an impermeable film wherein the release is controlled through the edge of the patch. The antagonist release controlling means also include chemical means and may be osmotically driven, concentration dependent, or may depend on the size and characteristics of the materials forming the antagonist release controlling means. In certain embodiments, the antagonist rate controlling means is incorporated within the antagonist reservoir where the rate of release is governed by the osmotic bursting mechanism cited in Gale, et al. The release rate of the antagonist is controlled by factors such as the amount of antagonist within the antagonist reservoir, the antagonist particle size, antagonist salt osmotic pressure, and physical characteristics of the polymer matrix of the antagonist reservoir.

In preferred embodiments, the antagonist release controlling means 2 may be a monolithic or a multilaminate layer comprising a material that substantially prevents release of the antagonist from the antagonist reservoir during incidental exposure to moisture. In particular, the antagonist release controlling means 2 comprises a breathable or occlusive material comprising fabric, porous, microporous, spun-bonded, spun laced, track etched, or impermeable material comprising polyvinyl acetate, polyvinylidene chloride, polyethylene, polypropylene, polyurethane, polyester, ethylene vinyl acetate (EVA), polyethylene terephthalate, polybutylene terephthalate, rayon (synthetic textile fibers produced by forcing a cellulose solution through fine spinnerets and solidifying the resulting filaments), wood-pulp, spun laced polyester, coated paper products, aluminum sheet, and the like, and a combination thereof. In preferred embodiments, antagonist release controlling means comprises low density polyethylene (LDPE) materials, medium density polyethylene (MDPE) materials or high density polyethylene (HDPE) materials, and the like. In preferred embodiments, the release controlling means is a single LDPE layer. In additional preferred embodiments, the antagonist release controlling means comprises a microporous layer selected from the group consisting of Solupor microporous ultra high density polyethylene (UHDPE) materials/film (Solupor™ manufactured by DSM Desotech, Denmark), microporous polypropylene (Celgard™ film manufactured by Celgard, Inc., Charlotte, N.C.), RoTrac Polyester Capillary Pore Membranes (OYPHEN GmbH, Germany), spun laced polyester, polypropylene or polyethylene. The microporous layer can be further modified with surfactants such as Pluracare polyethylene oxide-polypropylene oxide block copolymers (BASF, Wyandotte, Mich.) or hydrophilic polymers such as polyvinylpyrrolidone to provide additional control over the antagonist release as discussed in greater detail below.

The antagonist release controlling means has a thickness of about 0.012 mm (0.5 mil) to about 0.125 mm (5 mil); preferably 0.025 mm (1 mil) to about 0.1 mm (4 mil); more preferably 0.0375 mm (1.5 mil) to about 0.0875 mm (3.5 mil); and even more preferably 0.05 mm (2 mil) to about 0.0625 mm (2.5 mil).

The transdermal analgesic system according to this invention comprises an antagonist reservoir 3, wherein the skin distal surface of the antagonist reservoir is disposed on the antagonist release controlling means 2. The antagonist reservoir may be same size as the other layers of the patch or the antagonist may be inset from the edge of the die cut patch. The antagonist reservoir 3 may be formed from standard materials as known in the art. For example, the antagonist reservoir is formed from a hydrophobic, a lipophilic and/or a non-polar polymeric material, such as, ethyleneoctene copolymers, ethylene-vinyl acetate copolymer (EVA), low density polyethylene (LDPE), high density polyethylene (HDPE), medium density polyethylene (MDPE), styrenic block copolymer thermoplastic elastomers, and the like. In preferred embodiments, the antagonist reservoir 3 is formed from EVA, ethyleneoctene copolymers, as described in greater detail below.

As discussed above, the antagonist reservoir 3 comprises an antagonist in a substantially non-releasable form when the transdermal analgesic system is used as recommended and/or during incidental exposure to water (e.g., sweat, showering, high humidity etc.), the antagonist being releasable from the analgesic system when analgesic system is abused, i.e. upon being ingested or substantially immersed in a solvent. Preferably, the antagonist is present in a form that is substantially impermeable to the skin to which the transdermal analgesic system of the invention is to be applied. The antagonist reservoir comprises an antagonist dispersed within a polymer, wherein the antagonist is substantially insoluble in the antagonist reservoir polymer. In preferred embodiments, the antagonist is present as a salt, preferably as a hydrochloride salt of an antagonist base. The low solubility of the antagonist in skin and polymer has several advantages, substantially minimizing undesirable interactions between the antagonist and the analgesic, improved stability/shelf life of the transdermal analgesic system, and substantially minimizing skin sensitization response from antagonist exposure.

In certain embodiments, the antagonist is dispersed in a matrix comprising a polymeric material which substantially prevents release of the antagonist, preferably a thermoformable material; or the antagonist is complexed with an ionic resin. In additional embodiments, the antagonist reservoir comprises the antagonist in a multiparticulate form, wherein each particle is individually coated with a polymeric material which substantially prevents release of the antagonist, wherein the polymeric material is preferably a thermoformable material. In additional embodiments, the antagonist reservoir comprises beads coated with the antagonist, wherein the beads may be formed from glass or an inert or non-dissolvable polymer, and further wherein the coated beads are optionally coated with or dispersed in a polymeric material which substantially prevents release of the antagonist, wherein the polymeric material is preferably a thermoformable material. The antagonist is selected from a group consisting of naltrexone, methyinaltrexone, naloxone, nalbuphine, nalorphine, nalorphine dinicotinate, nalmefene, nadide, levallorphan, cyclozocine and pharmaceutically acceptable salts thereof. Preferably, the antagonist is present as a salt.

As discussed above, the antagonist reservoir comprises the antagonist dispersed within a polymer. Preferably, the antagonist is dispersed in a matrix comprising a thermoformable material that substantially prevents release of the antagonist. Alternatively, the antagonist is present in a multiparticulate form, wherein each particle is individually coated with a polymeric material that substantially prevents release of the antagonist. Preferably, the polymeric material which substantially prevents release of the antagonist is hydrophobic—i.e., substantially prevents release of the antagonist during normal use, minimizes the amount of antagonist during incidental/casual exposure to solvents (moisture, e.g., sweat, during a shower), and when the dosage form is subject to abuse, e.g., upon ingestion or immersion in a solvent, releases the antagonist in abuse limiting amounts. Preferably, the polymeric material has a low melting point to allow processing of the antagonist in solid phase and to prevent degradation of the antagonist. Examples of a polymeric material which substantially prevents release of the antagonist include, but are not limited to, polyethylene, polyoctene, polyvinyl acetate, polymethyl acrylate, polymethyl acrylate, polyethyl acrylate, polystyrene polymers and copolymers and mixtures thereof; polystyrene copolymers such as styrenic block copolymers (SIS, SBS, SEBS), ethylene copolymers such as polyethyleneoctene copolymers, ethylene-vinyl acetate copolymer (EVA), ethylenemethyl acrylate copolymers (EMA), ethylene-acrylic acid copolymer, ethylene-ethylacrylate copolymer, and the like, and combinations thereof.

In additional embodiments, the antagonist is complexed with an ionic resin. Examples of ionic resins include, but are not limited to sulfonated polystyrene resins, and the like. Preferably the resin contains a sulfonic acid functionality which when neutralized with the antagonist base forms the sulfonate salt of the antagonist.

In additional embodiments, the antagonist reservoir comprises beads coated with the antagonist, wherein the spheres or beads may be formed from glass, metals or an inert or non-dissolvable polymer, and further wherein the coated beads are optionally coated with or dispersed in a polymeric material which substantially prevents release of the antagonist, as described above. The beads may be in any shape, size or form, but are preferably small sized, preferably less than 10 microns. Examples of an inert or non-dissolvable polymer include, but are not limited to polymethylmethacrylate, polycarbonate and polystyrene.

The antagonist reservoir 3 comprises an amount of the antagonist sufficient to counter analgesic and euphoric effects of the analgesic when the transdermal analgesic system is abused. Preferably, the antagonist reservoir comprises about 0.2 to about 15 mg/cm$^2$ of the antagonist; more preferably about 0.6 to about 5 mg/cm$^2$ of the antagonist; and even more preferably about 0.75 to about 1.5 mg/cm$^2$ of the antagonist. Preferably, the antagonist reservoir comprises about 20 to about 70 wt % of the antagonist; more preferably about 40 to about 65 wt % of the antagonist; even more preferably about 50 to about 60 wt % of the antagonist; and even more preferably about 52 to about 56 wt % of the antagonist. In preferred embodiments, the antagonist is in the salt form and the preferred antagonists are naltrexone, methylnaltrexone, naloxone, nalbuphine, nalorphine, nalorphine dinicotinate, nalmefene, nadide, levallorphan and cyclozocine.

Preferably, the antagonist is substantially insoluble in the polymer forming the antagonist reservoir 3. In particular, the material forming the antagonist reservoir 3 has a solubility for the antagonist of about 0 wt % to about 1 wt % of the total polymer composition; more preferably about 0 wt % to about 0.8 wt %; and even more preferably about 0 wt % to about 0.5 wt % of the total polymer composition. The antagonist reservoir 3, has a thickness of about 0.0125 mm (0.5 mil) to about 0.1 mm (4 mil); preferably about 0.015 mm (0.6 mil) to about 0.0875 mm (3.5 mil); more preferably 0.025 mm (1 mil) to about 0.08 mm (3.3 mil); and even more preferably about 0.025 mm (1 mil) to about 0.075 (3 mil).

The transdermal analgesic system according to this invention comprises an impermeable barrier layer 4 wherein the antagonist reservoir 3 is disposed on the skin distal surface of the barrier layer 4, and an analgesic reservoir 5 is disposed on the skin proximal surface of the barrier layer 4. The barrier layer 4 is impermeable to the antagonist and the analgesic; and comprises a material which is insoluble in water, alcohol and organic solvents. The barrier layer 4 comprises a polymer such as polyolefin laminates (Dow Chemical, Midland, Mich.), acrylonitrile copolymer films (BAREX, BP Chemicals, KoIn, Germany), polyethylnapthalene (PEN), polyethylene terephthalate (PET), polyimide, polyurethane, polyethylene, metallized films and glass coated films where these films can include ethylene copolymers such as ethylene-vinyl acetate copolymer (EVA), and combinations thereof. In preferred embodiments, the barrier layer comprises polyester such as PET laminated to a polymer such as polyurethane, polyethylene, and ethylene copolymers. In preferred embodiments, the barrier layer comprises polyester such as PET laminated to ethylene copolymers such as ethylene-vinyl acetate copolymer (EVA). The barrier layer as a multilaminate layer has a thickness of about 0.075 mm (0.3 mil) to about 0.125 mm (5 mil); preferably 0.025 mm (1 mil) to about 0.1 mm (4 mil); more preferably 0.0625 mm (1.5 mil) to about 0.0875 mm (3.5 mil); and even more preferably 0.025 mm (1 mil) to about 0.05 mm (2 mil). The polyethylene or EVA laminated layer of the preferred PET-PE laminates improves the adhesion of the antagonist reservoir to the backing, and serves to prevent the facile removal of the antagonist reservoir from the system by the abuser.

The analgesic reservoir 5 is disposed on the skin proximal surface of the barrier layer 4, wherein at least the skin contacting surface 6 of the analgesic reservoir 5 is adhesive. The analgesic reservoir 5 may be formed from standard materials as known in the art. For example, the analgesic reservoir is formed from hydrophobic and/or lipophilic polymeric material, such as, hydrophobic polyurethane, ethylene-vinyl acetate copolymer (EVA) and the like. In preferred embodiments, the analgesic reservoir 5 is formed from a pharmaceutically acceptable pressure sensitive adhesive, preferably a polyacrylate or a styrenic block copolymer-based adhesive, as described in greater detail below. In preferred embodiments, the pressure sensitive adhesive has zero shear viscosity greater than $1\text{-}10^9$ poise at 25° centigrade, as determined by the principle of time-temperature superpositioning of dynamic viscosity curves at various temperatures. This requirement serves to prevent adhesive cold flow, and the corresponding increased likelihood for analgesic-antagonist exchange at the edge of the system.

The adhesive analgesic reservoir 5 or the adhesive coating 9 is formed from standard pressure sensitive adhesives known in the art. Examples of pressure sensitive adhesives include, but are not limited to, polyacrylates, polysiloxanes, polyisobutylene (PIB), polyisoprene, polybutadiene, styrenic block polymers, and the like. Examples of styrenic block copolymer-based adhesives include, but are not limited to, styrene-isoprene-styrene block copolymer (SIS), styrene-butadiene-styrene copolymer (SBS), styrene-ethylenebutene-styrene copolymers (SEBS), and di-block analogs thereof.

The acrylic polymers are comprised of a copolymer or terpolymer comprising at least two or more exemplary components selected from the group comprising acrylic acids, alkyl acrylates, methacrylates, copolymerizable secondary monomers or monomers with functional groups. Examples of monomers include, but are not limited to, acrylic acid, methacrylic acid, methoxyethyl acrylate, ethyl acrylate, butyl acrylate, butyl methacrylate, hexyl acrylate, hexyl methacrylate, 2-ethylbutyl acrylate, 2-ethylbutyl methacrylate, isooctyl acrylate, isooctyl methacrylate, 2-ethylhexyl acrylate, 2-ethylhexyl methacrylate, decyl acrylate, decyl methacrylate, dodecyl acrylate, dodecyl methacrylate, tridecyl acrylate, tridecyl methacrylate, hydroxyethyl acrylate, hydroxypropyl acrylate, acrylamide, dimethylacrylamide, acrylonitrile, dimethylaminoethyl acrylate, dimethylaminoethyl methacrylate, tert-butylaminoethyl acrylate, tert-butylaminoethyl methacrylate, methoxyethyl acrylate, methoxyethyl methacrylate, and the like. Additional examples of appropriate acrylic adhesives suitable in the practice of the invention are described in Satas, "Acrylic Adhesives," Handbook of Pressure-Sensitive Adhesive Technology, 2nd ed., pp. 396-456 (D. Satas, ed.), Van Nostrand Reinhold, New York (1989). The acrylic adhesives are commercially available (National Starch and Chemical Corporation, Bridgewater, N.J.; Solutia, Mass.). Further examples of polyacrylate-based adhesives are as follows, identified as product numbers, manufactured by National Starch (Product Bulletin, 2000): 87-4098, 87-2287,87-4287, 87-5216, 87-2051, 87-2052, 87-2054, 87-2196, 87-9259,87-9261, 87-2979, 87-2510, 87-2353, 87-2100, 87-2852, 87-2074, 87-2258, 87-9085, 87-9301 and 87-5298.

The acrylic polymers comprise cross-linked and non-cross-linked polymers. The polymers are cross-linked by known methods to provide the desired polymers. In preferred embodiments, the adhesive is a polyacrylate adhesive having a glass transition temperature (Tg) less than −10° C., more preferably having a Tg of about −20° C. to about −35° C. The molecular weight of the polyacrylate adhesive, expressed as weight average (MW), generally ranges from 25,000 to 10,000,000, preferably from 50,000 to about 3,000,000 and more preferably from 100,000 to 1,000,000 prior to any cross-linking reactions. Upon cross-linking the MW approaches infinity, as known to those involved in the art of polymer chemistry.

The transdermal analgesic systems comprise analgesic reservoirs comprising a component, including an analgesic at concentration greater than, equal to, or less than saturation concentration. As discussed above, in preferred embodiments the analgesic reservoir 5, comprises a single phase polymeric composition, free of undissolved components, containing an amount of the analgesic sufficient to induce and maintain analgesia in a human for at least three days. The analgesic is selected from a group consisting of fentanyl and analogs thereof, such as, alfentanil, carfentanil, lofentanil, remifentanil, sufentanil, trefentanil, and the like. In preferred embodiments, the analgesic reservoir comprises about 0.05 to about 1.75 mg/cm$^2$ of analgesic; preferably about 0.07 to about 1.50 mg/cm$^2$ of analgesic; preferably about 0.08 to about 1.25 mg/cm$^2$ of analgesic; more preferably about 0.09 to about 1.0 mg/cm$^2$ of analgesic; more preferably about 0.1 to about 0.75 mg/cm$^2$ of analgesic; and even more preferably about 0.12 to about 0.5 mg/cm$^2$ of analgesic. The analgesic should be soluble in the polymer forming reservoir 3 in a form that is as discussed below. In preferred embodiments, the analgesic is in the base form and the preferred analgesics are fentanyl or sufentanil. In particularly preferred embodiments, the analgesic reservoir comprises about 0.05 to about 1.75 mg/cm$^2$ of fentanyl; preferably about 0.07 to about 1.50 mg/cm$^2$ of fentanyl; preferably about 0.08 to about 1.25 mg/cm$^2$ of fentanyl; more preferably about 0.09 to about 1.0 mg/cm$^2$ of fentanyl; more preferably about 0.1 to about 0.75 mg/cm$^2$ of fentanyl; and even more preferably about 0.12 to about 0.5 mg/cm$^2$ of fentanyl; wherein fentanyl is in a base form and is completely dissolved. In additionally preferred embodiments, the analgesic reservoir comprises about 0.05 to about 1.75 mg/cm$^2$ of sufentanil; preferably about 0.07 to about 1.50 mg/cm$^2$ of sufentanil; preferably about 0.08 to about 1.25 mg/cm$^2$ of sufentanil; more preferably about 0.09 to about 1.0 mg/cm$^2$ of sufentanil; more preferably about 0.1 to about 0.75 mg/cm$^2$ of sufentanil; and more preferably about 0.12 to about 0.5 mg/cm$^2$ of sufentanil; wherein sufentanil is in a base form and is completely dissolved.

The material forming the analgesic reservoir 5 has a solubility for the analgesic of about 1 wt % to about 25 wt % of the total polymer composition; preferably about 2 wt % to about 15 wt %; more preferably about 4 wt % to about 12 wt % of the total polymer composition; and even more preferably about 6 wt % to about 10 wt % of the total polymer composition. The reservoir 5, with or without the adhesive coating 9, has a thickness of about 0.0125 mm (0.5 mil) to about 0.1 mm (4 mil); preferably about 0.025 mm (1 mil) to about 0.0875 mm (3.5 mil); more preferably 0.0375 mm (1.5 mil) to about 0.075 mm (3 mil); and even more preferably about 0.04 mm (1.6 mil) to about 0.05 mm (2 mil). In preferred embodiments, the analgesic is fentanyl, preferably in the base form, wherein the material forming the reservoir 5 has a solubility for fentanyl of about 1 wt % to about 25 wt % of the total polymer composition; preferably about 3 wt % to about 15 wt %; more preferably about 5 wt % to about 12 wt %; and even more preferably about 7 wt % to about 10 wt % of the total polymer composition. The reservoir 5, with or without the adhesive coating 9, has a thickness of about 0.0125 mm (0.5 mil) to about 0.1 mm (4 mil); preferably about 0.025 mm (1 mil) to about 0.075 mm (3 mil); more preferably 0.0375 mm (1.5 mil) to about 0.0625 mm (2.5 mil); and even more preferably about 0.04 mm (1.6 mil) to about 0.05 mm (2 mil). In additionally preferred embodiments, the analgesic is sufentanil, preferably in the base form, wherein the material forming the reservoir 5 has a solubility for sufentanil of about 1 wt % to about 25 wt % of the total polymer composition; preferably about 3 wt % to about 15 wt %; more preferably about 5 wt % to about 12 wt %; and even more preferably about 7 wt % to about 10 wt % of the total polymer composition. The reservoir 5, with or without the adhesive coating 9, has a thickness of about 0.0125 mm (0.5 mil) to about 0.1 mm (4 mil); preferably about 0.025 mm (1 mil) to about 0.075 mm (3 mil); more preferably 0.0375 mm (1.5 mil) to about 0.0625 mm (2.5 mil); and even more preferably about 0.04 mm (1.6 mil) to about 0.05 mm (2 mil).

In additional embodiments, the analgesic reservoir 5 may optionally contain additional components such as, additives, permeation enhancers, stabilizers, dyes, diluents, plasticizer, tackifying agent, pigments, carriers, inert fillers, antioxidants, excipients, gelling agents, anti-irritants, vasoconstrictors and other materials as are generally known to the transdermal art, provided that such materials are present below saturation concentration in the reservoir.

Examples of permeation enhancers include, but are not limited to, fatty acid esters of glycerin, such as capric, caprylic, dodecyl, oleic acids; fatty acid esters of isosorbide, sucrose, polyethylene glycol; caproyl lactylic acid; laureth-2; laureth-2 acetate; laureth-2 benzoate; laureth-3 carboxylic acid; laureth-4; laureth-5 carboxylic acid; oleth-2; glyceryl pyroglutamate oleate; glyceryl oleate; N-lauroyl sarcosine; N-myristoyl sarcosine; N-octyl-2-pyrrolidone; lauraminopropionic acid; polypropylene glycol-4-laureth-2; polypropylene glycol-4-laureth-5dimethyl lauramide; lauramide diethanolamine (DEA). Preferred enhancers include, but are not limited to, lauryl pyroglutamate (LP), glyceryl monolaurate (GML), glyceryl monocaprylate, glyceryl monocaprate, glyceryl monooleate (GMO), and sorbitan monolaurate. Additional examples of suitable permeation enhancers are described, for example, in U.S. Pat. Nos. 5,785,991; 5,843, 468; 5,882,676; and 6,004,578.

In certain embodiments, the analgesic reservoir comprises diluent materials capable of reducing quick tack, increasing viscosity, and/or toughening the matrix structure, such as polymethyl methacrylate or polybutyl methacrylate (ELVACITE, manufactured by ICI Acrylics, e.g., ELVACITE 1010, ELVACITE 1020, ELVACITE 20), high molecular weight acrylates, i.e., acrylates having an average molecular weight of at least 500,000, and the like.

In certain embodiments, particularly with styrenic block copolymer adhesive systems, a plasticizer or tackifying agent is incorporated in the adhesive composition to improve the adhesive characteristics. Examples of suitable tackifying agents include, but are not limited to, aliphatic hydrocarbons; aromatic hydrocarbons; hydrogenated esters; polyterpenes; hydrogenated wood resins; tackifying resins such as ESCOREZ, aliphatic hydrocarbon resins made from cationic polymerization of petrochemical feedstocks or the thermal polymerization and subsequent hydrogenation of petrochemical feedstocks, rosin ester tackifiers, and the like; mineral oil and combinations thereof.

The tackifying agent employed should be compatible with the blend of polymers. For example, the styrenic block copolymers can be formulated with rubber compatible tackifying resins, end-block compatible resins such polymethyl styrene, or plasticizers such as mineral oil. Generally the polymer is about 5-50% of the total adhesive composition, the tackifier is about 30-85% of the total adhesive composition, and the mineral oil is about 2-40% of total adhesive composition.

The patch 1 further comprises an analgesic rate controlling means 8 disposed on the skin contacting surface of the analgesic reservoir 6, wherein at least the skin contacting surface of the analgesic rate controlling means 8 is adhesive. The analgesic rate controlling means 8 is made of a polymeric material such as ethylene-vinyl acetate (EVA), polyvinyl chloride (PVC), ethylene-ethyl acrylate copolymer, ethylene butylacrylate copolymer, polyisobutylene (PIB), polyethylene (PE) such as low density polyethylene (LDPE), medium density polyethylene (MDPE), high density polyethylene (HDPE), and the like, and a combination thereof; the polymeric materials may be plasticized. In preferred embodiments, the analgesic rate controlling means is adhered to the skin with an acrylic, silicone, or PIB adhesive material. The analgesic rate controlling means has a thickness of about 0.012 mm (0.5 mil) to about 0.125 mm (5 mil); preferably 0.025 mm (0.6 mil) to about 0.1 mm (4 mil); more preferably 0.0625 mm (0.8 mil) to about 0.0875 mm (3.5 mil).

The patch 1 further comprises a peelable protective layer 7. The protective layer 7 is made of a polymeric material that may be optionally metallized. Examples of the polymeric materials include, polypropylene, polystyrene, polyimide, polyethylene, polyethylene terephthalate, polybutylene terephthalate, paper, and the like, and a combination thereof. In preferred embodiments, the protective layer comprises a siliconized polyester sheet.

Figure 5:
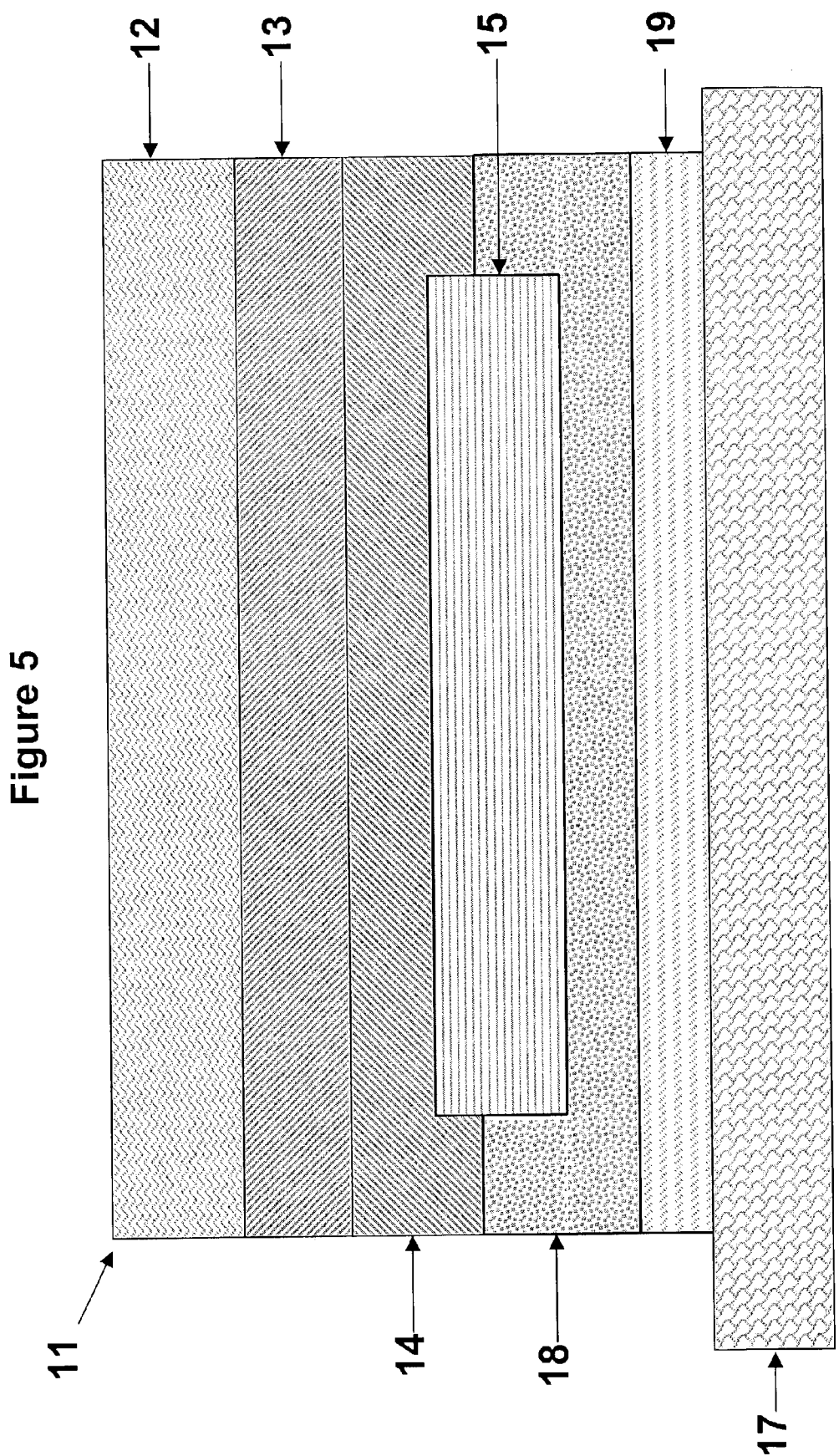
FIG. 5 illustrates a cross-section view through another embodiment of this invention.

Referring now to FIG. 5 a preferred embodiment of the transdermal analgesic system according to this invention comprises a patch 11, an antagonist release controlling means 12, an antagonist reservoir 13 wherein the skin distal surface of the antagonist reservoir is disposed on the antagonist release controlling means 12, an impermeable barrier layer 14 wherein the antagonist reservoir 13 is disposed on the skin distal surface of the barrier layer 14, a pouch formed from the impermeable barrier layer 14, an analgesic reservoir 15, an analgesic rate controlling means 18, and an amine resistant contact adhesive layer 19, covered by a peelable protective layer 17. The impermeable barrier layer 14 is configured to provide a central volume which contains an analgesic reservoir 15 in the form of a gel having dissolved and suspended analgesic therein. Although preferred embodiments of this invention utilize an amine resistant in-line adhesive as shown in FIG. 5, other means for maintaining the system on the skin can be employed. Such means include a peripheral ring of adhesive outside the path of analgesic from the system to the skin, in which case the adhesive need not be amine resistant. The use of adhesive overlays or other fastening means such as buckles, belts, and elastic arm bands is also contemplated. Elements 11, 12, 13, 14, 15, 16, 17, 18 and 19 may be made from materials similar to those used in the corresponding elements of FIGS. 1-4 whereas the analgesic reservoir 15 includes both aqueous and non-aqueous systems and is preferably an acrylic, silicone or polyisobutylene-based material, which may be plasticized and contain permeation enhancers, in which the analgesic is dissolved and dispersed. A general formulation for the barrier 13, the analgesic reservoir 15 and the analgesic rate controlling means of transdermal analgesic system illustrated in FIG. 5 is as described in U.S. Pat. No. 4,588,580 which is incorporated herein by reference.

A wide variety of materials which can be used for fabricating the various layers of the transdermal analgesic systems according to this invention have been described above. This invention therefore contemplates the use of materials other than those specifically disclosed herein, including those which may hereafter become known to the art to be capable of performing the necessary functions.

Administration of the Drug

The present invention provides a transdermal analgesic system having reduced potential for abuse, without diminishing the therapeutic or beneficial effects of the analgesic when the system is applied to the skin. As discussed above, the transdermal analgesic system comprises an antagonist in a substantially non-releasable form when the system is used as recommended and/or during incidental exposure to water, the antagonist being releasable from system when the analgesic system is abused, i.e. upon being ingested or substantially immersed in a solvent. In particular, the system of the present invention provides for the controlled release of the antagonist at a rate sufficient to provide an abuse limiting release rate ratio of the antagonist to the analgesic when the dosage form is subject to abuse. The transdermal analgesic system substantially prevents release of the antagonist from the system upon securing the system to a human patient for a period of up to about 7 days. Additionally the system of the invention provides release of the antagonist at a rate sufficient to provide an abuse limiting release rate ratio of the antagonist to the analgesic when the dosage form is subject to abuse, e.g., upon ingestion or substantial immersion of the system in the solvent, as described in greater detail hereinafter.

On application to the skin, the analgesic in the analgesic reservoir (5, 15) of the transdermal system (1, 11) diffuses into the skin where it is absorbed into the bloodstream to produce a systemic analgetic effect. The onset of analgesia depends on various factors, such as, potency of the analgesic, the solubility and diffusivity of the analgesic in the skin, thickness of the skin, concentration of the analgesic within the skin application site, concentration of the analgesic in the analgesic reservoir, and the like (see e.g., U.S. Pat. No. 4,588,580 for a discussion of relative permeabilities and potencies of fentanyl and analogs thereof). The concentration of the analgesic within the skin application sites are also significant in establishing an upper limit on the size of the transdermal analgesic system and, conversely, the lower limit on the usable administration rate, as described in co-pending international Application No. WO 200274286, which is incorporated in its entirety herein by reference.

When continuous analgesia is desired the depleted transdermal analgesic system would be removed and a fresh system is applied to a new location. For example, the transdermal analgesic system would be sequentially removed and replaced with a fresh system at the end of the administration period to provide relief from chronic pain. Since absorption of the analgesic from the fresh transdermal analgesic system into the new application area usually occurs at substantially the same rate as absorption by the body of the residual analgesic within the previous application site of the transdermal analgesic system, blood levels will remain substantially constant. Additionally, it is contemplated that doses may be increased over time and that concurrent use of other analgesics may occur to deal with breakthrough pain.

In preferred embodiments, the invention provides for a transdermal analgesic system exhibiting a normalized $C_{max}$ ranging from about 3.3 to about 82.5 ng/ml-(mg/h), preferably about 6.6 to about 50 ng/ml-(mg/h), more preferably about 13 to about 40 ng/ml-(mg/h), and even more preferably from about 20 to about 35 ng/ml-(mg/h); and a standardized $C_{max}$ ranging from about 0.001 to about 0.2 ng/ml-cm², preferably about 0.005 to about 0.15 ng/ml-cm², more preferably about 0.008 to about 0.1 ng/ml-cm², and even more preferably from about 0.01 to about 0.08 ng/ml-cm². The transdermal analgesic system comprises a transdermal analgesic system of about 0.5 to about 150 cm²; preferably about 2 to about 100 cm²; more preferably about 4 to about 50 cm², and even more preferably about 10 to about 20 cm². On administration over skin the transdermal analgesic system exhibits a steady state analgesic flux of about 0.1 to about 20 µg/h-cm²; preferably about 0.75 to about 10 µg/h-cm²; preferably about 1 to about 8 µg/h-cm²; more preferably about 1.5 to about 5 µg/h-cm²; more preferably about 2 to about 3 µg/h-cm², and even more preferably about 1 to about 2.5 µg/h-cm². Steady-state administration rates obtainable according to this invention range from about 0.1 to about 500 µg/h; preferably about 1 to about 300 µg/h; more preferably about 2 to about 250 µg/h; and even more preferably about 5 to about 200 µg/h.

In additionally preferred embodiments, the invention provides for a transdermal fentanyl system exhibiting a normalized $C_{max}$ ranging from about 3.3 to about 82.5 ng/ml-(mg/h), preferably about 10 to about 62 ng/ml-(mg/h), more preferably from about 16 to about 41 ng/ml-(mg/h), and even more preferably from about 20 to about 35 ng/ml-(mg/h); and a standardized $C_{max}$ ranging from about 0.01 to about 0.2 ng/ml-cm², preferably about 0.02 to about 0.15 ng/ml-cm², more preferably from about 0.03 to about 0.1 ng/ml-cm², and even more preferably from about 0.04 to about 0.08 ng/ml-cm². The transdermal fentanyl system is about 1 to about 150 cm²; preferably about 2 to about 125 cm²; more preferably about 4 to about 100 cm²; more preferably about 5 to about 75 cm², and even more preferably about 5 to about 50 cm². On administration over skin, the transdermal fentanyl system exhibits a steady state analgesic flux of about 1 to about 10 µg/h-cm²; preferably about 1.5 to about 8 µg/h-cm²; more preferably about 2 to about 5 µg/h-cm², and even more preferably about 2 to about 3 µg/h-cm². Steady-state administration rates obtainable for a transdermal fentanyl system according to this invention range from about 1 to about 300 µg/h; preferably about 2 to about 250 µg/h; and more preferably about 5 to about 200 µg/h.

In additionally preferred embodiments, the invention provides for a transdermal sufentanil system exhibiting a normalized $C_{max}$ ranging from about 0.04 to about 10 ng/ml-(mg/h), preferably about 1 to about 8 ng/ml-(mg/h), and more preferably from about 2 to about 5.5 ng/ml-(mg/h), and even more preferably about 2.5 to about 5 ng/ml-(mg/h); and a standardized $C_{max}$ ranging from about 0.001 to about 0.05 ng/ml-cm², preferably about 0.005 to about 0.04 ng/ml-cm², more preferably from about 0.0075 to about 0.025 ng/ml-cm², and more preferably from about 0.01 to about 0.02 ng/ml-cm². The transdermal sufentanil system comprises a transdermal analgesic system of about 0.5 to about 40 cm²; preferably about 1 to about 35 cm²; and more preferably about 2 to about 30 cm². On administration over skin, the transdermal sufentanil system exhibits a steady state analgesic flux of about 0.1 to about 10 µg/h-cm²; preferably about 0.5 to about 8 µg/h-cm²; more preferably about 0.75 to about 6 µg/h-cm²; more preferably about 1 to about 5 µg/h-cm²; and even more preferably about 1 to about 2.5 µg/h-cm². Steady-state administration rates obtainable for a sufentanil system according to this invention range from about 0.1 to about 200 µg/h; preferably about 0.25 to about 150 µg/h; more preferably about 0.5 to about 100 µg/h; more preferably about 0.75 to about 50 µg/h; and even more preferably about 1 to about 40 µg/h.

Administration is maintained for at least three days, and up to 7 days, with 3-4 day regimen being considered preferable. In preferred embodiments, at least 3%, but not more than 40%, of the total amount of the analgesic in the system is administered during approximately the first 24 hours of use; at least 6%, but not more than 50%, of the total amount of the analgesic is administered during approximately the first 48 hours of use; and at least 10%, but not more than 75%, of the total amount of the analgesic is administered during the administration period. In preferred embodiments, the transdermal analgesic system is a fentanyl system wherein at least 5%, but not more than 40%, of the total amount of the analgesic in the system is administered during approximately the first 24 hours of use; at least 15%, but not more than 50%, of the total amount of the analgesic is administered during approximately the first 48 hours of use; and at least 25%, but not more than 75%, of the total amount of the analgesic is administered during the administration period. In alternative embodiments, the transdermal analgesic system is a sufentanil system wherein at least 3%, but not more than 40%, of the total amount of the analgesic in the system is administered during approximately the first 24 hours of use; at least 6%, but not more than 50%, of the total amount of the analgesic is administered during approximately 48 hours of use; and at least 10%, but not more than 75%, of the total amount of the analgesic is administered during the administration period.

As discussed earlier, the transdermal analgesic system of the invention provides release of the antagonist at a rate sufficient to provide an abuse limiting release rate ratio of the antagonist to the analgesic when the dosage form is subject to abuse, e.g., upon ingestion or substantial immersion of the system in the solvent. In this regard, the transdermal analgesic system of the invention provides release of the antagonist at a rate sufficient to block the opioid effects of the analgesic during abuse situations. As discussed earlier, and illustrated in the examples, the antagonist release rate is controlled by varying the antagonist concentration within the antagonist reservoir, the antagonist salt particle size, the selection of the appropriate antagonist release controlling means, and the processing condition involved in the formation of the transdermal analgesic system. As used herein, "a release rate ratio" refers to the ratio of a release rate of the antagonist to the analgesic over a given period of time measured using suitable standard techniques. In this regard, the present invention provides a transdermal analgesic system wherein the ratio of the amount of antagonist released (i.e. cumulative release) when the patch is abused to the amount of analgesic released (i.e. cumulative release) when the patch is abused is about 0.075:1 to about 30:1, about 0.25:1 to about 20:1; about 0.5:1 to about 16:1; about 0.5:1 to about 14:1; about 0.75:1 to about 12:1; about 1:1 to about 10:1, about 1.5:1 to about 8:1; about 2:1 to about 6:1; and about 2:1 to about 4:1, wherein the period of time of abuse, e.g., ingestion or substantial immersion of the system in a solvent, is up to about 1 minute to about 24 hours, the release based on a standardized test method (e.g. in vitro and in vivo extraction methods) as described in greater detail below. If any one of the test methods satisfies the abuse limiting release rate ratio of the antagonist to the analgesic, it is deemed to satisfy the requirement that the release rate ratios be abuse limiting.

Examples of in vitro extraction methods are described in greater details in the Examples below. In general, the transdermal analgesic system is placed in a standard extraction medium/solution, equilibrated to the target temperature and stirred. Examples of standard extraction media include but are not limited to aqueous medium such as distilled water, a salt solution, aqueous medium containing appropriate buffering agents to provide a pH of about 1 to 14 (e.g., aqueous medium containing phosphate buffer at pH 6.5), an aqueous solvent similar to saliva; organic solvents such as alcohol (e.g. methanol, ethanol, isopropyl alcohol and the like), dimethylfuran, methylene chloride, chloroform, carbon tetrachloride, ether, acetone, benzene, toluene, hexane, pentane, dimethylformamide, formaldehyde, ethyl acetate, methyl ethyl ketone; and common household materials such as, nail polish remover, rubbing alcohol, glycerin, mineral spirits, turpentine, vodka, cooking oil, vinegar, gasoline, kerosene, dry cleaning fluids and the like and mixtures thereof. The volume of the medium is adjusted to be below the solubility limit of the analgesic and the antagonist. The temperature of the extraction can be varied within a range of ambient to near that of boiling, e.g., 25° C., 50° C. and 75° C. Aliquots of the extraction medium are removed at various time points, e.g., 0, 2, 5, 15, 60 and 120 minutes, and diluted with corresponding unused extraction medium. The samples are assayed for antagonist and analgesic content by HPLC. If any one of the test methods satisfies the abuse limiting release rate ratio of the antagonist to the analgesic in any of the above-mentioned extraction medium/solution, it is deemed to satisfy the requirement that the release rate ratios be abuse limiting.

Examples of in vivo extraction methods are described in greater details in the Examples below. In general the transdermal analgesic systems are placed in the oral cavity of animals, e.g., mice, rats, pigs, cats, dogs, primates (monkeys), humans, and the like for a predetermined period, e.g., from about 1 minute to about 2 hours. At the end of the test time period, the transdermal analgesic systems are removed from the oral cavity and allowed to air dry. The transdermal analgesic systems are analyzed for residual analgesic and antagonist contents using standard extraction procedures followed by reverse-phase HPLC analysis.

In certain aspects, the release rate of antagonist into phosphate buffered medium is controlled by membrane selection or surfactant modification of the antagonist release controlling means. In general, the lowest release of the antagonist is provided by the polyethylene film and the faster release of the antagonist is provided by the Celgard membrane. The transdermal analgesic systems wherein analgesic is fentanyl, the antagonist is naltrexone, and the antagonist release controlling means comprises Pluronic modified Solupor materials, the release rate ratio of naltrexone to fentanyl is at least 2:1. The transdermal analgesic systems wherein the analgesic is sufentanil, the greater potency of sufentanil requires a faster antagonist release rate. These faster rates can be provided by an appropriate selection of the antagonist release controlling means such as use of Celgard 3501, various non-woven materials, and exposed antagonist reservoirs where the rate of release is controlled by the amount of antagonist within the antagonist reservoir and the antagonist particle size.

In additional aspects, the present invention provides a transdermal analgesic system wherein the ratio of the amount of antagonist administered during use to the amount of analgesic administered during use is greater than 1:1000, and preferably 1:10,000, depending on the analgesic and the antagonist used, the concentration of the antagonist in the antagonist reservoir and the selection of the antagonist release controlling means. In additional aspects, the present invention provides a transdermal analgesic system wherein the amount of antagonist administered during use is 0.1% or less 168 h after administration. Preferably, the amount of antagonist released when the transdermal analgesic system is abused is 70% or greater after 1, 2, 4, 8 or 24 h of abuse activities.

A preferred embodiment of this invention is a transdermal analgesic system that is bioequivalent to the DURAGESIC® fentanyl system. In particular, a monolithic fentanyl system according to the invention produces substantially the same pharmacokinetic effects (as measured by the area under the blood, plasma or serum drug concentration-time curve (AUC) and the peak plasma or serum concentration ($C_{max}$) of the drug) as compared to the DURAGESIC® transdermal fentanyl system, when studied under similar experimental conditions, as described in greater detail hereinafter.

In additional preferred embodiments, a transdermal analgesic system of this invention is pharmacologically equivalent to the DURAGESIC® fentanyl system. In particular, a monolithic sufentanil system according to the invention produces substantially the same therapeutic effects as compared to the DURAGESIC® transdermal fentanyl system, when studied under similar experimental conditions, as described in greater detail hereinafter.

In general, the standard bioequivalence study is conducted in a crossover fashion in a small number of volunteers, usually with 24 to 36 healthy normal adults. Single doses of the drug containing test product, e.g., transdermal fentanyl system according to the invention, and reference product, e.g., DURAGESIC®/DUROGESIC™ fentanyl system, are administered and blood, plasma or serum levels of the drug are measured over time. Characteristics of these concentration-time curves, such as the area under the blood, plasma or serum drug concentration-time curve (AUC) and the peak blood, plasma or serum concentration ($C_{max}$) of the drug, are examined by statistical procedures as described in greater detail hereinafter. In general, two one-sided statistical tests are carried out using the log-transformed parameter (AUC and $C_{max}$) from the bioequivalence study. The two one-sided tests are carried out at 0.05 level of significance and the 90% confidence interval is computed. The test and the reference formulation/composition are considered bioequivalent if the confidence interval around the ratio of the mean (test/reference product) value for a pharmacokinetic parameter is no less than 80% on the lower end and no more than 125% on the upper end.

Two different products are generally considered to be "pharmacologically equivalent" if they produce substantially the same therapeutic effects when studied under similar experimental conditions, as demonstrated through several in vivo and in vitro methods as described above. Therapeutic effects depend on various factors, such as, potency of the drug, the solubility and diffusivity of the drug in the skin, thickness of the skin, concentration of the drug within the skin application site, concentration of the drug in the drug reservoir, and the like, as described in greater detail hereinafter. In general, pharmacological equivalence is demonstrated using measures such as the peak blood, plasma or serum concentration of the drug normalized for the rate of drug administered (i.e. normalized $C_{max}$ as defined above) and the peak blood, plasma or serum concentration of the drug standardized per unit area of the active drug delivery area of the system (i.e. standardized $C_{max}$ as defined above).

When comparing two different products whose drug administration rate is proportional to the size of the transdermal analgesic system, the is no difference if the peak blood, plasma or serum concentration of the drug ($C_{max}$) is normalized for the rate of drug administered, or standardized per unit area of the active drug delivery area of the system, in order to establish bioequivalence or pharmacological equivalence. However, when comparing two different products having different drug administration rate per unit area, it is necessary to normalize the peak blood, plasma or serum concentration of the drug ($C_{max}$) on the basis of the rate of drug administered to establish bioequivalence or pharmacological equivalence.

Methods of Manufacture

The transdermal analgesic systems are manufactured as follows. The antagonist reservoir and the analgesic reservoirs are manufactured according to known methodology, as described in greater detail below.

Antagonist Reservoir

The antagonist reservoir can be formed by dry blending an antagonist, preferably an antagonist salt, with a polymeric material, preferable a thermoformable material, at high shear and temperature using equipment such as sigma blade mixers or extruders, either batch-wise or continuously. The extrudate is calendared to the desired thickness between release liners, followed by lamination at elevated temperature to a barrier film and/or an analgesic rate controlling means.

In the case of a semi-continuous process, a polymeric material (e.g., ethylene-vinyl acetate copolymer (28 wt % VA)) is added to one feeder hopper of a continuous co-kneader or twin screw extruder (Coperion Buss Kneader, Stuttgart, Germany) at a rate of about 50 pounds per hour. An antagonist, preferably an antagonist salt (e.g., naltrexone hydrochloride dihydrate) is added to a second hopper at a rate of 58.7 pounds per hour. The extruder is operated to produce extrudate at a constant rate of approximately one pound per minute. After exiting from the extruder, the polymer-drug blend is calendared to a desired thickness (about 0.03 mm (1.2 mil)) between barrier layer (e.g., polyester/EVA) and release liner (siliconized polyester film). The trilaminate structure is wound on take-up rolls for further processing.

Parameters such as antagonist loading, antagonist reservoir thickness, membrane selection for the analgesic rate controlling means, and surfactant modification of the analgesic rate controlling means can be varied to achieve the targeted release rate of antagonist to analgesic for a variety of abuse circumstances, as illustrated in the Examples hereinafter. In preferred embodiments, surfactants are coated onto membrane materials forming the analgesic rate controlling means using techniques such as dip-coating, gravure coating, and the like.

Analgesic Reservoir

The transdermal analgesic systems are manufactured according to known methodology. A solution of the polymeric analgesic reservoir material, as described above, is added to a double planetary mixer, followed by addition of desired amounts of the analgesic, preferably fentanyl, more preferably fentanyl base, and optionally, a permeation enhancer. Preferably, the polymeric analgesic reservoir material is an adhesive polymer, which is solubilized in an organic solvent, e.g., ethanol, ethyl acetate, hexane, and the like. The mixer is then closed and activated for a period of time to achieve acceptable uniformity of the ingredients. The mixer is attached by means of connectors to a suitable casting die located at one end of a casting/film drying line. The mixer is pressurized using nitrogen to feed solution to the casting die. Solution is cast as a wet film onto a moving siliconized polyester web. The web is drawn through the lines and a series of ovens are used to evaporate the casting solvent to acceptable residual limits. The dried analgesic reservoir film is then laminated to a selected barrier and the laminate is wound onto the take-up rolls. In another process, the analgesic reservoir can be formed using dry-blending and thermal film-forming using equipment known in the art. Preferably, the materials are dry blended and extruded using a slot die followed by calendaring to an appropriate thickness. Parameters such as analgesic loading, analgesic reservoir thickness, analgesic selections, material selections and manufacturing process can be varied for preparing analgesic reservoirs of the current invention, as illustrated in the Examples hereinafter.

Transdermal Analgesic System

In subsequent operations, the analgesic reservoir containing intermediate and the antagonist reservoir containing intermediate are laminated and the individual transdermal systems are die-cut, separated and unit-packaged using suitable pouchstock. The antagonist reservoir containing intermediate may be laminated immediately after drying the analgesic reservoir containing intermediate. Transdermal analgesic systems are cartoned using conventional equipment.

EXPERIMENTAL

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Specific examples of various transdermal analgesic systems of the invention which are capable of administering fentanyl and analogs thereof for extended periods of time will be described in the examples set for hereinafter. The transdermal analgesic systems comprise analgesic reservoirs comprising an analgesic at concentration greater than, equal to, or less than saturation concentration. The adhesive-analgesic reservoir systems wherein the analgesic reservoir comprises a single phase formulation of free undissolved components containing an amount of fentanyl at subsaturation concentration are presently considered preferable according to our invention. In the following examples all percentages are by weight unless noted otherwise.

Example 1

Monolithic transdermal analgesic reservoirs according to FIG. 1 were prepared containing 1.5 mg/cm$^2$ of fentanyl base. A polacrylate adhesive (National Starch 87-2287, 100 g) was solubilized in a solvent (ethyl acetate, 128 ml). Fentanyl base was added to the polacrylate adhesive solution in amounts sufficient to generate a mixture containing 4 wt % of fentanyl in the adhesive solution and stirred to dissolve the analgesic. The solution was cast on to a peelable protective liner such as a siliconized polyester film, and the solvent was evaporated to provide a 0.05 mm (2 mil) thick reservoir layer.

Similarly, monolithic transdermal analgesic reservoirs were prepared using the polacrylate adhesive (National Starch 87-4287, 100 g), as described above.

Example 2

Monolithic transdermal analgesic reservoirs were prepared as described in Example 1 with the following exceptions.

Materials were dry blended, in the absence of ethyl acetate, and extruded using a slot die followed by calendaring to an appropriate thickness.

Example 3

Monolithic transdermal analgesic reservoirs according to FIG. 1 were prepared as follows. A polacrylate adhesive (National Starch 87-2287, 500 g) and glyceryl monolaurate (GML, 10 g) were dissolved in a solvent (ethyl acetate, 640 ml). Fentanyl base was added to the polacrylate adhesive solution in amounts sufficient to generate a mixture containing 4 wt % of fentanyl in the adhesive solution and stirred to dissolve the analgesic. The solution was cast on to a peelable protective liner such as a siliconized polyester film and the solvent was evaporated to provide a 0.045 mm (1.8 mil) thick reservoir layer. The analgesic transdermal systems contained 0.35 mg/cm$^2$ of fentanyl base.

Similarly, monolithic transdermal analgesic reservoirs are prepared using the polacrylate adhesive (National Starch 87-4287,100 g), as described above.

Example 4

Monolithic transdermal analgesic reservoirs as described in Example 3 with the following exceptions. Materials were dry blended, in the absence of ethyl acetate, and extruded using a slot die followed by calendaring to an appropriate thickness.

Example 5

Monolithic transdermal analgesic reservoirs were prepared comprising respectively, 0.25, 0.5, 0.75, 1.0 and 1.1 mg each of sufentanil, per 2.54 cm$^2$, in a polacrylate adhesive (National Starch 87-4287, as described in Example 1 above.

Similarly, monolithic transdermal analgesic reservoirs were prepared using the polacrylate adhesive (National Starch 87-2287, 100 g), as described above.

Example 6

Monolithic transdermal analgesic reservoirs were prepared containing, 0.25, 0.5, 0.75, 1.0 and 1.1 mg each of sufentanil, and permeation enhancers (1 mg) comprising lauryl pyroglutamate, glycerol monolaurate, glycerol monocaprylate and glycerol monocaproate, respectively per 2.54 cm$^2$ as described in Example 5.

Example 7

The transdermal analgesic reservoir described above in examples 1-6 was laminated to the PET face of the PET/EVA barrier layer (for example as depicted in FIG. 1) to provide a transdermal analgesic reservoir containing intermediate.

Example 8

The transdermal analgesic reservoir described above in examples 1-6 is coated with an adhesive coating followed by lamination to the PET face of the PET/EVA barrier layer (for example as depicted in FIG. 3) to provide a transdermal analgesic reservoir containing intermediate.

Example 9

The transdermal analgesic reservoir described above in examples 1-6 is laminated to an analgesic rate controlling membrane followed by lamination to the PET face of the PET/EVA barrier layer (for example as depicted in FIG. 2) to provide a transdermal analgesic reservoir containing intermediate.

Example 10

The transdermal analgesic reservoir described above in examples 1-6 is laminated to an analgesic rate controlling membrane. The skin proximate surface of the analgesic rate controlling membrane is coated with an adhesive coating followed by lamination to the PET face of the PET/EVA barrier layer (for example as depicted in FIG. 4) to provide a transdermal analgesic reservoir containing intermediate.

Example 11

Antagonist reservoir containing intermediates were prepared as follows. A thermoformable polymer (460 g), such as Engage® ethylene-octene copolymer, (DuPont-Dow Elastomers, Midland, Mich.), was placed within the bowl of a high torque blender. The bowl was heated (150° C.) and the polymer pellets were blended until the polymer pellets were sufficiently masticated to provide a molten mass (10 minutes). The antagonist (naltrexone hydrochloride USP, 540 g) was added to the mixing bowl, and the mixture was blended for about 30 minutes. The polymer melt was emptied from the blending bowl and extruded between two moving webs: an upper layer of 0.05 mm (2 mil) polyester/EVA film (EVA side toward the melt) and a lower layer of 0.075 mm (3 mil) siliconized polyester film. The three-layer film structure was passed through calendar rolls to size the antagonist reservoir disposed on the barrier layer to about 0.025 mm (1 mil) thickness. The moving web was taken up in roll form at the end of the extrusion line.

In a second pass through the line, the siliconized interleaving was removed and a microporous polyethylene film (SOLUPOR, DSM Solutech, Heerlan, the Netherlands) was heat laminated to the exposed antagonist reservoir using a calendar. The microporous membrane provides the antagonist release controlling means for the final transdermal analgesic system. The resulting structure was taken up in roll form as an intermediate product comprising the antagonist reservoir disposed on the antagonist release controlling means or layer.

The antagonist reservoir containing intermediate described above was laminated to the analgesic-containing adhesive film exiting the drying ovens described in examples 1-6 above, providing a six-layer film laminate: peelable liner, analgesic reservoir; optionally containing a rate control membrane, barrier layer (polyester, EVA), antagonist reservoir (polyethyleneoctene-naltrexone HCl) and the antagonist release controlling means (microporous polyethylene). The total film thickness was about 0.2 mm (8 mil).

The six-ply film was die-cut to individual transdermal analgesic systems corresponding to analgesic delivery areas of 1 cm$^2$ to 44 cm$^2$. In fentanyl containing systems, the fentanyl to naltrexone loading ratio in the final systems was 1:2, and the fentanyl delivery rates of about 12.5 to about 100 µg/h depending upon the system area. In sufentanil containing systems, the sufentanil to naltrexone loading ratio in the final systems is 1:4-16, and the sufentanil delivery rates of about 1.5 to about 12 µg/h depending upon the system area.

Example 12

Antagonist reservoir containing intermediates were prepared as follows. A thermoformable polymer (460 g), such as Engage® ethylene-octene copolymer, (DuPont-Dow Elastomers, Midland, Mich.), was placed within the bowl of a high torque blender. The bowl was heated (150° C.) and the polymer pellets were blended until the polymer pellets were sufficiently masticated to provide a molten mass (10 minutes). The antagonist (naltrexone hydrochloride USP, 540 g) was added to the mixing bowl, and the mixture was blended for about 30 minutes. The polymer melt was emptied from the blending bowl and extruded between two moving webs: an upper layer of 0.075 mm (3 mil) fluoropolymer release liner film (fluorocarbon diacrylate coated polyester film), and a lower layer of 0.075 mm (3 mil) siliconized polyester film. The three-layer film structure was passed through calendar rolls to size the antagonist reservoir disposed on the barrier layer to about 0.025 mm (1 mil) thickness. The moving web was taken up in roll form at the end of the extrusion line.

In a second pass through the line, one of the siliconized interleaving was removed and a microporous polyethylene film (SoluPor, Solutech, Denmark) was heat laminated to the exposed antagonist reservoir using a calendar. The microporous membrane provides the antagonist release controlling means for the final transdermal analgesic system. The resulting structure was taken up in roll form as an intermediate product comprising the antagonist reservoir.

In the third pass through the line, the siliconized interleaving was removed and an adhesive layer, was laminated to the exposed antagonist reservoir using a laminator, providing a four layer film laminate: adhesive layer, barrier layer, antagonist reservoir (polyethyleneoctene-naltrexone HCl) and antagonist release controlling means (microporous polyethylene). The four ply film was die cut to individual units corresponding to form fill seal (FFS) system areas of 10, 20, 30 and 40 cm$^2$.

Analgesic reservoir containing intermediates are prepared as follows. Fentanyl base (1.4 Kg) was slurried in purified water (5 L, USP) in a vessel. Ethanol (25 Kg, USP) and water (65 L, USP) were mixed in a 40 gallon pressure vessel, the solution was stirred, and allowed to cool to room temperature. The fentanyl slurry was added to the ethanol solution, using water (4 L, USP) to rinse the vessel quantitatively. In a separate vessel, hydroxyethyl cellulose (2 Kg, QP 100,000 [HEC], NF) was slurried with water (4 L). The hydroxyethyl cellulose slurry was added with mixing to the fentanyl mixture in the 40 gallon mixer. The remaining hydroxyethyl cellulose was rinsed using water (2 L) and added to the large mixer vessel. The vessel was immediately stirred at 100 cycles/minute until the analgesic reservoir mixtures gels.

The pressure vessel containing the fentanyl gel was attached to a multi-nozzle gel placement array mounted on a Bodolay Form-Fill-Sealing (FFS) machine. A laminate composed of the protective liner (peelable PET-silicone film), adhesive layer (silicone adhesive film, 1.57 mil), and analgesic release rate controlling means (an EVA film (9% VA), 2 mil) was laid out onto the equipment used to build the form fill seal systems. The analgesic reservoir was metered onto the protective liner/adhesive layer/analgesic release rate controlling means such that the gel contacted the analgesic release rate controlling means. The barrier layer (PET/EVA) was laid out such that it covered the gel. The EVA component of the barrier layer contacted the analgesic release controlling membrane. The perimeter of the construction was heat laminated, forming the analgesic portion of the system forming peripherally sealed systems with 245 mg of reservoir gel per 10 cm$^2$ system active drug release area. The film was die cut to individual units corresponding to analgesic delivery areas of 10 to 40 cm$^2$ to form the analgesic reservoir containing intermediate.

The adhesive surface of the antagonist reservoir containing intermediate is laminated onto the barrier layer of the analgesic reservoir containing intermediate to form the transdermal analgesic system having a form fill seal (FFS) analgesic reservoir.

In fentanyl containing systems, the fentanyl to naltrexone loading ratio in the final systems is 0.5 to 4, and the fentanyl delivery rates of about 12.5 to about 100 µg/h depending on the system area.

Example 13

The antagonist reservoir containing intermediate described in Example 11 is laminated to the analgesic reservoir described in Examples 9 and 10 above, providing a eight-layer film laminate: peelable liner, adhesive layer, analgesic rate control membrane, analgesic reservoir (analgesic-adhesive layer), barrier layer (polyester, EVA), antagonist reservoir (polyethyleneoctene-naltrexone HCl) and antagonist release controlling means (microporous polyethylene).

The eight-ply film is die-cut to individual transdermal analgesic systems corresponding to analgesic delivery areas of 5.5 to 44 cm$^2$. In fentanyl containing systems, the fentanyl to naltrexone loading ratio in the final systems is 1:2, and the fentanyl delivery rates of about 12.5 to about 100 µg/h depending upon the system area. In sufentanil containing systems, the sufentanil to naltrexone loading ratio in the final systems is 1:4-16, and the sufentanil delivery rates of about 1.5 to about 12 µg/h depending upon the system area.

Example 14

A thermoformable polymer, polyolefin elastomer (460 g), such as Engage® ethylene-octene copolymer, (DuPont-Dow Elastomers, Midland, Mich.), was melt blended (88-100° C.) with naltrexone hydrochloride dihydrate (690 g) for about 1.5 to 2.5 hours. The mixture was extruded between differential release liners, calendared to a thickness of 0.025 mm (1 mil) to form an antagonist reservoir. The antagonist reservoir was laminated to the PE face of a PET-PE barrier film (Mediflex 1203, Mylan, St. Albans, Vt.), at 0-100° C., 71 psig, 4 ft/min. The remaining release liner was removed and the barrier layers were laminated at 60° C., 38 psig, 4 ft/min. The antagonist release rate controlling means, e.g., Solupor 10P05A, Pluronic-modified Solupor, Celgard microporous polypropylene (Grades 3401 and 3501), spun-bonded polypropylene, and polyethylene film were laminated to the antagonist reservoir between 60 and 90 psig, 4 ft/min.

The PET face of the antagonist reservoir containing intermediate described above was laminated to the analgesic-containing adhesive film exiting the drying ovens described in Examples 1-6 above, at 24 ft/min, 25° C., 70 psig. The liner was replaced with a slit release liner to enable easy system removal from the liner, and die cut to the desired dimensions, 5.5 to 44 cm$^2$.

Example 15

A thermoformable polymer, such as Elvax® 210 ethylene-vinyl acetate copolymer (1.61 Kg, 28% vinyl acetate, E. I. DuPont de Nemours, Wilmington, Del.), was melt blended (77-88° C.) with naltrexone hydrochloride dihydrate (1.89 Kg) for about 1.5 to 2.5 hours. The mixture was extruded between differential release liners, and calendared (0.031 mm) to form an antagonist reservoir. The antagonist reservoir was laminated to the EVA face of a PET-EVA barrier film (Scotchpac 9733, 3M, Minneapolis, Minn.), at 80-85° C., 70-90 psig, 4-19 ft/min. The remaining release liner was removed and the antagonist release rate controlling means, microporous polyethylene (e.g., Solupor 10P05A, or Pluronic-modified Solupor,) was laminated to the antagonist reservoir between 80-85° C., 50-54 psig, 4-24 ft/min.

The PET face of the antagonist reservoir containing intermediate described above was laminated to the analgesic-containing adhesive film exiting the drying ovens described in Examples 1-6 above, at 24 ft/min, 25° C., 70 psig. The liner was replaced with a slit release liner to enable easy system removal from the liner, and die cut to individual transdermal analgesic systems corresponding to analgesic delivery areas of 5.25 to 44 cm$^2$.

Example 16

The antagonist reservoir containing intermediate described in the Examples above was prepared with the following exceptions. Antagonist release controlling means were prepared as follows. Pluronic F108NF solutions (0.5, 1.0, and 2.0 wt %) were prepared in a solvent (3% water: 97% ethanol). The Solupor material 10P05A was coated with the Pluronic solutions and dried at room temperature overnight, providing coating weights of 35 µg/cm$^2$, 50 µg/cm$^2$, and 90 µg/cm$^2$ for the 0.5, 1.0, and 2.0 wt % Pluronic solutions, respectively. These antagonist release controlling means, i.e. surfactant-modified membranes were laminated to the antagonist reservoir as described in the previous examples.

Example 17

The antagonist reservoir containing intermediate described in the Examples above is prepared with the following exceptions. Antagonist release controlling means (a salt-filled membrane which forms pores in situ upon exposure to water) is prepared as follows. Ethylene-vinyl acetate copolymer (EVA) with 28% vinyl acetate monomer (Elvax 210, E. I. DuPont de Nemours, Wilmington, Del.) is added to the hopper of a cryogrinder (10 Kg). The cryogrinder is then filled to the mark with liquid nitrogen and the top is sealed. The grinder is activated for about 10 minutes and the polymer pellets are comminuted to an average particle size of about 0.05 mm, and dried (using a stream of warm air) to obtain the ground polymer.

Powdered sodium chloride, with approximately 2% magnesium sulfate, (National Formulary, about 10 Kg) is added to the hopper of a V-blender. The ground polymer (10 Kg) is then added to the hopper. The hopper is activated to rotate for approximately 15 minutes, to obtain a powder blend that is a consistent mixture of polymer and sodium chloride.

The powder blend is continuously fed to the addition-port of a single-screw extruder, the heating sections of which are pre-warmed to approximately 110° C. At the end of the extruder, a flex-nip die is attached which has been set to an exit thickness of about 0.25 mm (10 mil). The extruder is operated to produce film that is fed to the rolls of a three-roll calendar. The roll-nip is set to produce a continuous film exiting the calendar that is about 0.03 mm (1.5 mil) thick. This film is wound on take-up rolls for further manufacturing use.

These antagonist release controlling means, i.e. salt-containing film are laminated to the antagonist reservoir as described in the previous examples. Final systems are die-cut and packaged. Upon immersion of such systems in water, the sodium chloride layer rapidly desorbs the water-soluble salt. The resulting film forms an in situ microporous membrane that provides a release rate ratio of the antagonist to the analgesic of least 2:1 and up to 20:1.

Example 18

The antagonist reservoir containing intermediates as described in Examples 11-17 are manufactured using an alternative continuous process. A gravimetric or volumetric feeder is used to feed thermoplastic polymer into a twin screw extruder, reciprocating single screw extruder ("co-kneader") or continuous compounder. The antagonist is fed in a like manner into the melted polymer and mixed, and extruded into a calendar into the intermediate antagonist reservoir laminate. Alternatively, the mixture is extruded into a strand or rod, cut into pellets (approximately 5-10 mm) and subsequently extruded in a second step.

Example 19

The antagonist intermediate containing reservoir described in Examples 11-18 is prepared with the following exception. The intermediate antagonist reservoir is extrusion coated directly to the EVA face of the barrier layer on a chill roll and the antagonist rate controlling layer is laminated in the same process step.

Example 20

The systems manufactured according to Examples 11-19 were used to study the release of naltrexone from the system upon immersion in water at ambient temperature, i.e. room temperature. The transdermal analgesic systems were immersed in distilled water. After selected time intervals, the systems were moved to fresh extraction media. This operation was repeated for a total time of 24 hours. The naltrexone released during this test procedure matched the rate and extent of the fentanyl released as determined after performing a similar test procedure to measure opioid release. These systems released naltrexone to fentanyl at a ratio of 2:1 over at least a one-hour period of immersion in water.

Example 21

The systems manufactured according to Examples 11-20 were used to study the release of naltrexone from the system upon immersion in a buffered aqueous medium containing phosphate buffer at pH 6.5 at ambient temperature, i.e. room temperature or at boiling temperature. The volume of the medium was adjusted to be below the solubility limit of the antagonist and the analgesic.

Figure 6:
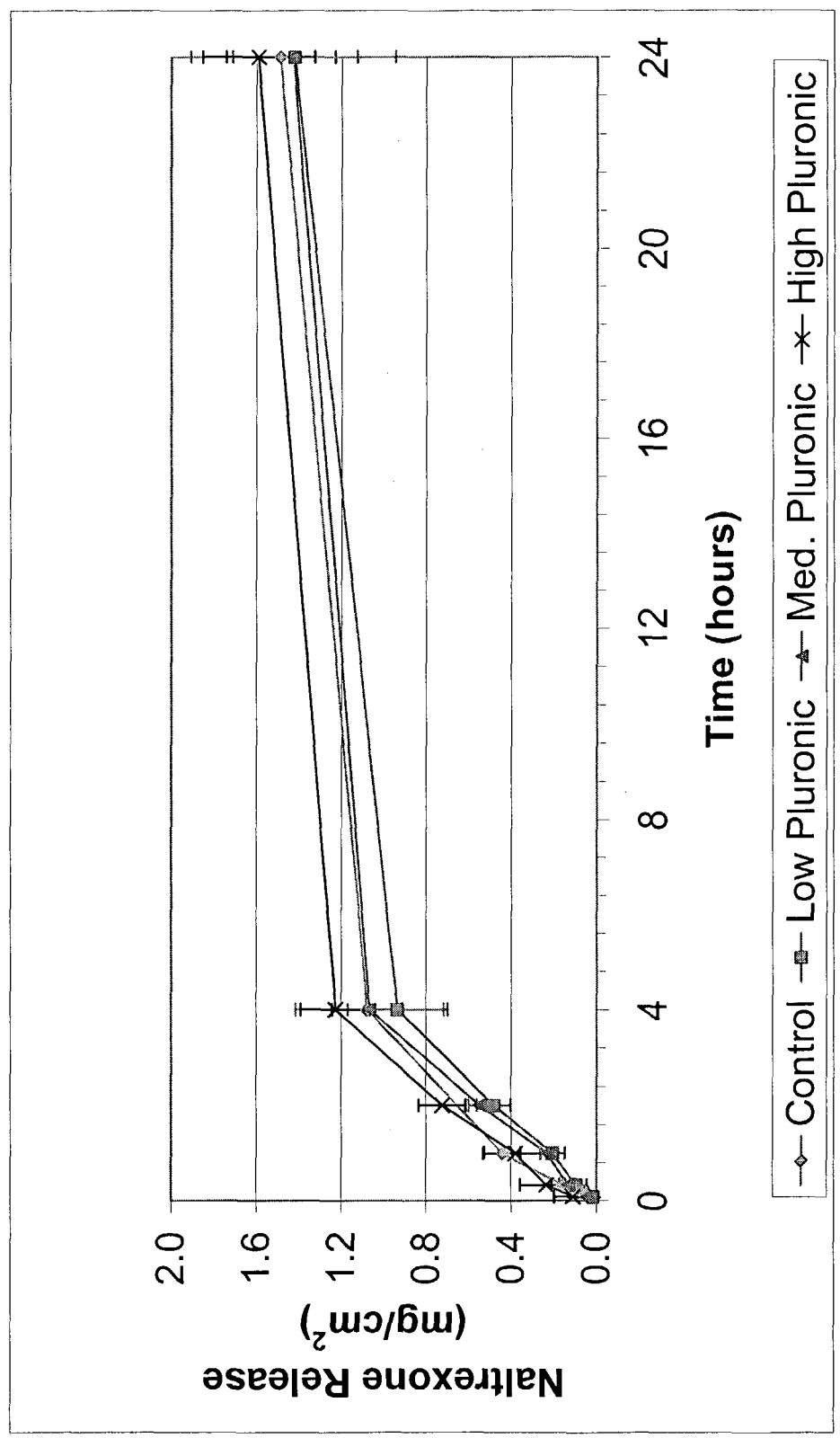
FIGS. 6, 7 and 8 illustrate the cumulative release of naltrexone from a Pluronic coated-Solupor antagonist release controlling means.
Figure 7:
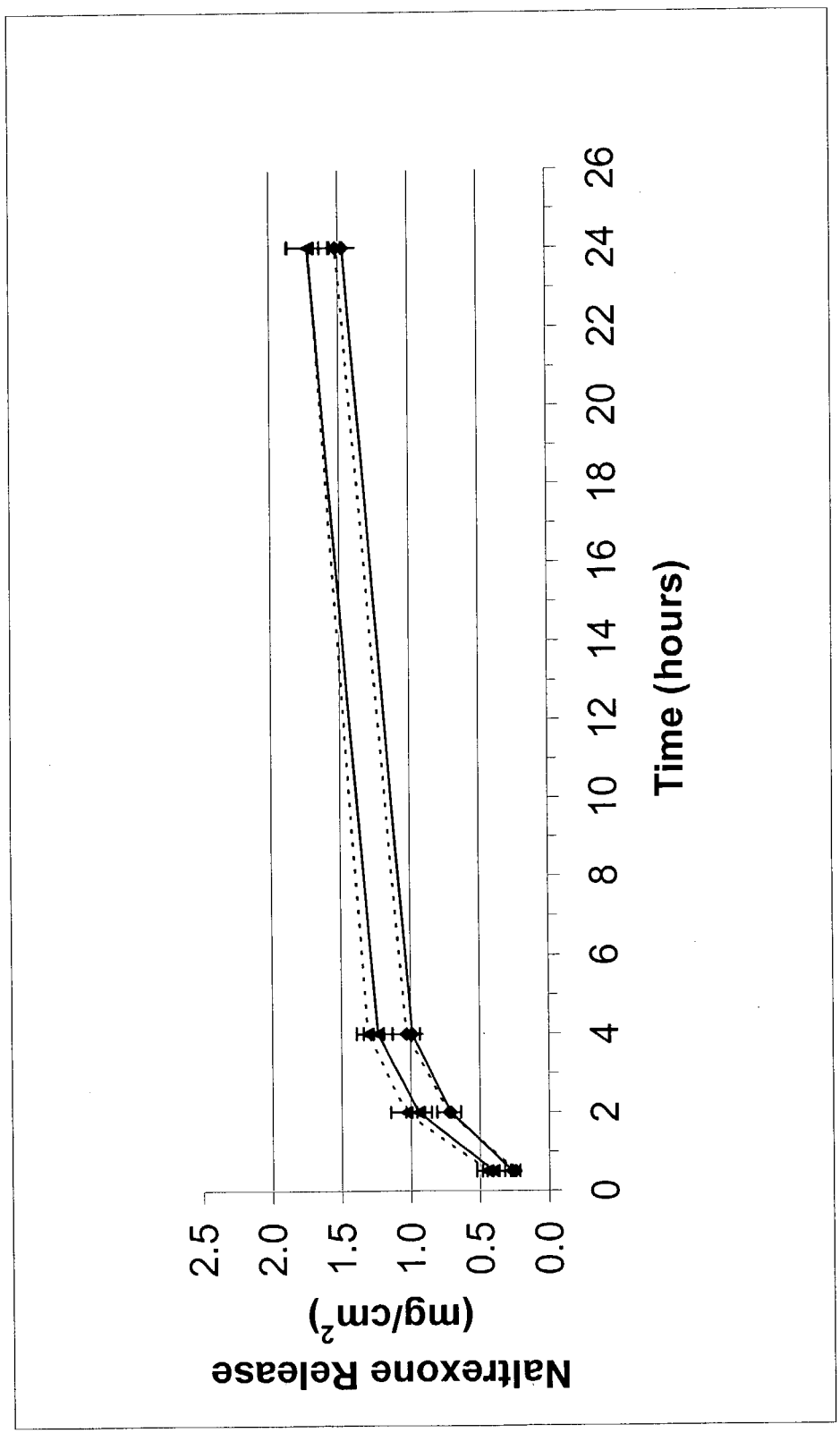
Figure 8:
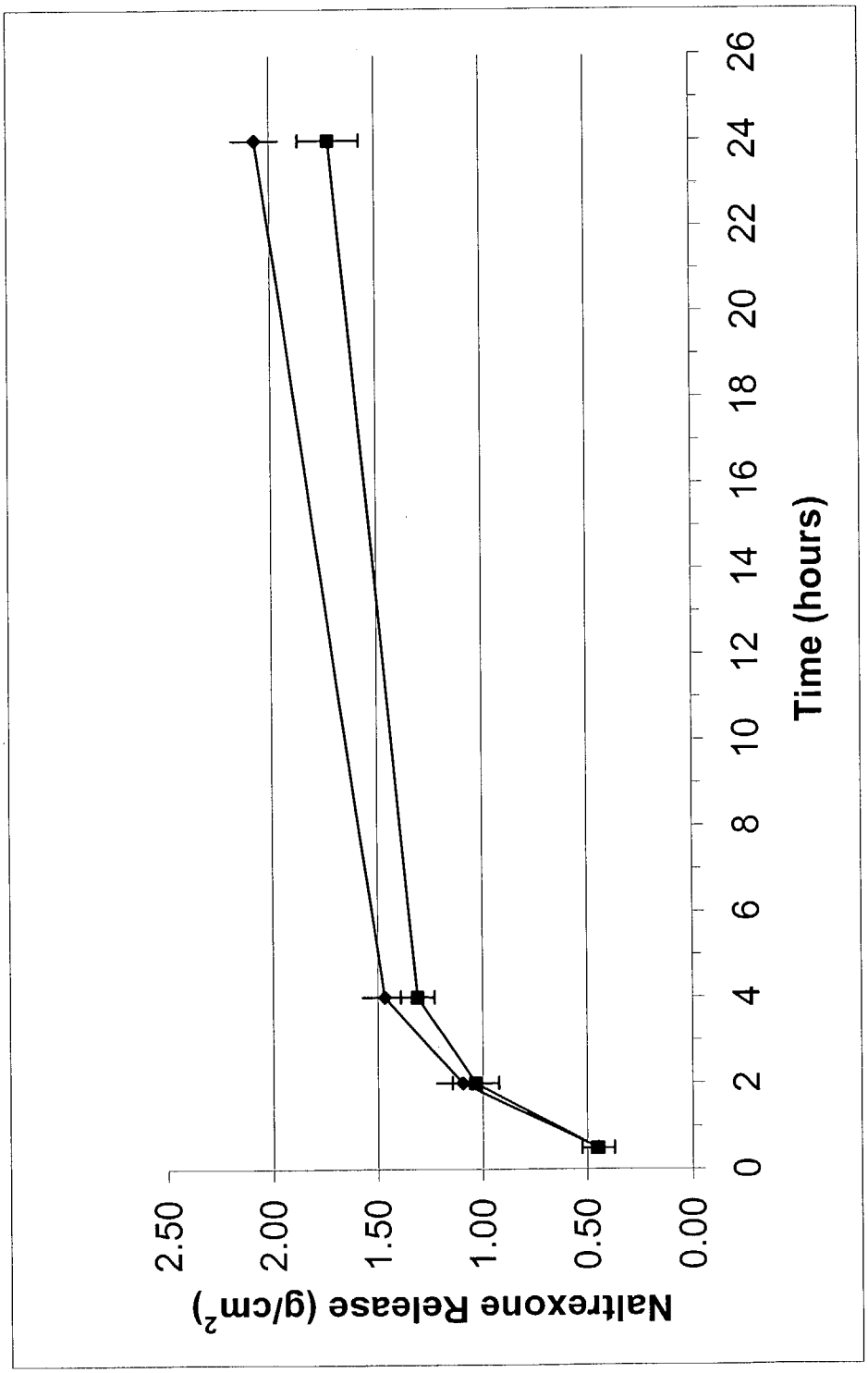
Figure 9:
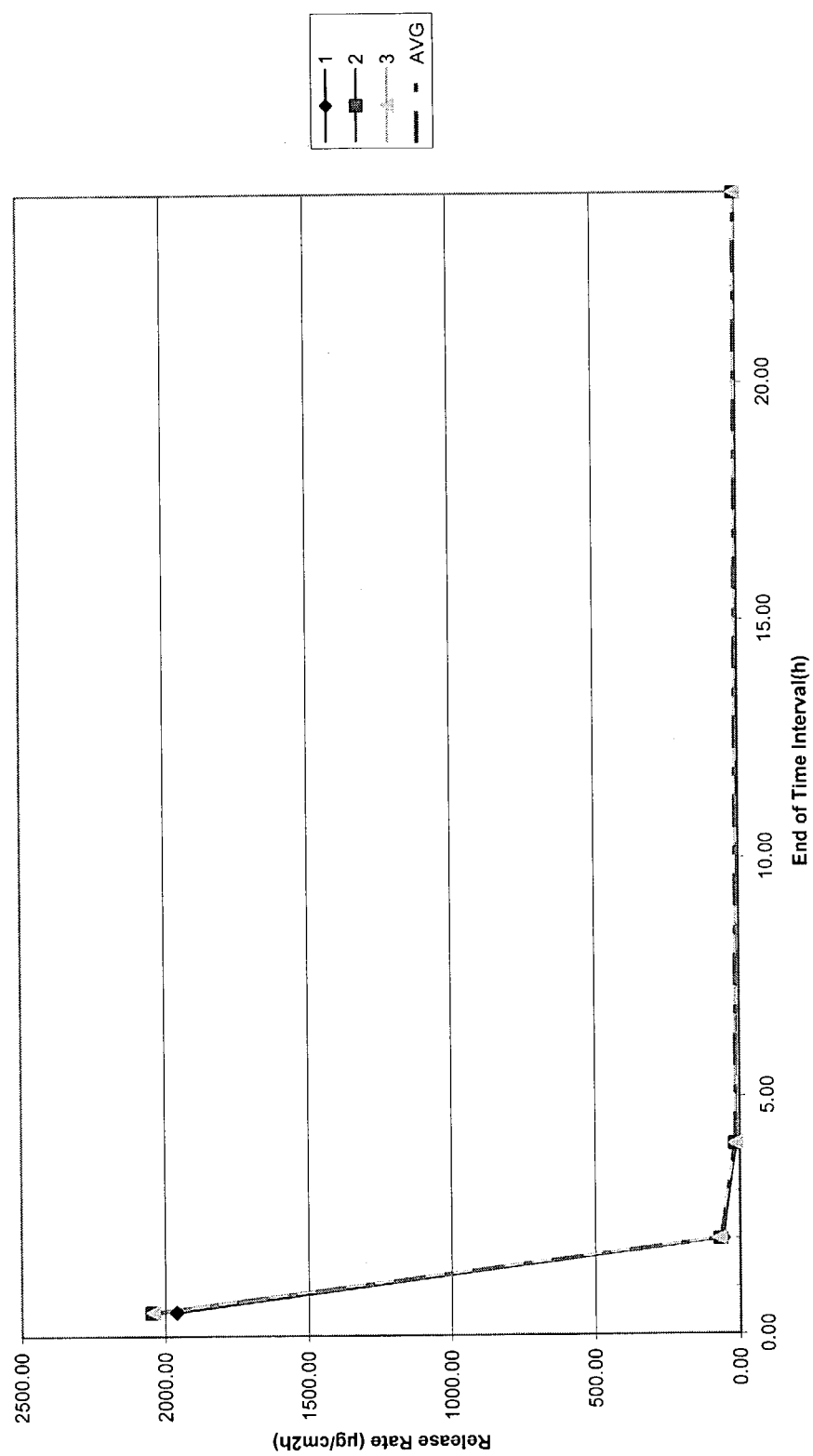
FIGS. 9 and 10 illustrate release rate and cumulative release of naltrexone, respectively, from a Celgard 3401 antagonist release controlling means.
Figure 10:
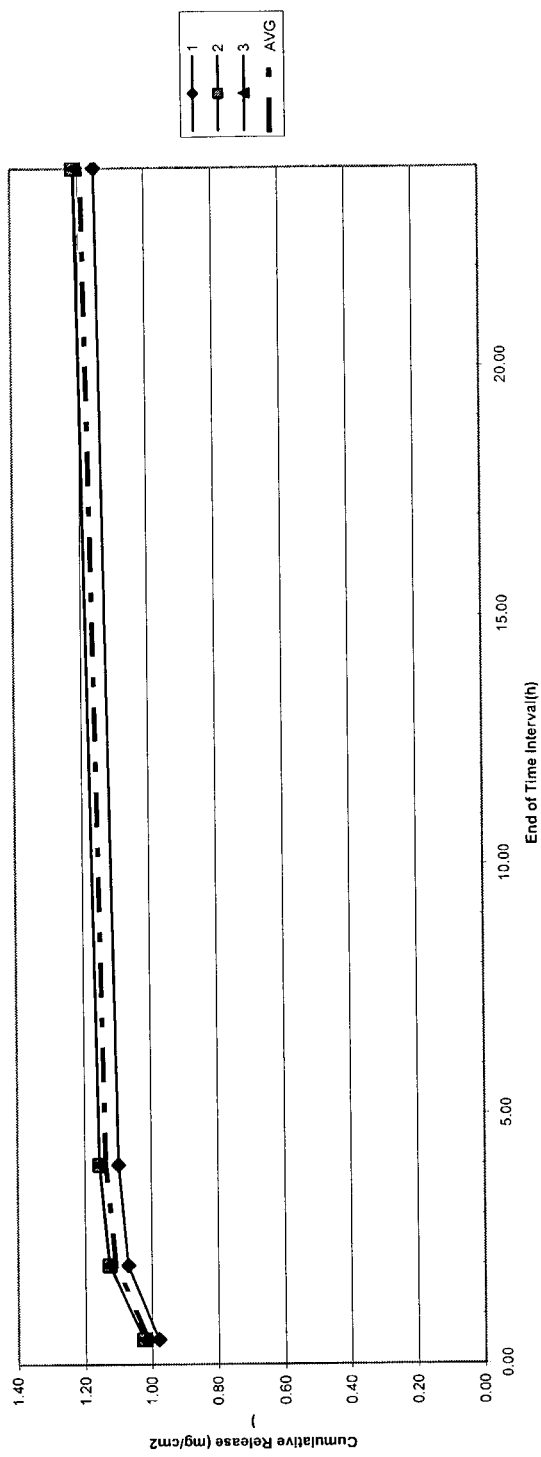
Figure 11:
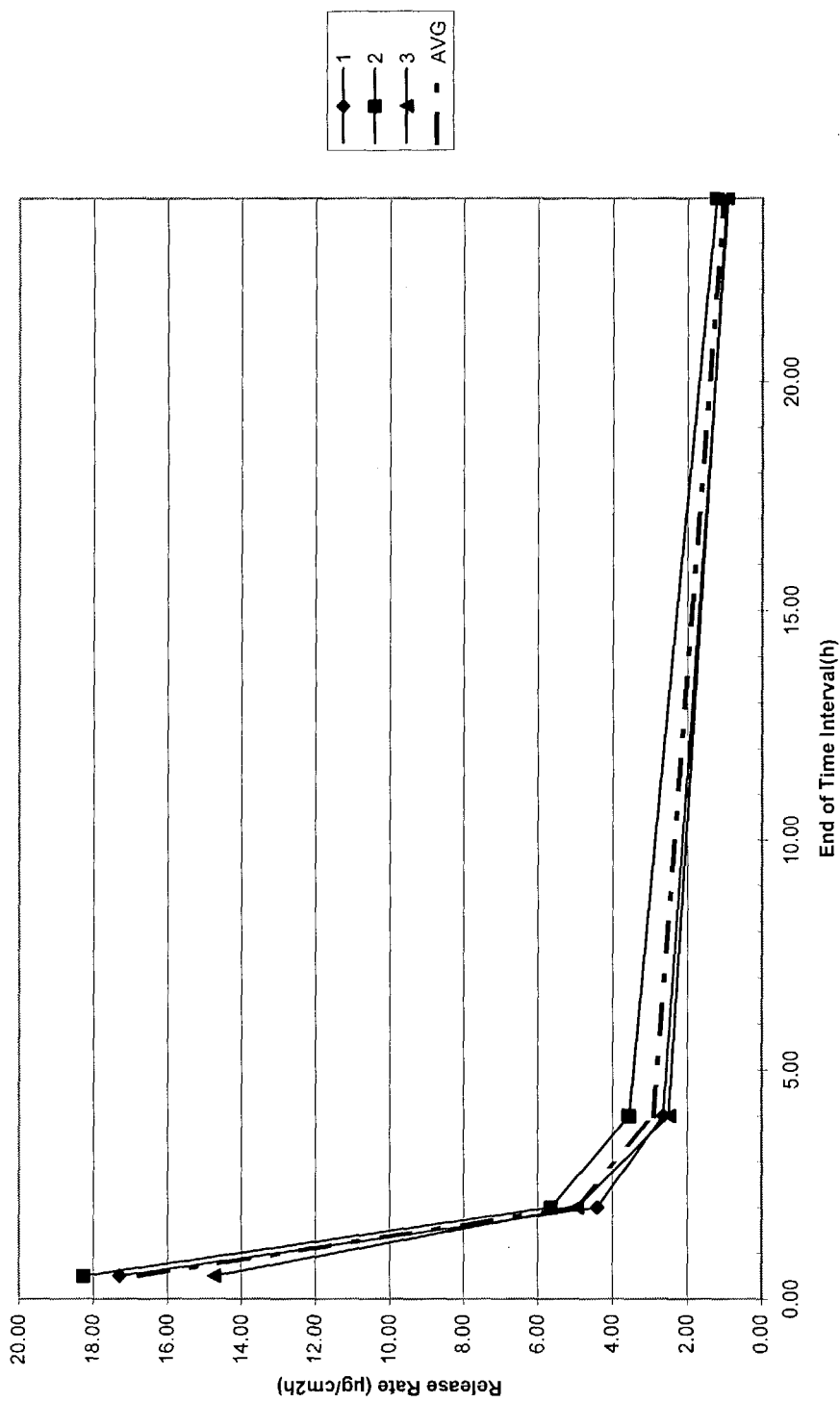
FIGS. 11 and 12 illustrate release rate and cumulative release of naltrexone, respectively, from an impermeable LDPE antagonist release controlling means.
Figure 12:
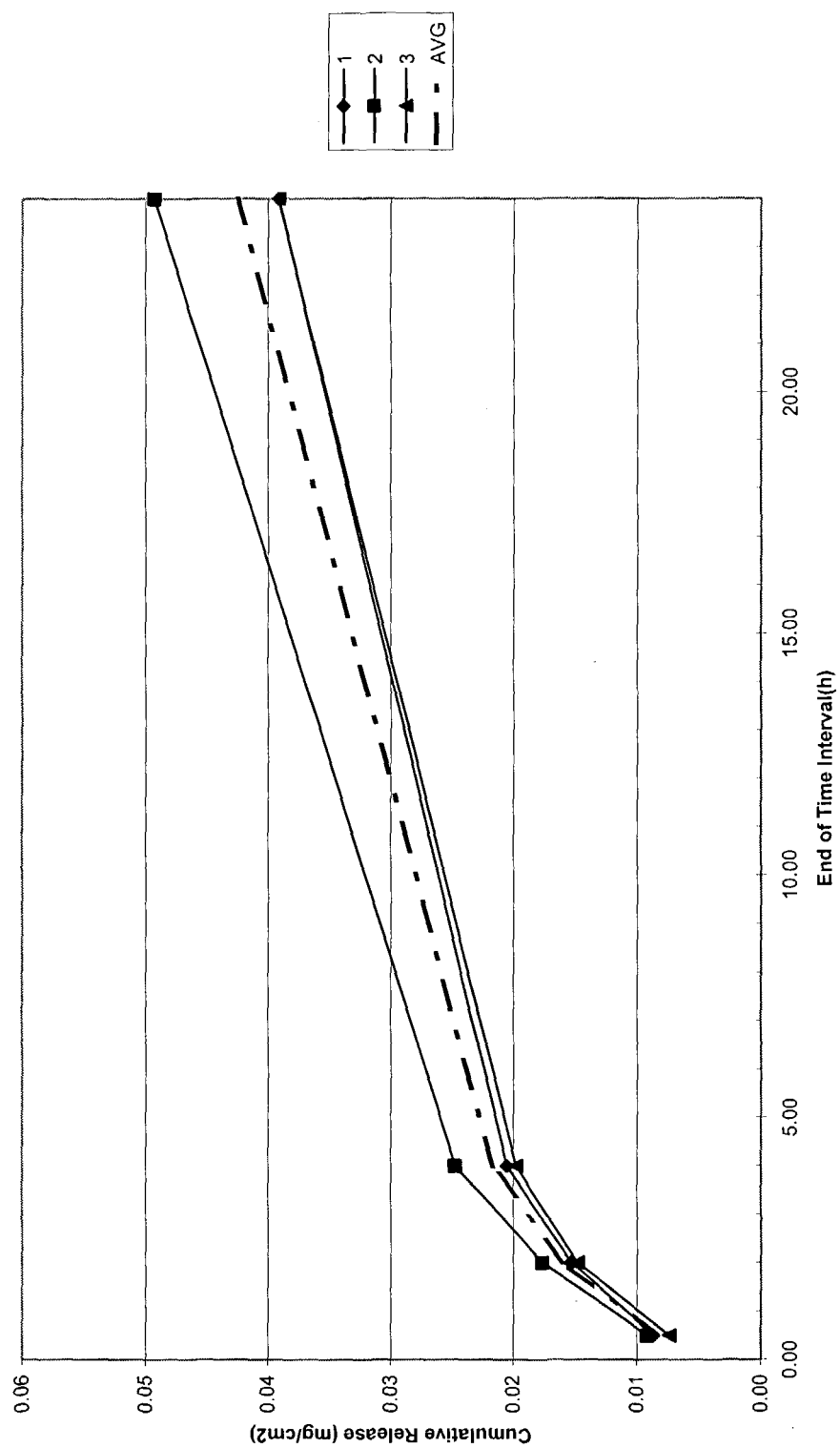
Figure 13:
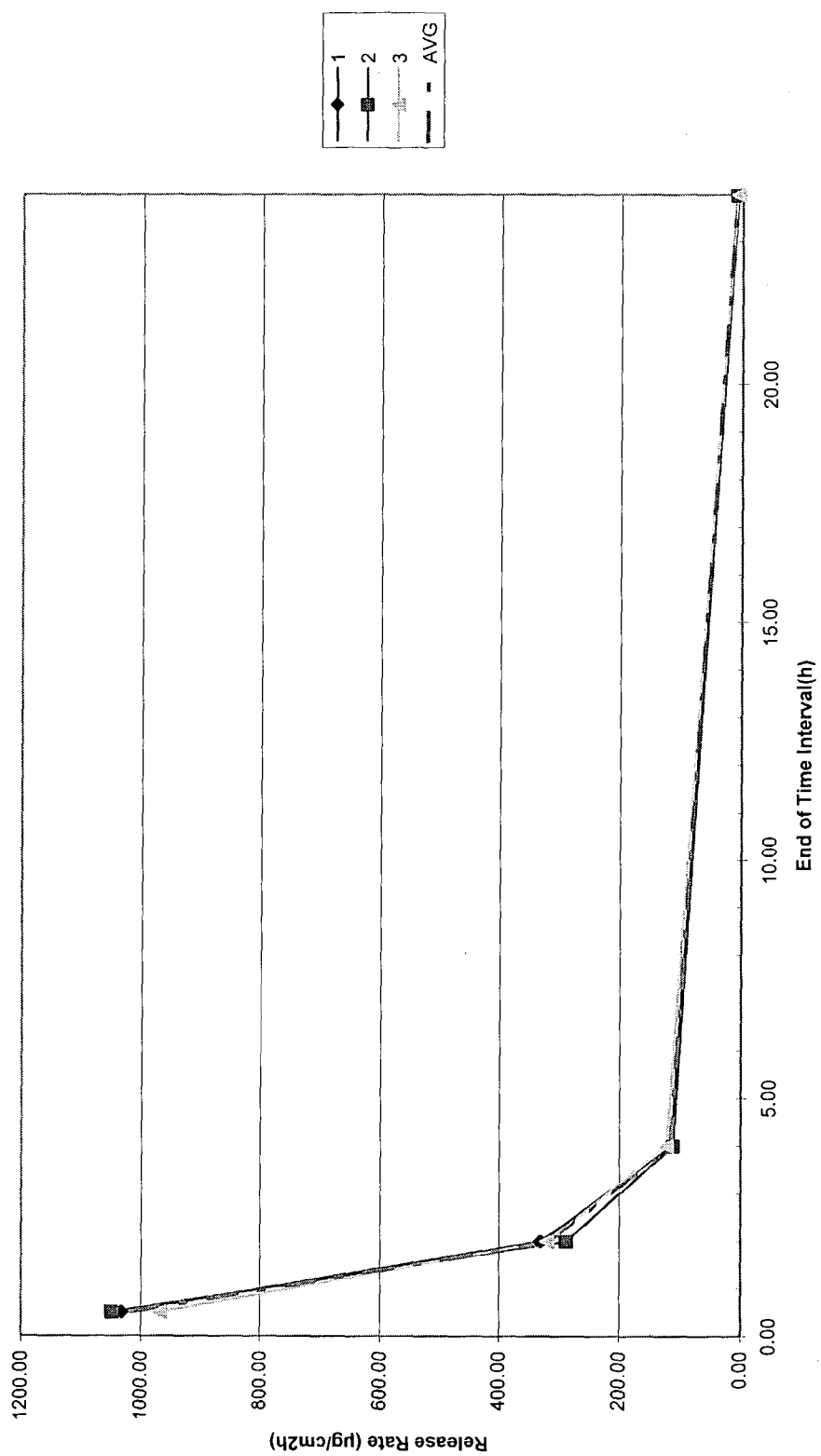
FIGS. 13 and 14 illustrate release rate and cumulative release of naltrexone, respectively, from a Celgard 3501 antagonist release controlling means.
Figure 14:
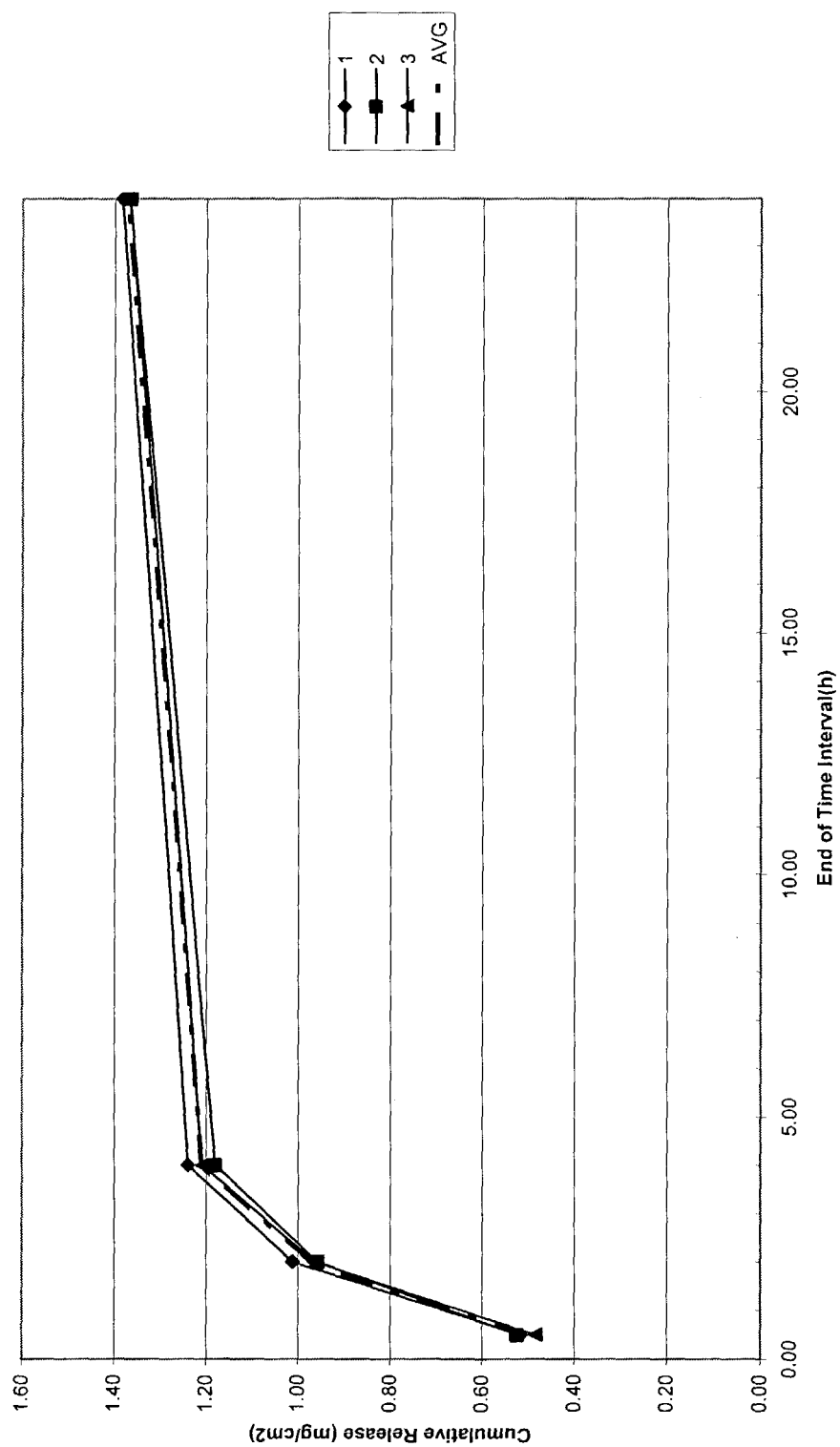
Figure 15:
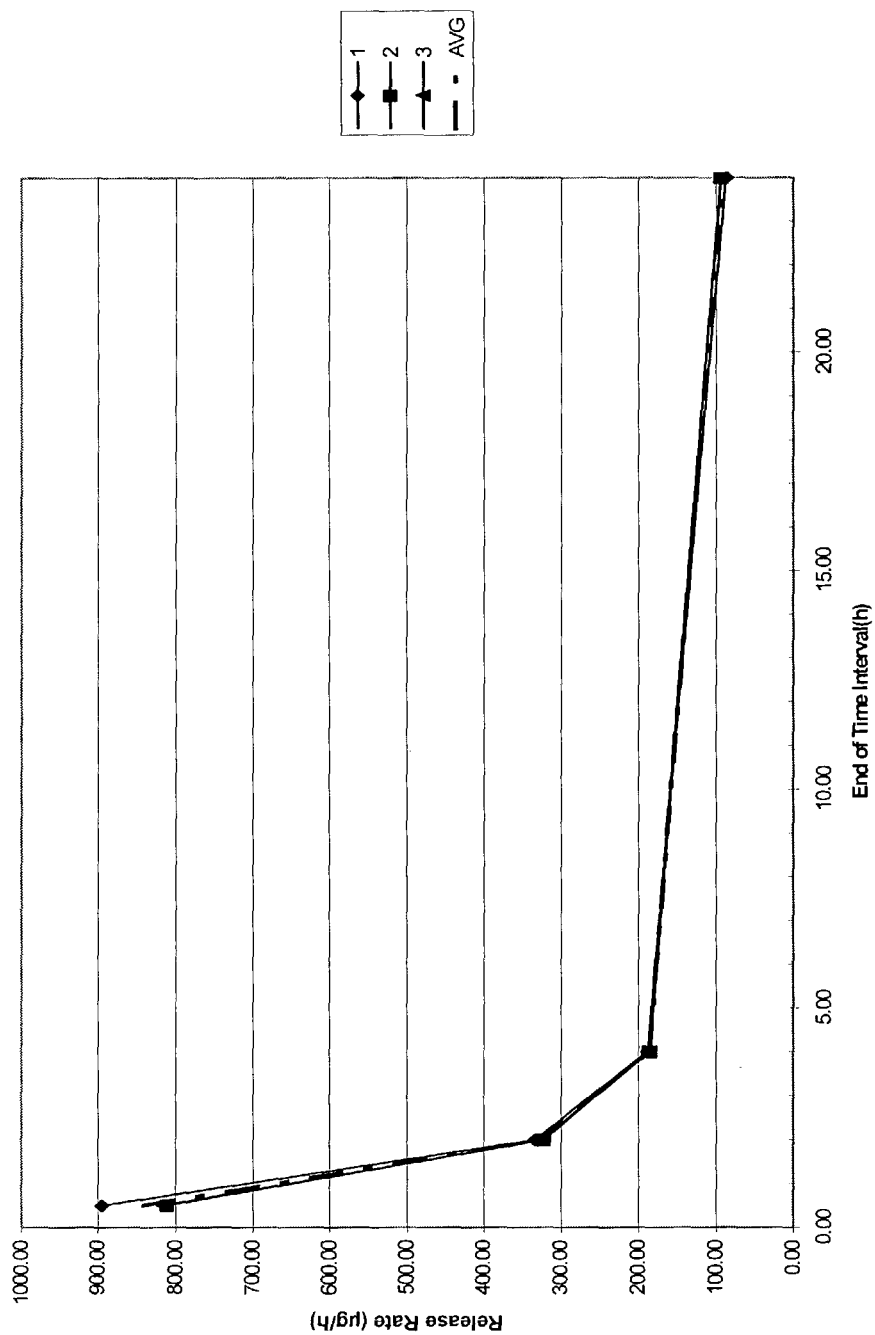
FIGS. 15 and 16 illustrate release rate and cumulative release of naltrexone, respectively, from a spun bonded polypropylene antagonist release controlling means.
Figure 16:
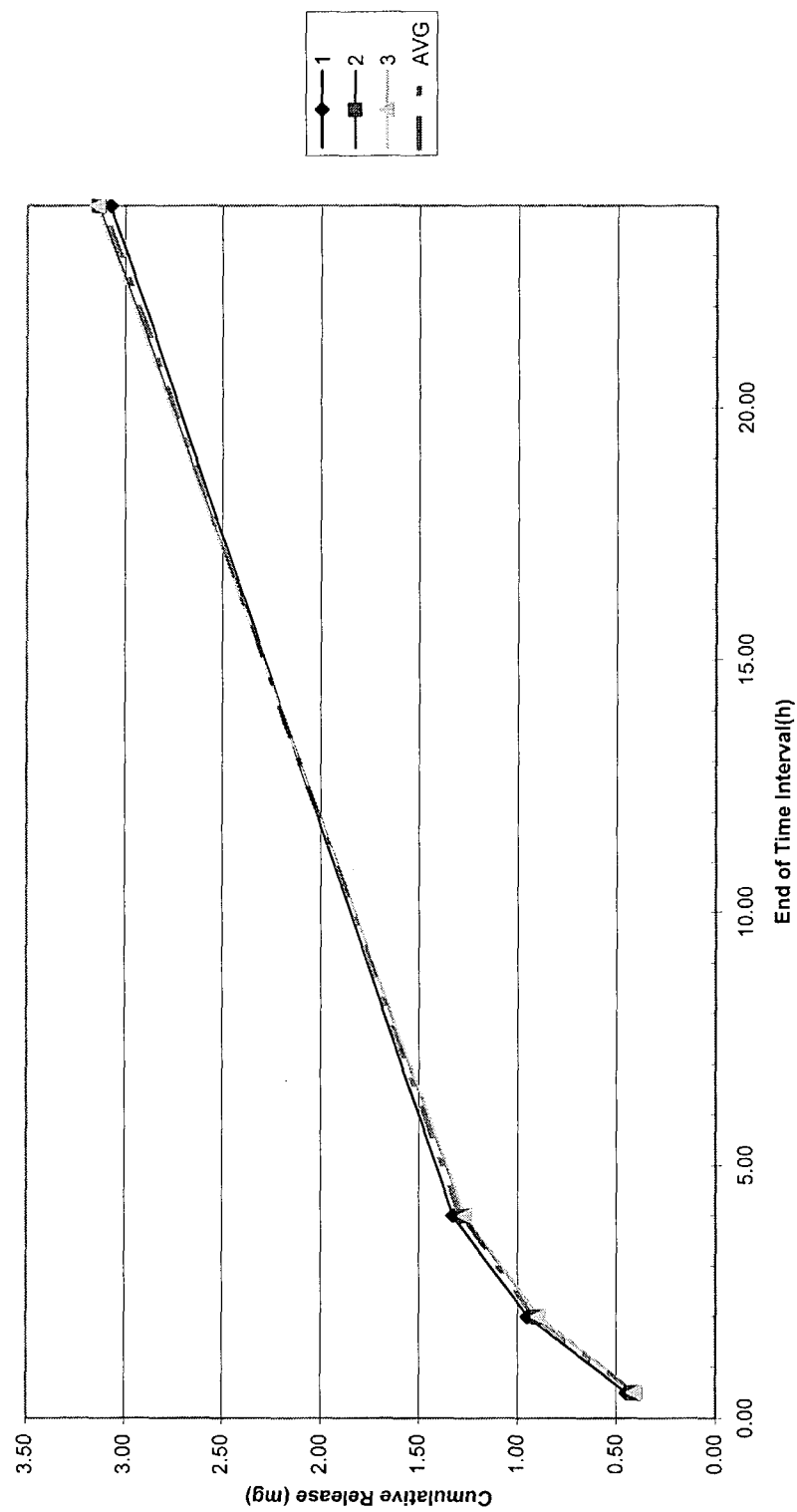

The release rate of antagonist into phosphate buffered medium is controlled by membrane selection or surfactant modification of the antagonist release controlling means. FIGS. 6-16 illustrate release rate profiles for various transdermal analgesic systems described in the Examples above. FIGS. 6, 7 and 8 illustrate the cumulative release of naltrexone from a Pluronic coated Solupor antagonist release controlling means. FIGS. 9 and 10 illustrate release rate and cumulative release of naltrexone, respectively, from a Celgard 3401 antagonist release controlling means. FIGS. 11 and 12 illustrate release rate and cumulative release of naltrexone, respectively, from an impermeable LDPE antagonist release controlling means. FIGS. 13 and 14 illustrate release rate and cumulative release of naltrexone, respectively, from a Celgard 3501 antagonist release controlling means. FIGS. 15 and 16 illustrate release rate and cumulative release of naltrexone, respectively, from a spun bonded polypropylene antagonist release controlling means. Each of FIGS. 9-16 illustrates data from triplicate experiments (#1, 2 and 3) and the average data.

Example 22

Extraction Studies

An unused, intact transdermal analgesic system (100 μg/h, 42 cm$^2$) was placed into standard extraction medium/solution (approximately 300 mL) equilibrated to the target temperature. Examples of standard extraction medium used include common household materials such as distilled water, vodka, rubbing alcohol, cooking oil, vinegar/water mixture and acetone. Aliquot of the extraction medium (1 mL) was removed at 0, 2, 5, 15, 60 and 120 minutes and diluted with unused extraction medium (5 mL). The samples were assayed for naltrexone and fentanyl content by HPLC. Extractions were conducted at 25° C. and repeated at 50° C. and 75° C. (where possible). The release rate ratio of antagonist to analgesic ranged from about less than 0.1:1 to about 3.6:1.

Example 23

Transdermal systems fabricated in Example 11 were adhered to a section of human epidermis that had been previously excised from the underlying dermis tissue using techniques known to those skilled in the art. The system/skin sandwich was placed in a Franz diffusion cell. The number of replicate samples was 12. The entire apparatus was immersed within a water bath thermostatted to 32° C. The receptor compartment of the cell was filled with aqueous phosphate buffer at pH 6.5. The receptor compartment was sampled at selected intervals over a three-day period. The solutions were assayed for fentanyl and naltrexone using sensitive HPLC assay techniques. Using the fentanyl/naltrexone concentration, diffusion area, sample volume and sampling time interval, the fentanyl/naltrexone flux was calculated. The results showed that after a transient start-up period, the mean flux of fentanyl was about 2 μg/h-cm$^2$, while the naltrexone flux was a value below the detection limit of the assay (i.e. <<0.1 μg/h-cm$^2$).

Example 24

Sensitization studies

Systems were prepared as follows:

Male hairless guinea pigs (Charles River Laboratories, Boston, Mass.) were used to assess the sensitization potential of a 48-hour dermal application of a transdermal system (2.5 cm$^2$). The transdermal system was composed of a skin adhesive (NS Duro-Tak 87-2287 or NS Duro-Tak 87-4287), a barrier film, a polymer with (transdermal analgesic system) and without (transdermal placebo system) naltrexone HCl, and a porous backing layer. Guinea pigs were divided into the following six groups:

TABLE 1

| Group | N | Induction Treatment and Challenge Treatments |
|---|---|---|
| 1 | 5 | Induction Treatment: Transdermal placebo system (2287 adhesive) Challenge Treatments: Transdermal placebo system (2287 adhesive) Transdermal analgesic system (2287 adhesive) |
| 2 | 5 | Induction Treatment: Transdermal placebo system (4287 adhesive) Challenge Treatments: Transdermal placebo system (4287 adhesive) Transdermal analgesic system (4287 adhesive) |
| 3 | 10 | Induction Treatment: Transdermal placebo system (2287 adhesive) Challenge Treatments: Transdermal placebo system (2287 adhesive) Transdermal analgesic system (2287 adhesive) |
| 4 | 10 | Induction Treatment: Transdermal placebo system (4287 adhesive) Challenge Treatments: Transdermal placebo system (4287 adhesive) Transdermal analgesic system (4287 adhesive) |
| 5 | 5 | Induction Treatment: 0.05% (w/v) 1-chloro 2-4dinitro benzene (DNCB) in acetone (positive control) Challenge Treatments: Acetone 0.05% DNCB |
| 6 | 5 | Naïve Control |

$^a$ Nominal concentration of naltrexone HCl per system = 3.44 mg

During the induction period, animals in Groups 1-5 received nine topical inductions to the dorsal skin area over 21 days (3 applications per week) of their respective test or control articles. Each application was worn for approximately 48 hours except for DNCB (positive control), which was worn for 24 hours. Prior to each dermal application and after system removal, the skin sites were wiped with an alcohol swab and blotted dry with a gauze pad. The margins of the skin application sites were marked with a skin-marking pen after system removal. For Groups 1-4, sites were evaluated for skin irritation 2±0.5 hours after system removal for the first induction, and 2±0.5 and 24±1 hours after system removal for the last induction. For Group 5, after removal of the first and last induction applications, sites were evaluated for primary and cumulative skin irritation, respectively, 2±0.5 and 24±1 hours after system removal.

Within approximately 10 to 14 days after the last induction application, each guinea pig was challenged according to the treatment presented in the table. Each topical application was worn for approximately 48 hours except for DNCB (positive control), which was worn for 24 hours. All application sites were scored for irritation approximately 2±0.5, 24±1, and 48±1 hours after removal of the challenge article. All scoring was conducted using a modified Draize scale (0-4 for erythema and 0-4 for edema). Responses were defined as positive for sensitization if the combined erythema and edema scores were ≧2 at 48 hours after challenge.

The mean irritation scores for the systems with the transdermal antagonist system (2287 adhesive) after the first and last induction applications were similar with no evidence of cumulative irritation and categorized the transdermal system as a mild irritant. The mean irritation scores for the transdermal antagonist system (4287 adhesive) after the first and last induction applications were similar with no evidence of cumulative irritation and categorized the transdermal system as a low-moderate irritant.

No evidence of sensitization was observed in any of the guinea pigs induced and challenged with the transdermal placebo system or transdermal antagonist system. This categorizes the transdermal systems as having a weak sensitization potential. A sensitization response was elicited in all of the guinea pigs induced and challenged with the positive control, DNCB, confirming that a response can be elicited in this model.

The manufacturer of the skin acrylate adhesives has also conducted safety tests on each adhesive, including a Buehler sensitization study. The data support the safe use of each adhesive.

A GLP study conducted in conscious hairless guinea pigs revealed intradermally injected or topically applied naltrexone gel as having a moderate to strong contact sensitization potential under the conditions of the study. A second GLP study was conducted in conscious hairless guinea pigs with transdermal placebo and antagonist systems. No evidence of sensitization was observed in any of the guinea pigs induced and challenged with the transdermal placebo systems or the transdermal antagonist systems. This categorizes the transdermal systems as having a weak sensitization potential. A sensitization response was elicited in all of the guinea pigs induced and challenged with the positive control, DNCB, confirming that a response can be elicited in this model (study details are presented below). Additional safety data on the skin acrylate adhesives used in these studies are available from the manufacturer. The data support the safe use in a clinical sensitization study of the transdermal systems with and without naltrexone in the backing.

Example 25

Skin Irritation Study

A GLP skin irritation study was conducted in conscious male hairless guinea pigs (strain IAF:HA-HO-hr) to evaluate the irritation potential of various sufentanil containing transdermal analgesic systems after a single 72-hour topical application. Two transdermal systems (having a thickness of 0.025 mm (1.0 mil) and 0.05 mm (2.0 mil)) composed of a skin adhesive (NS Duro-Tak 87-4287) containing sufentanil base, and a backing layer were tested (as described in Example 11). The in vitro flux of sufentanil base from both systems was approximately 0.60 μg/cm$^2$/hr. Each of the six guinea pigs had one system of each thickness applied to intact dorsal skin areas for 72 (±1) hours. The sites were scored for erythema, eschar, and edema at 30-40 minutes, 24 (±1), and 48 (±1) hours after the test articles were removed. Each application site was scored, using the Draize scale of 0-4 for erythema and 0-4 for edema. Primary Irritation Indices (PIIs) were calculated.

Mild irritation was observed after application of all systems. No changes in clinical condition occurred. The systems can be used in a single application human clinical study with a wearing period of up to 72 hours.

Example 26

Yucatan miniature swine were used to assess potential systemic toxicity following the intra-oral administration of a transdermal analgesic system. The transdermal system was composed of a skin adhesive (NS Duro-Tak 87-4287) with fentanyl, a barrier film, a polymer with naltrexone HCl, and a porous backing layer (as described in Example 14). The transdermal analgesic systems, with naltrexone HCl in the backing, contained approximately 8.8 mg of fentanyl per system and 35.2 mg of naltrexone HCl (0.4 mg/cm$^2$, in a 22 cm$^2$ system).

Healthy female Yucatan miniature swine, obtained from S&S Farms (Ranchita, Calif.), weighing 19-27 kg, and at least 6 months old, were used. The swine were identified by ear notches. Five animals were sedated and anesthetized with approximately 4 mg/kg of Telazol® and Isoflurane (for ear cannulation), respectively, and the systems were placed in their oral cavities for 11-30 minutes. Anesthesia was discontinued and the animals were allowed to recover. The animals were closely monitored for clinical signs.

The transdermal analgesic systems were removed from the oral cavity and allowed to air dry. Residual drug analysis was performed on all five transdermal antagonist systems administered. As tabulated in Table 2, both the fentanyl and the naltrexone were released out of the patch into the oral cavity. The release rate ratio of naltrexone to fentanyl was approximately about 6:1 to about 8:1. No fentanyl toxicity was observed in four out of the five animals dosed.

TABLE 2

Swine dosed with transdermal antagonist system

| Animal | Weight (kg) | Total Exposure Time (min) | Amount of Naltrexone delivered (mg) | Amount of fentanyl delivered (mg) | Release rate Ratio of Naltrexone: Fentanyl |
|---|---|---|---|---|---|
| 1 | 20.3 | 30 | 12.3 | 1.52 | 8:1 |
| 2 | 22.3 | 11 | 5.12 | 0.81 | 6:1 |
| 3 | 27.5 | 26 | 10.9 | 1.32 | 8:1 |
| 4 | 19.8 | 27 | 8.24 | 1.28 | 6:1 |
| 5 | 23 | 20 | 10.78 | 1.38 | 8:1 |

Example 27

Sufentanil/Naltrexone Ratio Study in Rats

Groups of male rats (CRL:CD® (SD) IGSBR) were administered the following test agents intravenously via a tail vein: naltrexone hydrochloride alone, sufentanil alone, or naltrexone hydrochloride followed immediately by sufentanil. The objective of the study was to determine doses of naltrexone that would effectively antagonize the severe opioid effect profile induced by a pre-selected intravenous dose of sufentanil (18.75 μg/kg). The dose groups are summarized in the table below.

TABLE 3

| Naltrexone[1] | Sufentanil[1] | Naltrexone/ Sufentanil Ratio | Number of Rats |
|---|---|---|---|
| — | 18.75 | NA | 8 |
| 300 | — | NA | 3 |
| 300 | 18.75 | 16:1 | 4 |
| 150 | 18.75 | 8:1 | 4 |
| 75 | 18.75 | 4:1 | 4 |
| 18.75 | 18.75 | 1:1 | 4 |

[1] = (μg/kg iv)

Figure 17:
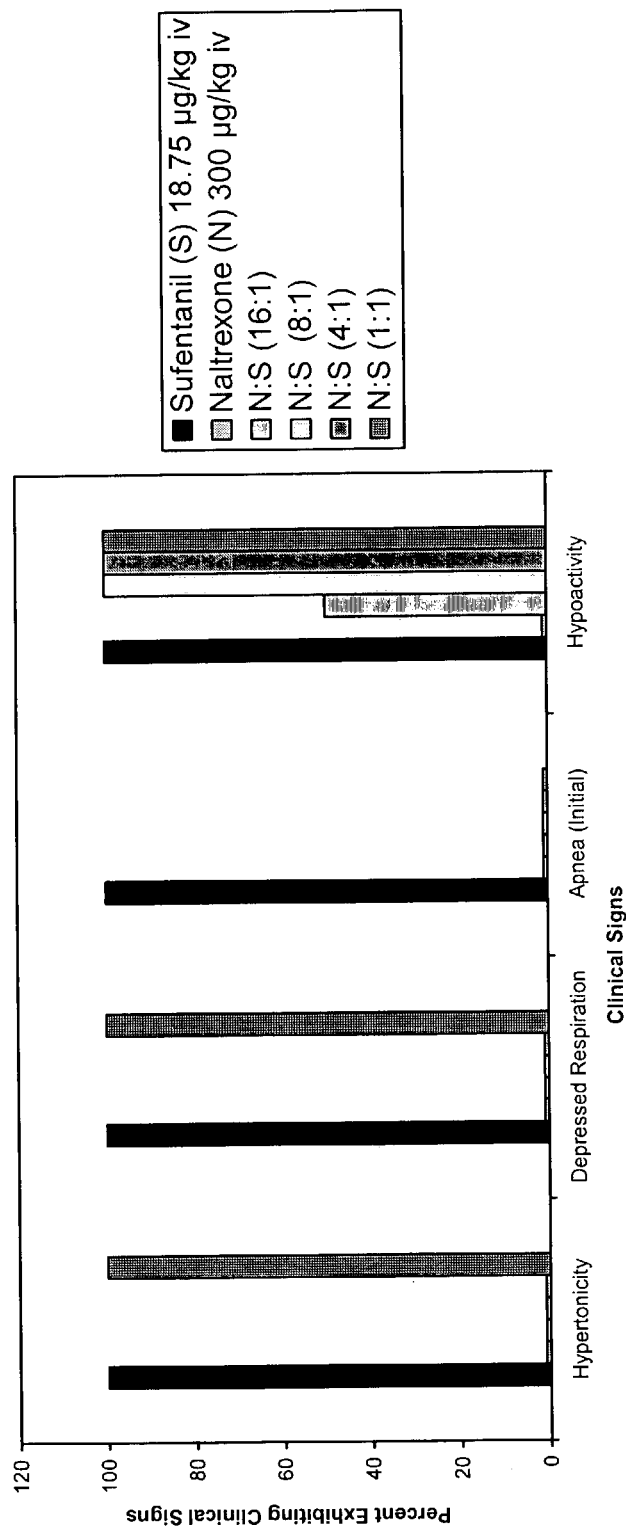
FIGS. 17 and 18 illustrate the effect of naltrexone on sufentanil-induced clinical signs in rats within 30 minutes after dosing.
Figure 18:
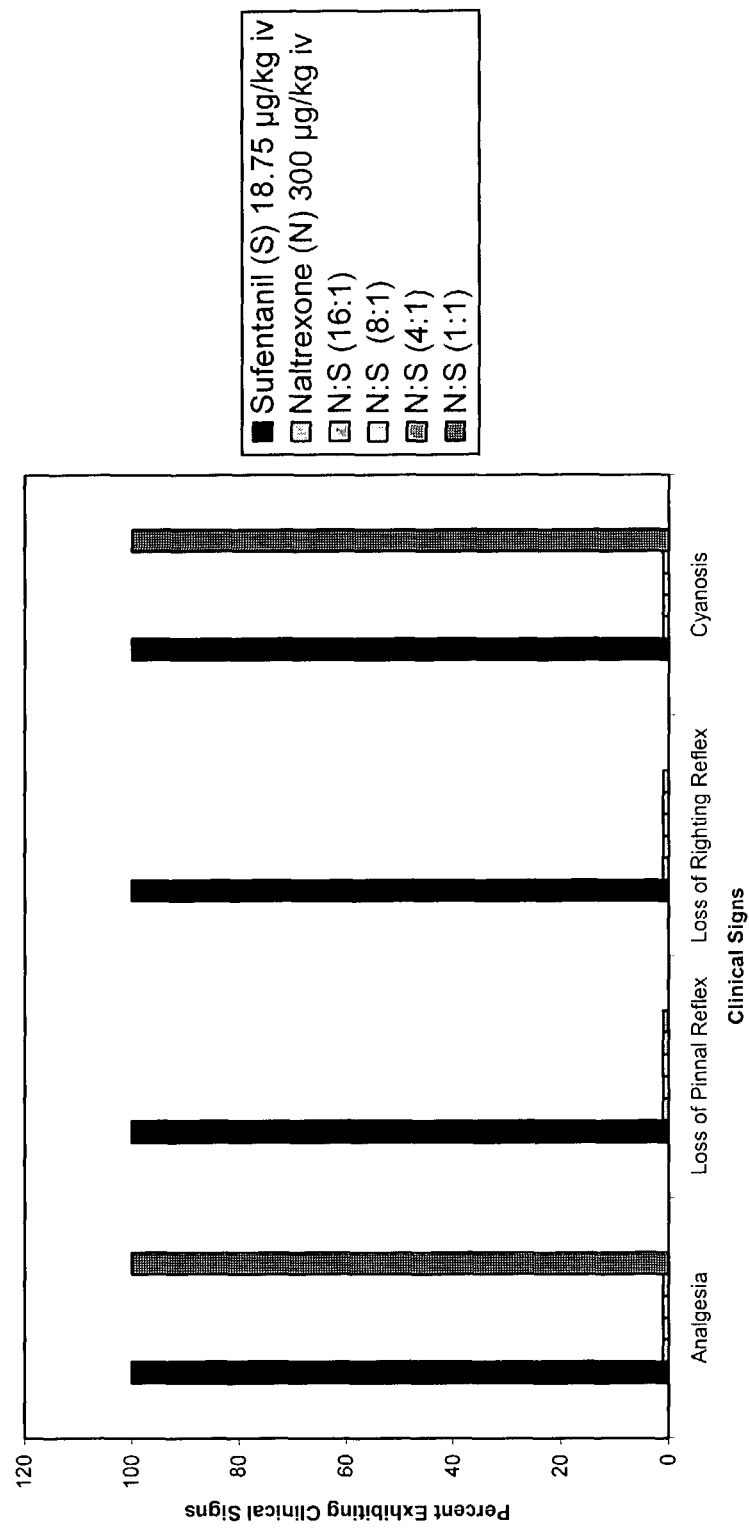

Following injection of test agents, animals were observed for clinical signs. Naltrexone was effective in blocking opioid-induced effects of sufentanil at naltrexone: sufentanil dose ratios of 4:1, 8:1, and 16:1. Duration of naltrexone antagonism was comparable at each of the three dose ratios and appeared to last as long as clinical signs persisted in the sufentanil control group (generally 1-2 hours). The 1:1 naltrexone:sufentanil dose ratio was less effective in blocking sufentanil-induced clinical signs, but at this dose ratio clinical signs were generally less severe and shorter lasting than in the sufentanil control group. Naltrexone (300 μg/kg) administered alone to rats (N=3) produced no apparent effects. FIGS. 17 and 18 illustrate the effect of naltrexone on sufentanil-induced clinical signs in rats (within 30 minutes after dosing).

Example 28

Evaluation of the Contact Sensitization Potential Transdermal Systems in Healthy Subjects The contact sensitization potential of the components of transdermal analgesic system in healthy subjects were conducted using various transdermal antagonist patches as described in Example 11 above: System A: transdermal analgesic system (placebo) with naltrexone (44 cm$^2$); and System B: transdermal analgesic system (placebo) (44 cm$^2$). A secondary objective was to demonstrate non-quantifiable serum naltrexone concentrations.

The study was a single center, double blind, randomized study with Induction, Rest, and Challenge Phases. In the present study, 240 subjects received system A and 60 subjects received system B. System A (transdermal placebo analgesic system with naltrexone) contains a polyester release liner, a polyacrylate adhesive, and a polyester backing laminated to a polyethylene film with a naltrexone-polyethylene layer. System B (transdermal placebo analgesic system without naltrexone) contains a polyester release liner, a polyacrylate adhesive, and a polyester backing laminated to a polyethylene film with a polyethylene layer.

During the Induction Phase, each subject received either system A or system B, for a total of nine consecutive systems applied to the same skin site over a total of 21 days. If the application site had to be changed due to severe skin reactions from a previous system application, a different site on the same arm was used to continue with the 21-day application plan. Each system was worn continuously for two or three days (48 or 72 hours)±4 hours. The system was applied to skin sites on the upper outer arm. Immediately following removal of each Induction Phase system, and 24 hours after the removal of the last Induction Phase system, the application site was assessed for topical reactions using a standard grading scale.

During the Rest Phase, which commenced after the Induction Phase, there was no application for two weeks. During the Challenge Phase, which commenced after the Rest Phase, two systems (one A and one B) were applied to naive skin sites on the upper outer arm not used in the Induction Phase and worn for 48 hours. After removal of the Challenge Phase transdermal analgesic systems, the skin sites were assessed for topical irritation and sensitization reactions at 0.5, 24, 48, and 72 hours after removal. Any questionable sensitization reaction was confirmed by a re-challenge that was applied to new sites 24 hours after removal of the first Challenge Phase systems. Two systems (one A and one B) were applied to naive skin sites on the upper outer arm not used in the Induction Phase (or on upper chest if necessary) at the 24-hour assessment of the first challenge and worn for 48 hours. They were removed and follow-up assessments were performed at 0.5, 24, 48, and 72 hours post-removal. Following removal of each Induction Phase system, the application site was assessed for topical reactions and adherence, using standard grading scales.

Blood samples were drawn for analysis of naltrexone concentrations before system application on day 1 and before the removal of the system on days 17, 19, and 22. The serum was removed from the blood samples using standard procedures. Serum samples were analyzed using a validated liquid chromatography-tandem mass spectrometry (LC/MS/MS) method. The lower limit of quantitation was approximately 5 pg/mL.

The transdermal analgesic systems demonstrated acceptable levels of adhesion and irritation. No evidence of sensitization was observed. The naltrexone concentration in majority of the serum samples was below quantifiable limits. Accordingly, there was no evidence of systemic administration of naltrexone.

Example 29

Activity Studies

The primary objective of this study was to evaluate serum naltrexone concentrations following application of a transdermal analgesic placebo system with naltrexone system under various conditions (normal activity, showering and physical exercise).

The secondary objective was to evaluate residual naltrexone in the used systems following a 4 hour wear period under various conditions (normal activity, showering and physical exercise).

The study was a randomized, single-center, open-label, three 4-hour period, two-sequence crossover study. Subjects were randomly assigned to one of two treatment sequences. All three periods took place on the same day. During each period, each subject wore one new transdermal analgesic placebo system with naltrexone (44 cm$^2$) system for 4 hours and engaged in normal activity; strenuous physical activity (20 minutes, room temperature), or take a warm shower (10 minutes at approximately 40° C.). The normal activity was first while the order of the other two activities was randomized.

Blood samples were collected for determination of serum naltrexone concentrations before the first system application, then at 2, 4, 5, 6, 7, 8, 9, 10, 11, 12, 13 hours following system application. During the exercise and shower activities, an additional blood sample was taken following the completion of the activity. Serum samples were analyzed for determination of naltrexone concentration using a validated liquid chromatography-tandem mass spectrometry (LC/MS/MS) method. The lower limit of quantitation was approximately 5 pg/mL.

The adherence of each transdermal analgesic system was assessed just prior to removal of the system. Each skin site to which a system was applied was monitored for topical reactions (including erythema, edema, pustules, papules and itching) approximately 15 minutes, one hour, and 16-24 hours after removal.

The residual naltrexone in the used systems was measured after the system was removed. The analysis method for naltrexone in used systems was preformed as follows. The systems were first weighed, removed from the protective liner and placed onto nylon netting, then rolled and placed into the extraction vessel. Extraction was performed using an organic solvent with shaking, followed by dilution with an organic solvent/water mixture. The naltrexone was measured using reversed-phase HPLC with UV detection.

The percent loss of naltrexone content from the transdermal system averaged about 2-3% during normal and strenuous physical activity. During the showering activity, the percent loss of naltrexone content from the transdermal system averaged about 23%. The naltrexone concentration in majority of the serum samples was below quantifiable limits. Accordingly, there was no evidence of systemic administration of naltrexone. Additionally, the transdermal analgesic systems demonstrated acceptable levels of adhesion and irritation. No evidence of sensitization was observed.

Example 30

Bioequivalence study

The in vivo fentanyl flux studies were conducted using various transdermal fentanyl systems—transdermal analgesic system as described in Example 14, and DUROGESIC™ fentanyl system, and the comparative pharmacokinetic parameters are tabulated in Table 4 and 5 below. The pharmacokinetic parameters of the transdermal analgesic systems were evaluated as follows.

A single-center, randomized, single-application, open-label, two-treatment, two-sequence, two-period, cross-over study using transdermal systems, each for 72 hour application: Treatment Durogesic™ 50 μg/h; and Treatment B (transdermal fentanyl system with naltrexone (50 μg/h of fentanyl) was performed to evaluate the pharmacokinetics of the systems after single application.

Subjects were randomly assigned to one of two treatment sequences (at least 14 subjects per treatment sequence). Subjects wore two transdermal fentanyl systems sequentially over two 72-hour wearing periods on a skin site on the upper outer arm. There was a minimum washout period of at least 14 days and not more than 21 days between treatments. The washout period commenced upon removal of the study system. The study system was worn for 72 hours. Each subject received a bolus naloxone (0.5 mg) followed by continuous naloxone infusion (0.2 mg/h) as the opioid antagonist starting 15 minutes prior to system application and during application and through 4 hours post system removal. Each subject then received naltrexone 50 mg tablets at 6 and 20 hours post system removal.

At scheduled time points for both treatments (pre-dose and 2, 3, 5, 8, 12, 18, 24, 30, 36, 42, 48, 54, 60, 66, 72, 73, 74, 76, 80, 84, 96, 108, and 120 hours following system application), blood samples were collected from each subject for determination of serum fentanyl concentrations. Serum samples were analyzed for determination of fentanyl concentration using a validated liquid chromatography-tandem mass spectrometry (LC/MS/MS) method. Topical skin irritation and system adhesion were assessed at scheduled time points.

Figure 19:
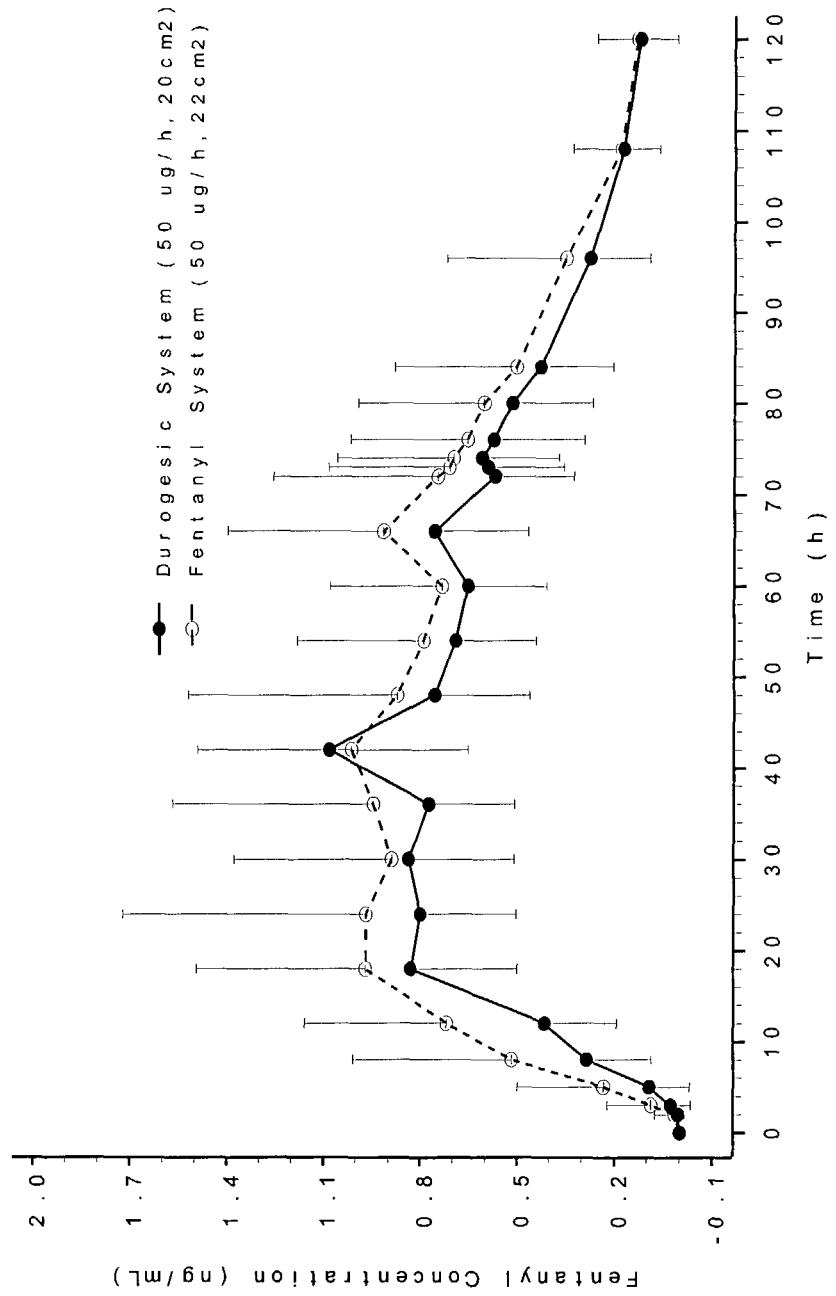
FIG. 19 illustrates serum fentanyl concentrations following transdermal application of various fentanyl systems for 72 hours, over a period of 120 hours post application.

The results of the in vivo study are tabulated in Tables 4 and 5. FIG. 19 illustrates serum fentanyl concentrations following transdermal application of various fentanyl systems—one application of transdermal analgesic system of the invention (50 μg/h, 22 cm$^2$); and DUROGESIC™ fentanyl system (50 μg/h, 20 cm$^2$), up to 120 hours after first administration.

Descriptive statistics were calculated for fentanyl pharmacokinetic parameters for each treatment. Characteristics of these concentration-time curves, such as the area under the serum drug concentration-time curve (AUC), time to maximum concentration ($T_{max}$), and the peak blood, plasma or serum concentration ($C_{max}$) of the drug, were examined by statistical procedures as described earlier. A mixed-effect analysis of variance (ANOVA) model which includes treatment, period, sequence, fixed effects and subject-within-sequence random effect was used for the analysis of fentanyl pharmacokinetic parameters (log transformed $AUC_{inf}$ and $C_{max}$, Statistical methods for average bioavailability. (Design and Analysis of Bioavailability and Bioequivalence Studies. S. Chow and J. Liu (eds), Marcel Dekker, New York, N.Y., 1992, pp 70-125). The ratios of the least square estimate of the mean parameters and their 90% confidence intervals (Schuirmann D. J., A comparison of the two one-sided tests procedure and the power approach for assessing the equivalence of average bioavailability; J. Pharmacokinet. Biopharm. 1987, 15: 657-680) were calculated. The lower and upper bounds of the 90% confidence intervals were compared to 80% and 125%, respectively. A non-parametric Wilcoxon rank-sum test was performed on both fentanyl $T_{max}$ and fentanyl fractional cumulative AUCs. A significance level of 0.05 was used for these tests. The test and the reference formulation/composition were considered bioequivalent if the confidence interval around the ratio of the mean (test/reference product i.e. Treatment A/Treatment B) value for a pharmacokinetic parameter is no less than 80% on the lower end and no more than 125% on the upper end. The results of the statistical analysis of log transformed pharmacokinetic (PK) parameters are tabulated in Tables 4 and 5.

TABLE 4A

Comparative Pharmacokinetic (PK) Parameters for transdermal fentanyl containing analgesic system and DUROGESIC ™ fentanyl system

| Dose (μg/h) | Size (cm$^2$) | Fentanyl content (mg) | $C_{max}$ (ng/ml) | Standardized $C_{max}$ (ng/ml-cm$^2$) | Normalized $C_{max}$ (ng/ml-(mg/h)) |
|---|---|---|---|---|---|
| DUROGESIC ™ | | | | | |
| 25 | 10 | 2.5 | 0.6 | 0.06 | 24 |
| 50 | 20 | 5.0 | 1.4 | 0.07 | 28 |
| 75 | 30 | 7.5 | 1.7 | 0.05 | 22.7 |
| 100 | 40 | 10.0 | 2.5 | 0.06 | 25 |
| Transdermal fentanyl systems | | | | | |
| 12.5 | 5.5 | 2.2 | 0.29 | 0.052 | 23 |
| 25 | 11 | 4.4 | 0.58 | 0.052 | 23 |
| 50 | 22 | 8.8 | 1.15 | 0.052 | 23 |
| 75 | 33 | 13.2 | 1.73 | 0.052 | 23 |
| 100 | 44 | 17.6 | 2.30 | 0.052 | 23 |

TABLE 4B

Mean (CV %$^a$) pharmacokinetic parameters for Transdermal Fentanyl Systems

| PK Parameter | Treatment A (n = 26) DUROGESIC ™ (50 μg/h, 20 cm$^2$) | Treatment B (n = 26) Fentanyl containing analgesic system (50 μg/h, 22 cm$^2$) |
|---|---|---|
| $C_{max}$ (ng/mL) | 1.15 (36) | 1.25 (55) |
| $T_{max}$ (h) | 39.0 (36) | 40.1 (52) |
| $AUC_{0-120}$ (ng/mL · h) | 63.5 (36) | 75.3 (60) |
| $AUC_{inf}$ (ng/mL · h) | 68.7 (41) | 81.4 (62) |
| Half-life (h) | 22.2 (36) | 22.2 (36) |

$^a$ = percent coefficient of variation

TABLE 5

Bioequivalence analysis of pharmacokinetic parameters (n = 26)

| PK Parameter | Ratio (%) | 90% confidence interval | |
|---|---|---|---|
| | | Lower | Upper |
| Ln $C_{max}$ | 101.84 | 92.37 | 112.28 |
| Ln $AUC_{inf}$ | 110.27 | 102.61 | 118.51 |

Contrast is for Treatment B/Treatment A

Thus, as evidenced from the results tabulated above and illustrated in FIG. 19, the transdermal fentanyl containing analgesic systems of the present invention comprising naltrexone, are bioequivalent products to the rate-controlled, saturated DUROGESIC™ fentanyl system. In particular, the transdermal analgesic system according to the invention display pharmacokinetic dynamic parameters comparable to the transdermal DUROGESIC™ fentanyl system: the 90% confidence interval for the average log transformed Cmax and average ratios of the test formulation versus the reference formulation fell within the 80% to 120% range.

Example 31

The in vivo fentanyl flux studies were conducted using various transdermal fentanyl systems—transdermal antagonist system as described in Example 15, and DUROGESIC™ fentanyl system, with the following exceptions.

The serum samples collected at and before 76 hours post-application were also analyzed for naltrexone concentration (Treatment B) using a validated liquid chromatography-tandem mass spectrometry (LC/MS/MS) method.

TABLE 6A

Comparative Pharmacokinetic (PK) Parameters for transdermal fentanyl containing analgesic system and DUROGESIC ™ fentanyl system

| Dose (μg/h) | Size (cm²) | Fentanyl content (mg) | $C_{max}$ (ng/ml) | Standardized $C_{max}$ (ng/ml-cm²) | Normalized $C_{max}$ (ng/ml-(mg/h)) |
|---|---|---|---|---|---|
| DUROGESIC ™ | | | | | |
| 25 | 10 | 2.5 | 0.6 | 0.06 | 24 |
| 50 | 20 | 5.0 | 1.4 | 0.07 | 28 |
| 75 | 30 | 7.5 | 1.7 | 0.05 | 22.7 |
| 100 | 40 | 10.0 | 2.5 | 0.06 | 25 |
| Transdermal fentanyl systems | | | | | |
| 12.5 | 5.25 | 2.1 | 0.29 | 0.054 | 22.6 |
| 25 | 10.5 | 4.2 | 0.57 | 0.054 | 22.6 |
| 50 | 21 | 8.4 | 1.13 | 0.054 | 22.6 |
| 75 | 31.5 | 12.6 | 1.70 | 0.054 | 22.6 |
| 100 | 42 | 16.8 | 2.26 | 0.054 | 22.6 |

TABLE 6B

Summary of mean (CV %$^a$) pharmacokinetic parameters

| PK Parameter | Treatment A (n = 28) DUROGESIC ™ (100 μg/h, 40 cm²) | Treatment B (n = 28) Fentanyl containing analgesic system (100 μg/h, 42 cm²) |
|---|---|---|
| $C_{max}$ (ng/mL) | 2.26 (36) | 2.47 (47) |
| $T_{max}$ (h) | 48 (40) | 37.6 (57) |
| $AUC_{0-120}$ (ng/mL · h) | 133.7 (24) | 143.5 (26) |
| $AUC_{inf}$ (ng/mL · h) | 143 (26) | 158.6 (28) |
| Half-life (h) | 19.4 (22) | 26.7 (131) |

$^a$ = percent coefficient of variation

TABLE 7

Bioequivalence analysis of pharmacokinetic parameters (n = 28)

| | | 90% confidence interval | |
|---|---|---|---|
| PK Parameter | Ratio (%) | Lower | Upper |
| Ln $C_{max}$ | 106.74 | 96.94 | 117.53 |
| Ln $AUC_{inf}$ | 110.24 | 103.48 | 117.43 |

Contrast is for Treatment B/Treatment A

Figure 20:
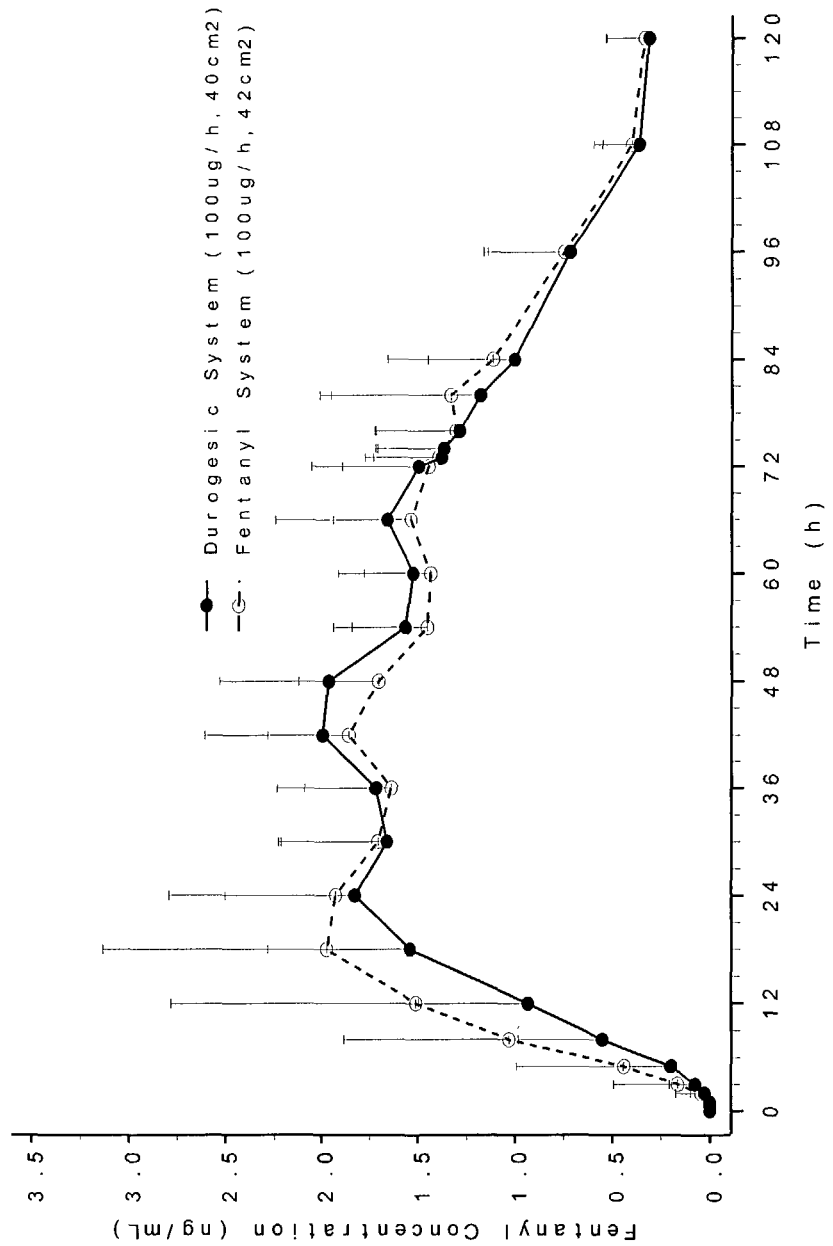
FIG. 20 illustrates serum fentanyl concentrations following transdermal application of various fentanyl systems for 72 hours, over a period of 120 hours post application.

Thus, as evidenced from the results tabulated above and illustrated in FIG. 20, the transdermal analgesic system of the present invention comprising a drug reservoir comprising fentanyl, are bioequivalent products to the rate-controlled, saturated DUROGESIC™ fentanyl system. In particular, the transdermal analgesic system according to the invention display pharmacokinetic dynamic parameters comparable to the transdermal DUROGESIC™ fentanyl system: the 90% confidence interval for the average log transformed Cmax and average ratios of the test formulation versus the reference formulation fell within the 80% to 120% range. Additionally, naltrexone concentration in the serum samples were below the detectable levels, indicating that there was no systemic absorption of naltrexone from the transdermal analgesic systems.

Example 32

Pharmacokinetic Studies for Transdermal Sufentanil Containing Systems

A single-center, randomized, open-label, three-treatment, two-sequence, three-period, cross-over study in healthy subjects using IV administration and transdermal systems was performed to estimate the amount of sufentanil absorbed from two transdermal sufentanil containing analgesic systems of different thickness compared with intravenous sufentanil administration, and to compare the pharmacokinetics of the two transdermal sufentanil systems. The following treatments were administered during this study: Treatment A: Continuous IV sufentanil infusion delivering 100 μg sufentanil at a rate of 10 μg/h (10 hour infusion); Treatment B: transdermal sufentanil containing analgesic system (6 mg, 20 cm², 0.05 mm adhesive thickness, approximately 10 μg/h, 72 hour application); and Treatment C: transdermal sufentanil containing analgesic system (3 mg, 20 cm², 0.025 mm adhesive thickness, 10 μg/h, 72 hour application).

Subjects were randomly assigned to one of two treatment sequences. Each subject received a continuous IV sufentanil infusion at 10 μg/h for 10 hours in the first period. Following this, each subject received two 72-hour transdermal systems, one system during treatment period 2 and one during treatment period 3, on naive skin sites on the upper outer arm. There was a minimum washout period of at least 6 days and not more than 14 days between treatments. The washout period commenced upon removal of the transdermal applications or termination of the IV infusion. Each subject received naltrexone 50 mg tablets as the opioid antagonist starting 14 hours before system application/IV infusion initiation. Subjects continued to receive naltrexone 50 mg tablets twice daily during system application/IV infusion and through 24 hours post system removal/IV infusion termination.

Figure 21:
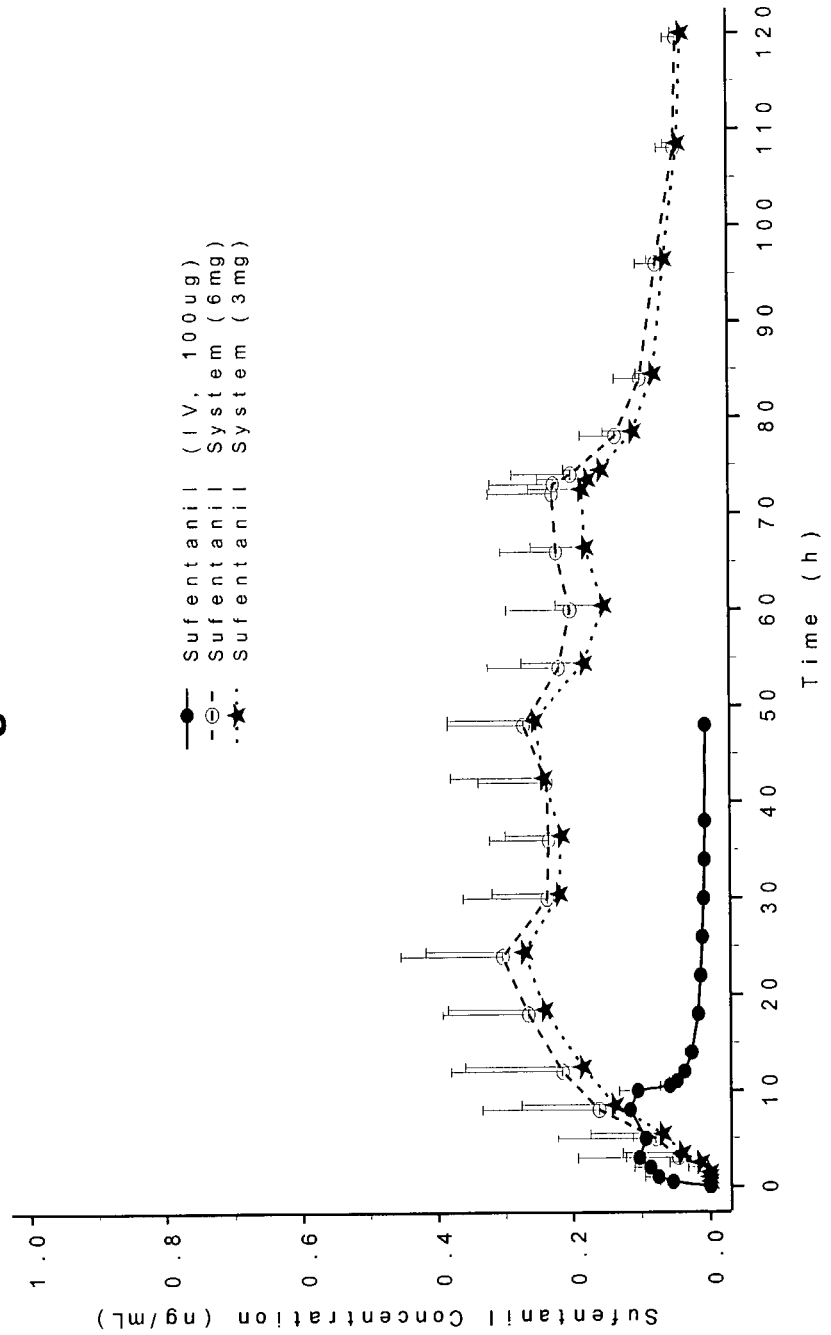
FIG. 21 illustrates plasma sufentanil concentrations following various sufentanil treatments, up to 120 hours after first administration.

At scheduled time points following IV infusion/system application, blood samples were collected for determination of plasma sufentanil concentrations. During the IV treatment at pre-dose and 0.5, 1, 2, 3, 5, 8, 10, 10.5, 11, 12, 14, 18, 22, 26, 30, 34, 38, and 48 hours following infusion initiation. During each transdermal treatment at pre-dose and 0.5, 1, 2, 3, 5, 8, 12, 18, 24, 30, 36, 42, 48, 54, 60, 66, 72, 73, 74, 78, 84, 96, 108, and 120 hours following system application. Plasma samples were analyzed for determination of sufentanil concentration using a validated liquid chromatography-tandem mass spectrometry (LC/MS/MS) method. The Residual Sufentanil Content in the systems is measured using reversed-phase HPLC with UV detection. Topical skin irritation and system adherence was assessed for the transdermal treatments. Adverse events, blood pressure, temperature, heart rate and respiratory rate were monitored. The results of the study are tabulated in Table 8. FIG. 21 illustrates plasma sufentanil concentrations following various sufentanil treatments, up to 120 hours after first administration.

Descriptive statistics were calculated for sufentanil pharmacokinetic parameters for each treatment (A, B, and C) according to the statistical methods described in the examples above.

TABLE 8

Summary of mean (CV %) pharmacokinetic parameters

| PK Parameter | Treatment B (n = 18) sufentanil systems (6 mg, 20 cm², 0.05 mm) | Treatment C (n = 18) sufentanil systems (3 mg, 20 cm², 0.025 mm) |
| --- | --- | --- |
| $C_{max}$ (ng/mL) | 0.34 (44) | 0.31 (51) |
| $T_{max}$ (h) | 29.3 (46) | 32.0 (46) |
| $AUC_{0-120}$ (ng/mL · h) | 19.6 (45) | 17.3 (45) |
| $AUC_{inf}$ (ng/mL · h) | 21.6 (44) | 19 (44) |
| Half-life (h) | 30.5 (40) | 30.3 (38) |

TABLE 6A

Comparative Pharmacokinetic (PK) Parameters for transdermal sufentanil containing analgesic system

| Input Rate (mg/h) | Size (cm²) | Sufentanil content (mg) | $C_{max}$ (ng/ml) | Standardized $C_{max}$ (ng/ml-cm²) | Normalized $C_{max}$ (ng/ml-(mg/h)) |
| --- | --- | --- | --- | --- | --- |
| 10 | 20 | 6 | 0.34 | 0.017 | 34 |
| 10 | 20 | 3 | 0.31 | 0.015 | 31 |
| 7.5 | 15 | 6 | 0.26 | 0.017 | 34 |
| 5 | 10 | 6 | 0.17 | 0.017 | 34 |
| 2.5 | 5 | 6 | 0.08 | 0.017 | 34 |
| 1.25 | 2.5 | 6 | 0.05 | 0.017 | 34 |

The present invention is described and characterized by one or more of the following features and/or characteristics, either alone or in combination with one or more of the other features and characteristics: A transdermal system for administering an analgesic through the skin, the system having a reduced potential for abuse, comprising:

(a) an analgesic reservoir comprising an analgesic, the analgesic being selected from the group consisting of fentanyl and analogs thereof;

(b) an antagonist reservoir comprising an antagonist for said analgesic;

(c) a barrier layer, said barrier layer separating said antagonist reservoir from said analgesic reservoir, said barrier layer being substantially impermeable to said analgesic and to said antagonist, wherein the system (i) substantially prevents release of the antagonist from the system upon securing the system to a human patient for a period of up to about 7 days; and (ii) provides release of the antagonist at a rate sufficient to provide an abuse limiting release rate ratio of the antagonist to the analgesic when the dosage form is subject to abuse, e.g., upon ingestion or substantial immersion of the system in the solvent. The transdermal analgesic system of the invention comprises an analgesic reservoir comprising an amount of analgesic sufficient to induce and maintain analgesia in a human patient for a period of at least three days, wherein the analgesic is fentanyl or an analog thereof and the analog is selected from the group consisting of alfentanil, lofentanil, remifentanil, sufentanil and trefentanil. In preferred embodiments, the analgesic is fentanyl or sufentanil, more preferably, base form of fentanyl or sufentanil. The analgesic reservoir comprises a polymeric matrix comprising about 1 wt % to about 20 wt % of the analgesic, and optionally a permeation enhancer. The analgesic reservoir may comprise a single phase formulation free of undissolved components; or an aqueous gel comprising up to about 20 wt % of the analgesic, about 50 wt % permeation enhancer, and about 0.5 to about 10 wt % gelling agent. Additionally, the transdermal analgesic system of the invention further comprises an analgesic release rate controlling means disposed between the analgesic reservoir and the skin.

In additional aspects, the transdermal analgesic system of the invention comprises an antagonist reservoir comprising an antagonist in a form that is not releasable through the barrier layer, the antagonist being releasable from system when the dosage form is subject to abuse, e.g., upon being ingested or substantially immersed in a solvent. Preferably, the antagonist reservoir comprises the antagonist dispersed within a polymer, wherein the antagonist is substantially insoluble in the antagonist reservoir polymer. The antagonist is selected from the group consisting of naltrexone, methylnaltrexone, naloxone, nalbuphine, nalorphine, nalorphine dinicotinate, nalmefene, nadide, levallorphan, cyclozocine and pharmaceutically acceptable salts thereof. In preferred embodiments, the antagonist is present as a salt, preferably as a hydrochloride salt of an antagonist base.

In additional aspects, the transdermal analgesic system of the invention comprises a barrier layer impermeable to the analgesic and the antagonist; wherein the barrier layer comprises a material which is insoluble in water, alcohol and organic solvents. The antagonist reservoir is disposed on the skin distal surface of the barrier layer and the analgesic reservoir is disposed on the skin proximal surface of the barrier layer.

In additional aspects, the transdermal analgesic system of the invention further comprises an antagonist release rate controlling means, wherein said antagonist release rate controlling means substantially prevents release of the antagonist from the system upon securing the system to a human patient for a period of up to about 7 days; and provides release of the antagonist at a rate sufficient to provide an abuse limiting release rate ratio of the antagonist to the analgesic when the dosage form is subject to abuse, e.g., upon ingestion or substantial immersion of the system in the solvent. The antagonist release rate controlling means is disposed on the skin distal surface of the antagonist reservoir.

In another aspect, the transdermal analgesic system of the invention, when the dosage form is subject to abuse, e.g., upon ingestion or immersion in a solvent for a period of time, substantially continuously provides a release rate ratio of the antagonist to the analgesic of at least about 0.5:1 to about 20:1; preferably 1:1 to about 16:1, more preferably about 1.5:1 to about 8:1; and even more preferably 2:1 to about 4:1, wherein the period of time of immersion is up to about 1 minute to about 24 hours.

In another aspect, the invention relates to a transdermal system for administering an analgesic through the skin, the system having a reduced potential for abuse, comprising:

(a) an analgesic reservoir comprising an amount of analgesic sufficient to induce and maintain analgesia in a human patient for a period of at least three days, wherein the analgesic is fentanyl or an analog thereof and the analog is selected from the group consisting of alfentanil, lofentanil, remifentanil, sufentanil and trefentanil;

(b) an antagonist reservoir comprising an antagonist for said analgesic, wherein the antagonist in a form that is not releasable through the barrier layer, the antagonist being releasable from system upon being ingested or substantially immersed in a solvent, and further wherein the antagonist is selected from the group consisting of naltrexone, methylnaltrexone, naloxone, nalbuphine, nalorphine, nalorphine dinicotinate, nalmefene, nadide, levallorphan, cyclozocine and pharmaceutically acceptable salts thereof;
(c) a barrier layer, said barrier layer separating said antagonist reservoir from said analgesic reservoir, said barrier layer being substantially impermeable to said analgesic and to said antagonist; and
(d) an antagonist release rate controlling means disposed on the skin distal surface of the antagonist reservoir, wherein said antagonist release rate controlling means substantially prevents release of the antagonist from the system upon securing the system to a human patient for a period of up to about 7 days, and further wherein the antagonist release rate controlling means provides release of the antagonist at a rate sufficient to provide an abuse limiting release rate ratio of the antagonist to the analgesic when the dosage form is subject to abuse, e.g., upon ingestion or substantial immersion of the system in the solvent.

The above-described exemplary embodiments are intended to be illustrative in all respects, rather than restrictive, of the present invention. Thus the present invention is capable of many variations in detailed implementation that can be derived from the description contained herein by a person skilled in the art. All such variations and modifications are considered to be within the scope and spirit of the present invention.

We claim:

1. A transdermal system for administering an analgesic through the skin, the system having a reduced potential for abuse and including a multilaminate comprising:
(a) an analgesic reservoir comprising an analgesic, the analgesic being selected from the group consisting of fentanyl and analogs thereof;
(b) an antagonist reservoir layer comprising an antagonist for said analgesic, the antagonist reservoir layer comprising an external edge of the system;
(c) a barrier layer, said barrier layer separating said antagonist reservoir layer from said analgesic reservoir, said barrier layer being impermeable to said analgesic and to said antagonist, wherein the system (i) has an antagonist release rate controlling layer that substantially prevents release of the antagonist from the system upon securing the system to a human patient for a period of up to about 7 days; and (ii) provides release of the antagonist at a rate sufficient to provide an abuse limiting release rate ratio of the antagonist to the analgesic when the system is subject to abuse, such that the antagonist reservoir layer releases the antagonist through the external edge of the antagonist reservoir layer.

2. A transdermal system for administering an analgesic through the skin, the system having a reduced potential for abuse and including a multilaminate comprising:
(a) an analgesic reservoir comprising an analgesic, the analgesic being selected from the group consisting of fentanyl and analogs thereof;
(b) an antagonist reservoir layer comprising an antagonist for said analgesic, the antagonist reservoir layer comprising an external edge of the system;
(c) a barrier layer, said barrier layer separating said antagonist reservoir layer from said analgesic reservoir, said barrier layer being impermeable to said analgesic and to said antagonist, wherein the system (i) has an antagonist release rate controlling layer that substantially prevents release of the antagonist from the system upon securing the system to a human patient for a period of up to about 7 days; and (ii) provides release of the antagonist at a rate sufficient to provide an abuse limiting release rate ratio of the antagonist to the analgesic upon ingestion or substantial immersion of the system in a solvent, such that the antagonist reservoir layer releases the antagonist through the external edge of the antagonist reservoir layer.

3. The system of claim 1 wherein the antagonist release rate controlling layer is selected from a group consisting of a membrane, a film, a coating, a sheet, and a deposit on the antagonist reservoir layer.

4. The system of claim 3 wherein the antagonist release rate controlling layer is selected from a group consisting of film, a rate control membrane, a porous membrane and a microporous membrane.

5. The system of claim 1, wherein said analgesic reservoir comprises an amount of analgesic sufficient to induce and maintain analgesia in a human patient for a period of at least three days.

6. The system of claim 5 wherein said analgesic reservoir comprises an amount of dissolved fentanyl or analog thereof sufficient to induce and maintain analgesia for 3-7 days.

7. The system of claim 6, wherein said analgesic reservoir comprises a single phase formulation free of undissolved components.

8. The system of claim 7 wherein the analgesic reservoir is formed from an adhesive polymer.

9. The system of claim 8 wherein said analgesic reservoir comprises a polymer having a solubility for fentanyl of about 1 wt % to about 25 wt %.

10. The system of claim 9 wherein the reservoir comprises about 0.05 to about 1.75 mg/cm$^2$ of fentanyl or analogs thereof.

11. The system of claim 9 wherein the analgesic reservoir further comprises a permeation enhancer.

12. The system of claim 6, wherein the analgesic reservoir comprises a polymeric matrix comprising about 5 wt % to about 50 wt % of the analgesic, and optionally a permeation enhancer.

13. The system of claim 12 further comprising an analgesic release rate controlling means disposed between the analgesic reservoir and the skin, wherein said release rate controlling means is less permeable to the analgesic than to the permeation enhancer.

14. The system of claim 1, wherein said antagonist reservoir layer is disposed adjacent the skin distal surface of the barrier layer and the analgesic reservoir is disposed adjacent the skin proximal surface of the barrier layer.

15. The system of claim 14, wherein said antagonist reservoir layer comprises the antagonist dispersed within a polymer.

16. The system of claim 1, wherein the analgesic is fentanyl and upon ingestion or immersion of the system in a solvent for a period of time, the system substantially provides a release rate ratio of the antagonist to the analgesic of about 0.5:1 to about 20:1.

17. The system of claim 1, wherein the analgesic is sufentanil and upon ingestion or immersion of the system in a solvent for a period of time, the system substantially provides a release rate ratio of the antagonist to the analgesic of at least about 4:1.

18. The system of claim 1, wherein the system exhibits a standardized $C_{max}$ of about 0.01 to about 0.2 ng/ml-cm$^2$.

19. The system of claim 1, wherein the system exhibits a normalized $C_{max}$ of about 3.3 to about 82.5 ng/ml-(mg/h).

20. The system of claim 1, wherein the system exhibits an in vivo steady-state analgesic flux of about 0.1 to about 10 μg/h-cm$^2$.

21. The system of claim 3, wherein said analgesic reservoir comprises an amount of analgesic sufficient to induce and maintain analgesia in a human patient for a period of at least three days.

22. The system of claim 21 wherein said analgesic reservoir comprises an amount of dissolved fentanyl or analog thereof sufficient to induce and maintain analgesia for 3-7 days.

23. The system of claim 22, wherein said analgesic reservoir comprises a single phase formulation free of undissolved components.

24. The system of claim 23 wherein the analgesic reservoir is formed from an adhesive polymer.

25. The system of claim 24 wherein said analgesic reservoir comprises a polymer having a solubility for fentanyl of about 1 wt % to about 25 wt %; and further wherein the reservoir comprises about 0.05 to about 1.75 mg/cm$^2$ of fentanyl or analogs thereof.

26. The system of claim 25 wherein the analgesic reservoir further comprises a permeation enhancer.

27. The system of claim 22, wherein said antagonist reservoir layer comprises the antagonist dispersed within a polymer.

28. The system of claim 27, wherein the system exhibits a standardized $C_{max}$ of about 0.01 to about 0.2 ng/ml-cm$^2$.

29. The system of claim 27, wherein the system exhibits a normalized $C_{max}$ of about 3.3 to about 82.5 ng/ml-(mg/h).

30. The system of claim 27, wherein the system exhibits an in vivo steady-state analgesic flux of about 0.1 to about 10 μg/h-cm$^2$.

31. The system of claim 27, wherein the analgesic is a fentanyl analog and the analog is selected from the group consisting of alfentanil, lofentanil, remifentanil, sufentanil and trefentanil; and the antagonist is selected from the group consisting of naltrexone, methylnaltrexone, naloxone, nalbuphine, nalorphine, nalorphine dinicotinate, nalmefene, nadide, levallorphan, cyclozocine and pharmaceutically acceptable salts thereof.

32. The system of claim 28, wherein the analgesic is fentanyl and upon ingestion or immersion of the system in a solvent for a period of time, the system substantially provides a release rate ratio of the antagonist to the analgesic of about 0.5:1 to about 20:1.

33. The system of claim 32, wherein the antagonist is naltrexone.

34. The system of claim 33, wherein the system exhibits a standardized $C_{max}$ of about 0.01 to about 0.2 ng/ml-cm$^2$.

35. The system of claim 33, wherein the system exhibits a normalized $C_{max}$ of about 3.3 to about 82.5 ng/ml-(mg/h).

36. The system of claim 33, wherein the system exhibits an in vivo steady-state analgesic flux of about 0.1 to about 10 μg/h-cm$^2$.

37. The system of claim 28, wherein the analgesic is sufentanil and upon ingestion or immersion of the system in a solvent for a period of time, the system substantially provides a release rate ratio of the antagonist to the analgesic of at least about 4:1.

38. The system of claim 37, wherein the antagonist is naltrexone.

39. The system of claim 38, wherein the system exhibits a standardized $C_{max}$ of about 0.001 to about 0.05 ng/ml-cm$^2$.

40. The system of claim 38, wherein the system exhibits a normalized $C_{max}$ of about 0.04 to about 10 ng/ml-(mg/h).

41. The system of claim 38, wherein the system exhibits an in vivo steady-state analgesic flux of about 0.1 to about 10 μg/h-cm$^2$.

42. A transdermal system for administering an analgesic through the skin, the system having a reduced potential for abuse and including a multilaminate comprising:
  (a) an analgesic reservoir comprising an amount of analgesic sufficient to induce and maintain analgesia in a human patient, wherein the analgesic is fentanyl or an analog thereof, the analog being selected from the group consisting of alfentanil, carfentanil, lofentanil, remifentanil, sufentanil, and trefentanil;
  (b) an antagonist reservoir layer comprising an antagonist for said analgesic, the antagonist reservoir layer comprising an external edge of the system;
  (c) a barrier layer, said barrier layer separating said antagonist reservoir layer from said analgesic reservoir, said barrier layer being impermeable to said analgesic and to said antagonist; and
  (d) an antagonist release rate controlling layer disposed on the skin distal surface of the antagonist reservoir layer, wherein said antagonist release rate controlling layer substantially prevents release of the antagonist from the system upon securing the system to a human patient for a period of up to about 7 days, and further wherein the system provides release of the antagonist at a rate sufficient to provide an abuse limiting release rate ratio of the antagonist to the analgesic when the system is subject to abuse, such that the antagonist reservoir layer releases the antagonist through the external edge of the antagonist reservoir layer,
  wherein the antagonist is in a form that is not releasable through the barrier layer, the antagonist being releasable from the system upon being ingested or substantially immersed in a solvent.

43. A transdermal system for administering an analgesic through the skin, the system having a reduced potential for abuse and including a multilaminate comprising:
  (a) an analgesic reservoir comprising an amount of analgesic sufficient to induce and maintain analgesia in a human patient, wherein the analgesic is fentanyl or an analog thereof, the analog being selected from the group consisting of alfentanil, carfentanil, lofentanil, remifentanil, sufentanil, and trefentanil;
  (b) an antagonist reservoir layer comprising an antagonist for said analgesic, the antagonist reservoir layer comprising an external edge of the system;
  (c) a barrier layer, said barrier layer separating said antagonist reservoir layer from said analgesic reservoir, said barrier layer being impermeable to said analgesic and to said antagonist; and
  (d) an antagonist release rate controlling layer disposed on the skin distal surface of the antagonist reservoir layer, wherein said antagonist release rate controlling layer substantially prevents release of the antagonist from the system upon securing the system to a human patient for a period of up to about 7 days, and further wherein the system provides release of the antagonist at a rate sufficient to provide an abuse limiting release rate ratio of the antagonist to the analgesic upon ingestion or substantial immersion of the system in a solvent, such that the antagonist reservoir layer releases the antagonist through the external edge of the antagonist reservoir layer, wherein the antagonist is in a form that is not releasable through the barrier layer, the antagonist being releasable from the system upon being ingested or substantially immersed in the solvent.

44. The system of claim 42 or claim 43 wherein the antagonist release rate controlling layer is selected from a group consisting of a membrane, a film, a coating, a sheet, and a deposit on the antagonist reservoir layer.

45. The system of claim 44 wherein the antagonist release rate controlling layer is selected from a group consisting of a film, a rate control membrane, a porous membrane and a microporous membrane.

46. The system of claim 42 or claim 43, wherein said analgesic reservoir comprises an amount of analgesic sufficient to induce and maintain analgesia in a human patient for a period of at least three days.

47. The system of claim 46 wherein said analgesic reservoir comprises an amount of dissolved fentanyl or analog thereof sufficient to induce and maintain analgesia for 3-7days.

48. The system of claim 47, wherein said analgesic reservoir comprises a single phase formulation free of undissolved components.

49. The system of claim 48 wherein the analgesic reservoir is formed from an adhesive polymer.

50. The system of claim 49 wherein said analgesic reservoir comprises a polymer having a solubility for fentanyl of about 1 wt % to about 25 wt %.

51. The system of claim 50 wherein the reservoir comprises about 0.05 to about 1.75 mg/cm$^2$ of fentanyl or analogs thereof.

52. The system of claim 50 wherein the analgesic reservoir further comprises a permeation enhancer.

53. The system of claim 47, wherein the analgesic reservoir comprises a polymeric matrix comprising about 5 wt % to about 50 wt % of the analgesic, and optionally a permeation enhancer.

54. The system of claim 48, wherein said antagonist reservoir layer comprises the antagonist dispersed within a polymer.

55. The system of claim 54, wherein the system exhibits a standardized $C_{max}$ of about 0.01 to about 0.2 ng/ml-cm$^2$.

56. The system of claim 54, wherein the system exhibits a normalized $C_{max}$ of about 3.3 to about 82.5 ng/ml-(mg/h).

57. The system of claim 54, wherein the system exhibits an in vivo steady-state analgesic flux of about 0.1 to about 10 µg/h-cm$^2$.

58. The system of claim 44, wherein said analgesic reservoir comprises an amount of analgesic sufficient to induce and maintain analgesia in a human patient for a period of at least three days, and said antagonist reservoir layer comprises the antagonist dispersed within a polymer.

59. The system of claim 58 wherein said analgesic reservoir comprises a single phase formulation free of undissolved components.

60. The system of claim 59 wherein said analgesic reservoir comprises a polymer having a solubility for fentanyl of about 1 wt % to about 25 wt %; about 0.05 to about 1.75 mg/cm$^2$ of fentanyl or analogs thereof; and optionally a permeation enhancer.

61. The system of claim 60, wherein the system exhibits a standardized $C_{max}$ of about 0.01 to about 0.2 ng/ml-cm$^2$.

62. The system of claim 60, wherein the system exhibits a normalized $C_{max}$ of about 3.3 to about 82.5 ng/ml-(mg/h).

63. The system of claim 60, wherein the fentanyl analog is selected from the group consisting of alfentanil, lofentanil, remifentanil, sufentanil and trefentanil; and the antagonist is selected from the group consisting of naltrexone, methylnaltrexone, naloxone, nalbuphine, nalorphine, nalorphine dinicotinate, nalmefene, nadide, levallorphan, cyclozocine and pharmaceutically acceptable salts thereof.

64. The system of claim 63, wherein the analgesic is fentanyl and upon ingestion or immersion of the system in a solvent for a period of time, the system substantially provides a release rate ratio of the antagonist to the analgesic of about 0.5:1 to about 20:1.

65. The system of claim 64, wherein the antagonist is naltrexone.

66. The system of claim 65, wherein the system exhibits a standardized $C_{max}$ of about 0.01 to about 0.2 ng/ml-cm$^2$.

67. The system of claim 65, wherein the system exhibits a normalized $C_{max}$ of about 3.3 to about 82.5 ng/ml-(mg/h).

68. The system of claim 63, wherein the analgesic is sufentanil and upon ingestion or immersion of the system in a solvent for a period of time, the system substantially provides a release rate ratio of the antagonist to the analgesic of at least about 4:1.

69. The system of claim 68, wherein the antagonist is naltrexone.

70. The system of claim 69, wherein the system exhibits a standardized $C_{max}$ of about 0.001 to about 0.05 ng/ml-cm$^2$.

71. The system of claim 69, wherein the system exhibits a normalized $C_{max}$ of about 0.04 to about 10 ng/ml-(mg/h).

72. A transdermal system for administering fentanyl through the skin, the system having a reduced potential for abuse and including a multilaminate comprising:
 (a) an analgesic reservoir comprising a single phase polymeric composition free of undissolved components containing a polyacrylate adhesive having sufficient solubility for fentanyl to contain dissolved fentanyl in an amount sufficient to induce and maintain analgesia in a human for at least three days;
 (b) an antagonist reservoir layer comprising an antagonist for said analgesic, the antagonist reservoir layer comprising an external edge of the system;
 (c) a barrier layer, said barrier layer separating said antagonist reservoir layer from said analgesic reservoir, said barrier layer being impermeable to said analgesic and to said antagonist; and
 (d) an antagonist release rate controlling layer disposed on the skin distal surface of the antagonist reservoir layer, wherein said barrier layer and said antagonist release rate controlling layer substantially prevent release of the antagonist from the system upon securing the system to a human patient for a period of up to about 7 days, and further wherein the system provides release of the antagonist at a rate sufficient to provide an abuse limiting release rate ratio of the antagonist to the analgesic upon ingestion or substantial immersion of the system in a solvent, such that the antagonist reservoir layer releases the antagonist through the external edge of the antagonist reservoir layer,
 wherein the antagonist is in a form that is not releasable through the barrier layer, the antagonist being releasable from the system upon being ingested or substantially immersed in the solvent.

73. A transdermal system for administering fentanyl through the skin, the system having a reduced potential for abuse and including a multilaminate comprising:
 (a) an analgesic reservoir comprising a single phase polymeric composition free of undissolved components containing a polyaerylate adhesive having sufficient solubility for fentanyl to contain dissolved fentanyl in an amount sufficient to induce and maintain analgesia in a human for at least three days;

(b) an antagonist reservoir layer comprising an antagonist for said analgesic, the antagonist reservoir layer comprising an external edge of the system;

(c) a barrier layer, said barrier layer separating said antagonist reservoir layer from said analgesic reservoir, said barrier layer being impermeable to said analgesic and to said antagonist; and (d) an antagonist release rate controlling layer disposed on the skin distal surface of the antagonist reservoir layer, wherein said barrier layer and said antagonist release rate controlling layer substantially prevent release of the antagonist from the system upon securing the system to a human patient for a period of up to about 7 days, and upon ingestion or immersion of the system in a solvent for a period of time, the system provides a release rate ratio of the antagonist to the analgesic of about 0.5:1 to about 20:1, such that the antagonist reservoir layer releases the antagonist through the external edge of the antagonist reservoir layer, wherein the antagonist is in a form that is not releasable through the barrier layer, the antagonist being releasable from the system upon being ingested or substantially immersed in the solvent.

74. The system of claim 72 or 73 wherein
(a) the analgesic reservoir comprises about 0.05 to about 1.75 mg/cm$^2$ of fentanyl base;
(b) the antagonist reservoir layer comprises about 0.2 to about 15 mg/cm$^2$ of the antagonist dispersed in a polymer or a copolymer selected from the group consisting of polyolefin, polyethylene, polyoctene, polyvinyl acetate, polymethyl acrylate, polyethyl acrylate, polystyrene, polyethyleneoctene copolymers, ethylene-vinyl acetate copolymer (EVA), ethylenemethyl acrylate copolymers (EMA), ethylene-acrylic acid copolymer, and ethylene-ethylacrylate copolymer;
(c) the barrier layer comprises a polyester laminated to a polymer selected from the group consisting of polyurethane, polyethylene and ethylene copolymers; and
(d) the antagonist release rate controlling layer is a microporous layer selected from the group consisting of microporous ultra high density polyethylene (UHDPE), microporous polypropylene, polyester capillary pore membrane, spun laced polyester, polypropylene and polyethylene.

75. The system of claim 74, wherein the system exhibits a standardized $C_{max}$ of about 0.01 to about 0.2 ng/ml-cm$^2$.

76. The system of claim 74, wherein the system exhibits a normalized $C_{max}$ of about 3.3 to about 82.5 ng/ml-(mg/h).

77. The system of claim 74, wherein the antagonist is naltrexone.

78. A transdermal system for administering sufentanil through the skin, the system having a reduced potential for abuse and including a multilaminate comprising:

(a) an analgesic reservoir comprising a single phase polymeric composition free of undissolved components containing a polyacrylate adhesive having sufficient solubility for sufentanil to contain dissolved sufentanil in an amount sufficient to induce and maintain analgesia in a human for at least three days;

(b) an antagonist reservoir layer comprising an antagonist for said analgesic, the antagonist reservoir layer comprising an external edge of the system;

(c) a barrier layer, said barrier layer separating said antagonist reservoir layer from said analgesic reservoir, said barrier layer being impermeable to said analgesic and to said antagonist; and (d) an antagonist release rate controlling layer disposed on the skin distal surface of the antagonist reservoir layer, wherein said barrier layer and said antagonist release rate controlling layer substantially prevent release of the antagonist from the system upon securing the system to a human patient for a period of up to about 7 days, and further wherein the system provides release of the antagonist at a rate sufficient to provide an abuse limiting release rate ratio of the antagonist to the analgesic upon ingestion or substantial immersion of the system in a solvent, such that the antagonist reservoir layer releases the antagonist through the external edge of the antagonist reservoir layer, wherein the antagonist is in a form that is not releasable through the barrier layer, the antagonist being releasable from the system upon being ingested or substantially immersed in the solvent.

79. A transdermal system for administering sufentanil through the skin, the system having a reduced potential for abuse and including a multilaminate comprising:

(a) an analgesic reservoir comprising a single phase polymeric composition free of undissolved components containing a polyacrylate adhesive having sufficient solubility for sufentanil to contain dissolved sufentanil in an amount sufficient to induce and maintain analgesia in a human for at least three days;

(b) an antagonist reservoir layer comprising an antagonist for said analgesic, the antagonist reservoir layer comprising an external edge of the system;

(c) a barrier layer, said barrier layer separating said antagonist reservoir layer from said analgesic reservoir, said barrier layer being impermeable to said analgesic and to said antagonist; and (d) an antagonist release rate controlling layer disposed on the skin distal surface of the antagonist reservoir layer, wherein said barrier layer and said antagonist release rate controlling layer substantially prevent release of the antagonist from the system upon securing the system to a human patient for a period of up to about 7 days, and upon ingestion or immersion of the system in a solvent for a period of time, the system provides a release rate ratio of the antagonist to the analgesic of at least about 4:1, such that the antagonist reservoir layer releases the antagonist through the external edge of the antagonist reservoir layer, wherein the antagonist is in a form that is not releasable through the barrier layer, the antagonist being releasable from the system upon being ingested or substantially immersed in the solvent.

80. The system of claim 78 or 79 wherein
(a) the analgesic reservoir comprises about 0.05 to about 1.75 mg/cm$^2$ of sufentanil base;
(b) the antagonist reservoir layer comprises about 0.2 to about 15 mg/cm$^2$ of the antagonist dispersed in a polymer or a copolymer selected from the group consisting of polyolefin, polyethylene, polyoctene, polyvinyl acetate, polymethyl acrylate, polyethyl acrylate, polystyrene, polyethyleneoctene copolymers, ethylene-vinyl acetate copolymer (EVA), ethylenemethyl acrylate copolymers (EMA), ethylene-acrylic acid copolymer, and ethylene-ethylaerylate copolymer;

(c) the barrier layer comprises a polyester laminated to a polymer selected from the group consisting of polyurethane, polyethylene and ethylene copolymers; and (d) the antagonist release rate controlling layer is a microporous layer selected from the group consisting of microporous ultra high density polyethylene (UHDPE), microporous polypropylene, polyester capillary pore membrane, spun laced polyester, polypropylene and polyethylene.

81. The system of claim 80, wherein the system exhibits a standardized $C_{max}$ of about 0.001 to about 0.05 ng/ml-cm$^2$.

82. The system of claim 80, wherein the system exhibits a normalized $C_{max}$ of about 0.04 to about 10 ng/ml-(mg/h).

83. The system of claim 80, wherein the antagonist is naltrexone.

84. A method of reducing drug abuse of a transdermal drug delivery system including a multilaminate, comprising:

(a) providing a transdermal drug delivery system that has an analgesic reservoir comprising an analgesic, the analgesic being selected from the group consisting of fentanyl and analogs thereof; an antagonist reservoir layer comprising an antagonist for said analgesic, the antagonist reservoir layer comprising an external edge of the system; and a barrier layer separating said antagonist reservoir layer from said analgesic reservoir, said barrier layer being impermeable to said analgesic and to said antagonist, wherein the system (i) has an antagonist release rate controlling layer that substantially prevents release of the antagonist from the system upon securing the system to a human patient for a period of up to about 7 days; and (ii) provides release of the antagonist at a rate sufficient to provide an abuse limiting release rate ratio of the antagonist to the analgesic when the system is subject to abuse, such that the antagonist reservoir layer releases the antagonist through the external edge of the antagonist reservoir layer when subject to abuse; and (b) wearing the transdermal drug delivery system for a period of up to 7 days for transdermal delivery of the analgesic while substantially preventing release of the antagonist from the system such that the antagonist is retained in the device during this period and can be released when the system is subject to abuse.

85. A method of making a transdermal drug delivery system including a multilaminate, comprising:

(a) providing an analgesic reservoir containing an analgesic and an antagonist reservoir layer containing an antagonist of that analgesic;

(b) providing an antagonist release rate controlling layer; and (c) forming a transdermal drug delivery system that has the analgesic reservoir and the antagonist reservoir layer being separated by a barrier layer, the antagonist reservoir layer comprising an external edge of the system, the analgesic being selected from the group consisting of fentanyl and analogs thereof; said barrier layer being impermeable to said analgesic and to said antagonist; the antagonist release rate controlling layer substantially preventing release of the antagonist for the system upon securing the system to a human patient for a period of up to about 7 days and the system releases the antagonist at a rate sufficient to provide an abuse limiting release rate ratio of the antagonist to the analgesic when the system is subject to abuse, such that the antagonist reservoir layer releases the antagonist through the external edge of the antagonist reservoir layer when subject to abuse.

\* \* \* \* \*